(12) United States Patent
Keil et al.

(10) Patent No.: US 7,834,030 B2
(45) Date of Patent: Nov. 16, 2010

(54) PHENYL-[1,2,4]-OXADIAZOL-5-ONE DERIVATIVES, PHARMACEUTICAL COMPOSITIONS AND THERAPEUTIC USE THEREOF

(75) Inventors: Stefanie Keil, Frankfurt am Main (DE); Patrick Bernardelli, Paris (FR); Matthias Urmann, Frankfurt am Main (DE); Hans Matter, Frankfurt am Main (DE); Wolfgang Wendler, Frankfurt am Main (DE); Maike Glien, Frankfurt am Main (DE); Karen Chandross, Somerset, NJ (US); Lan Lee, Pluckemin Park, NJ (US)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/055,764

(22) Filed: Mar. 26, 2008

(65) Prior Publication Data

US 2008/0262036 A1 Oct. 23, 2008

Related U.S. Application Data

(63) Continuation of application No. PCT/EP2006/009304, filed on Sep. 26, 2006.

(30) Foreign Application Priority Data

Sep. 29, 2005 (EP) .................................. 05021235

(51) Int. Cl.
| | |
|---|---|
| *A61K 31/4709* | (2006.01) |
| *A61K 31/427* | (2006.01) |
| *A61K 31/454* | (2006.01) |
| *A61P 3/00* | (2006.01) |
| *C07D 417/12* | (2006.01) |
| *C07D 417/14* | (2006.01) |

(52) U.S. Cl. .................. 514/314; 514/326; 514/365; 546/167; 546/209; 548/204

(58) Field of Classification Search ........................ None
See application file for complete search history.

(56) References Cited

U.S. PATENT DOCUMENTS 5,641,796 A 6/1997 Dominianni et al.

6,710,063 B1 3/2004 Chao et al.

FOREIGN PATENT DOCUMENTS

| EP | 1424330 | 6/2004 |
|---|---|---|
| EP | 1586573 | 10/2005 |
| WO | WO 96/13264 | 5/1996 |
| WO | WO 00/78313 | 12/2000 |
| WO | WO 2005/097762 | 10/2005 |

OTHER PUBLICATIONS

Kulkarni, S.S., et al., Three-Dimensional Quantitative Structure Activity Relationships (3-D-QSAR) of Antihyperglycemic Agents, Bioorganic & Medicinal Chemistry vol. 7, (1999) pp. 1475-1485.

*Primary Examiner*—Kamal A Saeed
(74) *Attorney, Agent, or Firm*—Jiang Lin

(57) ABSTRACT

The present invention comprises phenyl-[1,2,4]-oxadiazol-5-one derivatives of the general formula I:

Formula I

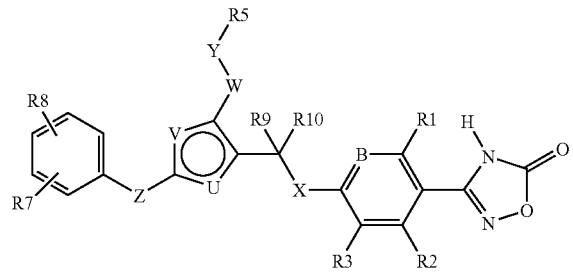

wherein the R1-R10 and B, U, V, W, X, Y and Z substituents are defined herein. The claimed invention also comprises the compounds isomers and their physiologically acceptable salts as well as processes for their preparation. The compounds are suitable for the treatment and/or prevention of disorders of fatty acid metabolism and glucose utilization disorders as well as of disorders in which insulin resistance is involved and demyelinating and other neurodegenerative disorders of the central and peripheral nervous system.

32 Claims, No Drawings

PHENYL-[1,2,4]-OXADIAZOL-5-ONE DERIVATIVES, PHARMACEUTICAL COMPOSITIONS AND THERAPEUTIC USE THEREOF

CROSS-REFERENCE TO RELATED APPLICATIONS

This application is a continuation of International Patent Application No. PCT/EP2006/009304 filed on Sep. 26, 2006 which is incorporated herein by reference in its entirety which also claims the benefit of priority of European Patent Application No. 05021235.6 filed on Sep. 29, 2005.

FIELD OF THE INVENTION

The present invention relates generally to pharmaceutical compositions for the treatment of metabolic disorders and the diseases and physiological problems resulting therefrom. More specifically, the present invention relates to compounds which are able to therapeutically modulate lipid and/or carbohydrate metabolism in mammals and are thus suitable for the prevention and/or treatment of diseases such as type-2 diabetes, atherosclerosis, cardiovascular disorders and the like. The inventive compounds of the present invention are also useful in the treatment of the demyelinating and other neurodegenerative disorders of the central and peripheral nervous systems.

BACKGROUND OF THE INVENTION

PPAR agonists are well known and have been described in the prior art, (see U.S. Pat. No. 6,200,995 to De La Brouse-Elwood et. al.; WO 03/043997 to Johnston et. al. and WO 01/00603 and WO 02/092590 to Keil et. al.) Compounds comprising an oxadiazolone feature as inhibitors of factor Xa were disclosed in DE 101 12 768 A1 and oxodiazolones have also been described as oral hypoglycemic agents in WO 96/13264, WO 02/092590, WO2004/080943, WO2005/054213 and WO2005/097786). Compounds comprising an oxadiazolone feature as inhibitors of factor Xa were disclosed in DE 101 12 768 A1, oral hypoglycemic agents in WO 96/13264. From WO 97/40017 compounds having a phenyl group linked to heterocycles are known as modulators of molecules with phosphotyrosine recognition units. Benzene derivatives as inhibitors of squalene synthase and protein farnesyltransferase are described in WO96/34851 to Stapper et. al.

SUMMARY OF THE INVENTION

The present invention comprises phenyl-[1,2,4]-oxadiazol-5-one derivatives of the general formula I:

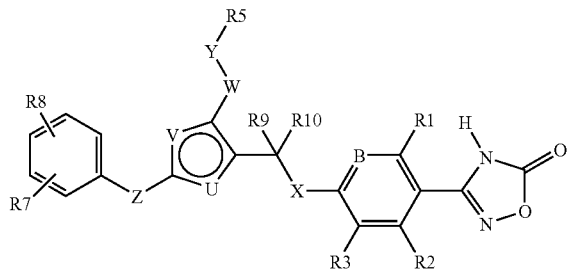

Formula I wherein the R1-R10 and B, U, V, W, X, Y and Z substituents are defined herein. The claimed invention also comprises the compounds isomers and their physiologically acceptable salts as well as processes for their preparation. The compounds are suitable for the treatment and/or prevention of disorders of fatty acid metabolism and glucose utilization disorders as well as of disorders in which insulin resistance is involved and demyelinating and other neurodegenerative disorders of the central and peripheral nervous system.

DETAILED DESCRIPTION OF THE INVENTION

The present invention comprises compounds capable of therapeutically modulating lipid and/or carbohydrate metabolism and are thus suitable for the prevention and/or treatment of diseases such as type-2 diabetes and atherosclerosis and the physiological manifestations thereof. Another purpose of the invention is to treat demyelinating and other neurodegenerative disorders of the central and peripheral nervous systems. This series of compounds modulates the activity of peroxisome proliferator activated (PPA) receptors and are therefore suitable in particular for activating PPARdelta and PPARalpha receptors, however, the extent of the relative activation of the receptors varies depending on the compound involved Compounds of the present invention are described by formula I:

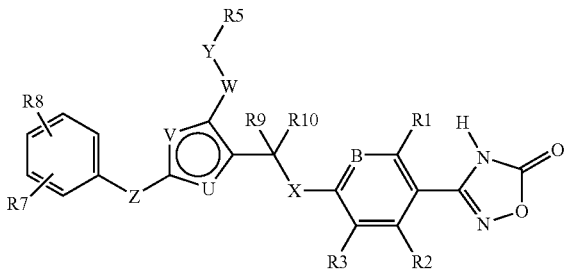

Formula I wherein:
R1 is selected from the group consisting of H, halogen, (C1-C8) alkyl, (C0-C4) alkylene-O—(C0-C4) alkylene-H, (C3-C7) cycloalkyl, SCH3, CN, (C6-C10) aryl, wherein alkyl, alkylene and aryl are unsubstituted or 1- to 5-fold substituted by F;

B is C(R4) or N;

R2 and R3 are independently selected from the group consisting of H, halogen, (C1-C8) alkyl, (C0-C4) alkylene-O—(C0-C4) alkylene-H, (C3-C7) cycloalkyl, SCH3, CN, and a (C6-C10) aryl, wherein alkyl, alkylene and aryl are unsubstituted or 1- to 5-fold substituted by F; or R2 and R3 together with the carbon atoms to which they are bonded form a (C6-C10) aryl or a (C5-C10) heteroaryl ring.

R4 is selected from the group consisting of H, halogen, (C1-C8) alkyl, (C0-C4) alkylene-O—(C0-C4) alkylene-H, (C3-C7) cycloalkyl, SCH3, CN and (C6-C10) aryl, wherein alkyl, alkylene and aryl are unsubstituted or 1- to 5-fold substituted by F;

X is selected from the group consisting of O, S, S(O), S(O)2, O—CH2, S—CH2, CH2—O, CH2—S; —CH2

Z is selected from the group consisting of a bond, (C1-C8) alkylene, (C2-C8) alkenylene, (C2-C8) alkylidene and (C1-C6) alkylene-O—(C1-C6) alkyl;

U or V is N and the other is S or O;

W is selected from the group consisting of a bond, (C1-C8) alkylene, (C2-C8) alkenylene, wherein alkylene and alkenylene are unsubstituted or mono-, di- or tri-substituted by OH and F;

Y is selected from the group consisting of a bond, O, S, S(O), S(O)2 and N(R6) and, R5 is selected from the group consisting of H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, (C0-C4) alkylene-(C5-C15) heteroaryl, wherein alkyl and alkylene can be mono-, di- or tri-substituted by F, (C1-C4) alkyl and O—(C0-C4) alkylene-H and wherein cycloalkyl, aryl, heterocycloalkyl, heterocycloalkenyl and heteroaryl are mono-, di- or tri-substituted by F, Cl, Br, CF3, (C1-C4) alkyl and O—(C0-C4) alkylene-H;

R6 is selected from the group consisting of H, (C1-C8) alkyl, (C2-C8) alkenyl, and (C0-C4) alkylene-(C3-C6) cycloalkyl, wherein alkyl and alkenyl are unsubstituted or mono-, di- or tri-substituted by F and O—(C0-C4)-alkylene-H; or R5 and R6 together with the nitrogen atom to which they are bonded (Y=N(R6)) form a (C3-C9)-heterocycloalkyl, a (C3-C9)-heterocycloalkenyl or a (C5-C9)-heteroaryl which can contain additionally 1 to 3 heteroatoms N, O, S and which is unsubstituted or mono- or di-substituted by F, CF3, (C1-C4) alkyl, O—(C1-C4) alkyl, CH2—OH, SO2—(C1-C4) alkyl, CO—(C1-C4) alkyl, C0—NH2, NH—CO—(C1-C4) alkyl, (C6-C14) aryl and (C5-C15) heteroaryl;

R7 and R8 are independently selected from the group consisting of H, halogen, (C1-C8) alkyl, (C0-C4) alkylene-O—(C0-C4) alkylene-H, SCF3, SF5, S(O)2CF3, (C0-C4) alkylene-O—(C6-C12) aryl, (C0-C4) alkylene-(C6-C12) aryl, NO2, wherein alkyl and alkylene are unsubstituted or mono-, di- or tri-substituted by F and aryl is unsubstituted or mono-, di- or tri-substituted by halogen, (C1-C4) alkyl or O—(C1-C4) alkyl;

R9 is selected from the group consisting of (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, (C0-C6) alkylene-(C3-C8) cycloalkenyl, wherein alkyl and alkylene are unsubstituted or mono-, di- or tri-substituted by F and aryl, heteroaryl, cycloalkyl and cycloalkenyl are unsubstituted or mono-, di- or tri-substituted by halogen, (C1-C4) alkyl, —CF3, —CHF2, or O—(C1-C4)alkyl;

R10 is selected from the group consisting of H, F, (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, (C0-C6) alkylene-(C3-C8) cycloalkenyl, wherein alkyl and alkylene are unsubstituted or mono-, di- or tri-substituted by F and aryl, heteroaryl, cycloalkyl and cycloalkenyl are unsubstituted or mono-, di- or tri-substituted by halogen, (C1-C4) alkyl, —CF3, —CHF2, or O—(C1-C4) alkyl;

its' stereoisomers, enantiomers, tautomers, their physiologically acceptable salts and mixtures thereof.

Yet another preferable embodiment of the present invention are compounds of formula I wherein B is C(R4) and R4 is H.

Another embodiment according to the invention are compounds of formula I wherein X is O or O—CH2.

Yet another embodiment according to the invention are compounds of formula I wherein X is O.

Another embodiment according to the invention are compounds of formula I wherein X is O—CH2.

Another embodiment according to the invention are compounds of formula I, wherein R1 is selected from the group consisting of H, halogen, (C1-C4) alkyl, (C0-C4) alkylene-O—(C0-C2) alkylene-H, (C3-C6) cycloalkyl, phenyl, wherein alkyl, alkylene and phenyl are unsubstituted or mono, di- or trisubstituted by F.

Another embodiment according to the invention are compounds of formula I, wherein R2 is H and R3 is H or F or R2 and R3 together with the C-atoms to which they are bonded form a (C6)-aryl or a (C5-C6) heteroaryl ring.

Another embodiment according to the invention are compounds of formula I, wherein R2 is H and R3 is H or F.

Another embodiment according to the invention are compounds of formula i, wherein R2 and R3 together with the C-atoms to which they are bonded form a (C6)-aryl or a (C5-C6) heteroaryl ring.

Another embodiment according to the invention are compounds of formula I, wherein W is CH2, Y is a bond, R5 is H.

Another embodiment according to the invention are compounds of formula I, wherein Z is a bond.

Another embodiment according to the invention are compounds of formula I, wherein U is O, S and V is N.

Another embodiment according to the invention are compounds of formula I, wherein U is S and V is N.

Another embodiment according to the invention are compounds of formula I, wherein R7 is F, Cl, (C1-C4) alkyl, (C0-C2) alkylene-O—(C1-C2) alkylene-H, (C0-C4) alkylene-phenyl, wherein alkyl, alkylene and phenyl are unsubstituted or mono-, di- or trisubstituted by F, and R8 is H.

Another embodiment according to the invention are compounds of formula I, wherein R7 is in para-position to Z.

Another embodiment according to the invention are compounds of the formula I, wherein R8 is H.

Another embodiment according to the invention are compounds of formula I, wherein R9 is selected from the group consisting of (C1-C4) alkyl, (C0-C3) alkylene-(C6-C10) aryl, (C0-C3) alkylene-(C5-C6) heteroaryl, (C0-C3) alkylene-(C3-C6) cycloalkyl, wherein alkyl and alkylene, are unsubstituted or mono-, di- or tri-substituted by F and aryl, heteroaryl and cycloalkyl are unsubstituted or mono-, di- or tri-substituted by halogen, (C1-C4) alkyl, —CF3, —CHF2, or 0-(C1-C4)alkyl; and R10 is H.

Another embodiment according to the invention are compounds of formula I, wherein W is a bond, (C1-C3) alkylene;
Y is a bond, N(R6) and
R5 is H, (C1-C3) alkyl, wherein alkyl can be mono-, di- or tri-substituted by F;
R6 is H, (C1-C3) alkyl, wherein alkyl can be mono-, di- or tri-substituted by F;
R5 and R6 together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl;

Another embodiment according to the invention are compounds of formula I, wherein R1 is selected from the group consisting of H, halogen, (C1-C4) alkyl, (C0-C4) alkylene-O—(C0-C2) alkylene-H, (C3-C6) cycloalkyl, phenyl, wherein alkyl, alkylene and phenyl are unsubstituted or mono-, di- or trisubstituted by F;
R9 is selected from the group consisting of (C1-C4) alkyl, (C0-C3) alkylene-phenyl, (C0-C3) alkylene-(C5-C6) heteroaryl, (C0-C3) alkylene-(C3-C6) cycloalkyl, wherein alkyl, alkylene, phenyl, heteroaryl and cycloalkyl are unsubstituted or mono-, di- or tri-substituted by F; and
R10 is H.

Another embodiment according to the invention are compounds of formula I, wherein R1 is selected from the group consisting of H, halogen, (C1-C4) alkyl, (C0-C4) alkylene-O—(C0-C2) alkylene-H, (C3-C6) cycloalkyl, phenyl, wherein alkyl, alkylene and phenyl are unsubstituted or mono-, di- or trisubstituted by F;
W is a bond, (C1-C3) alkylene;
Y is a bond or N(R6) and
R5 is selected from the group consisting of H, (C1-C3) alkyl, wherein alkyl can be mono-, di- or tri-substituted by F;
R6 is selected from the group consisting of H, (C1-C3) alkyl, wherein alkyl can be mono-, di- or tri-substituted by F;
R5 and R6 together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl.

Another embodiment according to the invention are compounds of formula I, wherein R1 is selected from the group consisting of H, halogen, (C1-C4) alkyl, (C0-C4) alkylene-O—(C0-C2) alkylene-H, (C3-C6) cycloalkyl and phenyl, wherein alkyl, alkylene and phenyl are unsubstituted or mono-, di- or trisubstituted by F;
R9 is selected from the group consisting of (C1-C4) alkyl, (C0-C3) alkylene-phenyl, (C0-C3) alkylene-(C5-C6) heteroaryl and (C0-C3) alkylene-(C3-C6) cycloalkyl, wherein alkyl, alkylene, phenyl, heteroaryl and cycloalkyl are unsubstituted or mono-, di- or tri-substituted by F; and
R10 is H.
W is a bond or (C1-C3) alkylene;
Y is a bond or N(R6) and
R5 is selected from the group consisting of H, (C1-C3) alkyl, wherein alkyl can be mono-, di- or tri-substituted by F;
R6 is selected from the group consisting of H, (C1-C3) alkyl, wherein alkyl can be mono-, di- or tri-substituted by F;
R5 and R6 together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl;

Another embodiment according to the invention are compounds of formula I where one or more substituents have the following meaning:

R1 is selected from the group consisting of H, halogen, OH, O—(C1-C2) alkyl, and (C3-C6) cycloalkyl, wherein alkyl is unsubstituted or mono-, di- or trisubstituted by F;
R2 is H;
R3 is H or F;
B is C(R4) and
R4 is H;
X is O or O—CH2;
V is N and
U is O, S;
W is a bond, CH2;
Y is a bond, N(R6);
R5 is selected from the group consisting of H, (C1-C3) alkyl, wherein alkyl can be mono-, di- or tri-substituted by F;
R6 is selected from the group consisting of H, (C1-C3) alkyl, wherein alkyl can be mono-, di- or tri-substituted by F;
R5 and R6 together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl; preferably piperidine which is unsubstituted or mono- or di-substituted by F, CF3, (C1-C3) alkyl, O—(C1-C3) alkyl; most preferably piperidine monosubstituted by CF3;
Z is a bond;
R7 is selected from the group consisting of H, halogen, (C1-C3) alkyl, O—(C1-C3) alkyl, phenyl, wherein alkyl and phenyl are unsubstituted or mono-, di- or tri-substituted by F;
R8 is H;
R9 is selected from the group consisting of (C1-C4) alkyl, (C0-C3) alkylene-phenyl, (C0-C3) alkylene-(C5-C6) heteroaryl, and (C0-C3) alkylene-(C3-C6) cycloalkyl, wherein alkyl, alkylene, phenyl and heteroaryl are unsubstituted or mono-, di- or tri-substituted by F;
R10 is H.

Another embodiment according to the invention are compounds of formula I where one or more substituents have the following meaning:

R1 is selected from the group consisting of H, halogen, (C1-C2) alkylene-O—(C1-C2) alkyl and (C3-C6) cycloalkyl, wherein alkylene and alkyl are unsubstituted or mono, di- or trisubstituted by F;
R2 is H;
R3 is H, F;
B is C(R4) and
R4 is H;
X is O, O—CH2;
V is N and
U is O, S;
W is CH2;
Y is a bond;
R5 is H;
Z is a bond;
R7 is selected from the group consisting of H, halogen, (C1-C3) alkyl, O—(C1-C3) alkyl, phenyl, wherein alkyl and phenyl are unsubstituted or mono-, di- or tri-substituted by F;
R8 is H;
R9 is selected from the group consisting of (C1-C4) alkyl, (C0-C3) alkylene-phenyl, (C0-C3) alkylene-(C5-C6) heteroaryl and (C0-C3) alkylene-(C3-C6) cycloalkyl, wherein alkyl, alkylene, phenyl, cycloalkyl and heteroaryl are unsubstituted or mono-, di- or tri-substituted by F;
R10 is H.

Another embodiment according to the invention are compounds of formula I where one or more substituents have the following meaning:
B is C(R4), N;
R1 is selected from the group consisting of H, F, Cl, Br, OH, O—CH3, O—CHF2, O—CH2—CF3, CF3, CH2—CH3, CH2—O—CH2—CF3, CH2—O—CH3, CH2—O—CH2-CH3 and cyclopropyl;
R2 is H;
R3 is H, F;
R4 is H;
R2 and R3 together with the carbon atoms to which they are bonded and the ring carrying them form a naphthalene or a quinoline-ring.
X is O, CH2, O—CH2;
V is N,
U is S;
W is CH2;
Y is a bond, N(R6);
R5 is H;
R5 and R6 together with the nitrogen atom to which they are bonded (Y═N(R6)) form a piperidine which is monosubstituted by CF3;
Z is a bond;
R7 is CF3;
R8 is H;
R9 is selected from the group consisting of CH3, CH2CH3, C3H7, C4H9, CF3, CF2—CH2-CH3, phenyl, CH2-phenyl, CH2—CH2-phenyl, CH2-4-F-phenyl, CH2-pyridyl, CF2-cyclopropyl, and CF2-4-CHF2-phenyl;
R10 is H.

Another embodiment according to the invention are compounds of formula I where one or more substituents have the following meaning:
R1 is F, OH, OCH3, OCHF2, OCH2—CF3;
R2 is H;
R3 is H, F;
B is C(R4) and
R4 is H;
X is O;
V is N and
U is S;
W is a bond, CH2;
Y is a bond, N(R6);
R5 is CH3;
R5 and R6 together with the nitrogen atom to which they are bonded (Y N(R6)) form a piperidine which is unsubstituted or mono- or di-substituted by F, CF3, (C1-C3) alkyl, O—(C1-C3) alkyl, preferably by CF3;
Z is a bond;
R7 is CF3;
R8 is H;
R9 is CH2—CH3;
R10 is H.

Another embodiment according to the invention are compounds of formula I where one or more substituents have the following meaning:
R1 is selected from the group consisting of H Cl, F, CH3, CH2—CH3, cyclopropyl, CF3, CH2—O—CH3, CH2—O—CH2—CF3, CH2—O—CH2—CH3 and 4-F-phenyl;
R2 is H;
R3 is H;
B is C(R4) and
R4 is H;
X is O, O—CH2;
V is N and
U is S;
W is CH2;
Y is a bond;
R5 is H;
Z is a bond;
R7 is CF3;
R8 is H;
R9 is CH2—CH3, CH2-phenyl, CH2-4-F-phenyl, CH2-pyridyl, CF3, CF2—CH3, —CF2-cyclopropyl;
R10 is H.

Most preferred compounds are:
3-(2-Chloro-4-{1-[4-methyl-2-(4-trifluoromethyl-phenyl)-thiazol-5-yl]-ethoxy}-phenyl)-4H-[1,2,4]oxadiazol-5-one
3-(2-Chloro-4-{2-methyl-1-[4-methyl-2-(4-trifluoromethyl-phenyl)-thiazol-5-yl]-propoxy}-phenyl)-4H-[1,2,4]oxadiazol-5-one
3-(2-Chloro-4-{3-methyl-1-[4-methyl-2-(4-trifluoromethyl-phenyl)-thiazol-5-yl]-butoxy}-phenyl)-4H-[1,2,4]oxadiazol-5-one
3-(2-Chloro-4-{1-[4-methyl-2-(4-trifluoromethyl-phenyl)-thiazol-5-yl]-propoxy}-phenyl)-4H-[1,2,4]oxadiazol-5-one
3-(2-Chloro-4-{1-[4-methyl-2-(4-trifluoromethyl-phenyl)-thiazol-5-yl]-2-phenyl-ethoxy}-phenyl)-4H-[1,2,4]oxadiazol-5-one
3-(2-Chloro-4-{[4-methyl-2-(4-trifluoromethyl-phenyl)-thiazol-5-yl]-phenyl-methoxy}-phenyl)-4H-[1,2,4]oxadiazol-5-one
3-(2-Chloro-4-{1-[4-methyl-2-(4-trifluoromethyl-phenyl)-thiazol-5-yl]-3-phenyl-propoxy}-phenyl)-4H-[1,2,4]oxadiazol-5-one
3-(2-Chloro-4-{1-[4-methyl-2-(4-trifluoromethyl-phenyl)-oxazol-5-yl]-3-phenyl-propoxy}-phenyl)-4H-[1,2,4]oxadiazol-5-one
3-(2-Chloro-4-{2-(4-fluoro-phenyl)-1-[4-methyl-2-(4-trifluoromethyl-phenyl)-thiazol-5-yl]-ethoxy}-phenyl)-4H-[1,2,4]oxadiazol-5-one
3-(2-Chloro-4-{1-[4-methyl-2-(4-trifluoromethyl-phenyl)-thiazol-5-yl]-2-pyridin-2-yl-ethoxy}-phenyl)-4H-[1,2,4]oxadiazol-5-one
3-(2-Bromo-4-{1-[4-methyl-2-(4-trifluoromethyl-phenyl)-thiazol-5-yl]-propoxy}-phenyl)-4H-[1,2,4]oxadiazol-5-one
3-[4-{1-[4-Methyl-2-(4-trifluoromethyl-phenyl)-thiazol-5-yl]-propoxy}-2-(2,2,2-trifluoro-ethoxymethyl)-phenyl]-4H-[1,2,4]oxadiazol-5-one
3-(2-Methoxymethyl-4-{1-[4-methyl-2-(4-trifluoromethyl-phenyl)-thiazol-5-yl]-propoxy}-phenyl)-4H-[1,2,4]oxadiazol-5-one
3-(2-Ethoxymethyl-4-{1-[4-methyl-2-(4-trifluoromethyl-phenyl)-thiazol-5-yl]-propoxy}-phenyl)-4H-[1,2,4]oxadiazol-5-one
3-(2-Ethyl-4-{1-[4-methyl-2-(4-trifluoromethyl-phenyl)-thiazol-5-yl]-propoxy}-phenyl)-4H-[1,2,4]oxadiazol-5-one
3-(2-Cyclopropyl-4-{1-[4-methyl-2-(4-trifluoromethyl-phenyl)-thiazol-5-yl]-propoxy}-phenyl)-4H-[1,2,4]oxadiazol-5-one
3-(4-{1-[4-Methyl-2-(4-trifluoromethyl-phenyl)-thiazol-5-yl]-propoxy}-naphthalen-1-yl)-4H-[1,2,4]oxadiazol-5-one 3-(4-{1-[4-Methyl-2-(4-trifluoromethyl-phenyl)-thiazol-5-yl]-propoxy}-2-trifluoromethyl-phenyl)-4H-[1,2,4]oxadiazol-5-one 3-(4'-Fluoro-5-{1-[4-methyl-2-(4-trifluoromethyl-phenyl)-thiazol-5-yl]-propoxy}-biphenyl-2-yl)-4H-[1,2,4]oxadiazol-5-one 3-(2-Chloro-4-{2,2,2-trifluoro-1-[4-methyl-2-(4-trifluoromethyl-phenyl)-thiazol-5-yl]-ethoxy}-phenyl)-4H-[1,2,4]oxadiazol-5-one 3-(2-Chloro-4-{2,2-difluoro-1-[4-methyl-2-(4-trifluoromethyl-phenyl)-thiazol-5-yl]-butoxy}-phenyl)-4H-[1,2,4]oxadiazol-5-one 3-(2-Fluoro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one 3-(2-Cyclopropyl-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one 3-(8-{2,2,2-Trifluoro-1-[4-methyl-2-(4-trifluoromethyl-phenyl)-thiazol-5-yl]-ethoxymethyl}-quinolin-5-yl)-4H-[1,2,4]oxadiazol-5-one 3-(4-{2,2,2-Trifluoro-1-[4-methyl-2-(4-trifluoromethyl-phenyl)-thiazol-5-yl]-ethoxymethyl}-naphthalen-1-yl)-4H-[1,2,4]oxadiazol-5-one 3-(2-Chloro-6-{2,2,2-trifluoro-1-[4-methyl-2-(4-trifluoromethyl-phenyl)-thiazol-5-yl]-ethoxymethyl}-pyridin-3-yl)-4H-[1,2,4]oxadiazol-5-one 3-(2-Fluoro-4-{1-[4-methyl-2-(4-trifluoromethyl-phenyl)-thiazol-5-yl]-propoxymethyl}-phenyl)-4H-[1,2,4]oxadiazol-5-one 3-(4-{1-[4-Methyl-2-(4-trifluoromethyl-phenyl)-thiazol-5-yl]-propoxymethyl}-naphthalen-1-yl)-4H-[1,2,4]oxadiazol-5-one 3-(4-{1-[4-Methyl-2-(4-trifluoromethyl-phenyl)-thiazol-5-yl]-propoxymethyl}-phenyl)-4H-[1,2,4]oxadiazol-5-one 3-(4-{2,2-Difluoro-1-[4-methyl-2-(4-trifluoromethyl-phenyl)-thiazol-5-yl]-butoxymethyl}-phenyl)-4H-[1,2,4]oxadiazol-5-one 3-(4-{2-Cyclopropyl-2,2-difluoro-1-[4-methyl-2-(4-trifluoromethyl-phenyl)-thiazol-5-yl]-ethoxymethyl}-phenyl)-4H-[1,2,4]oxadiazol-5-one 3-(4-{2-(4-Difluoromethyl-phenyl)-2,2-difluoro-1-[4-methyl-2-(4-trifluoromethyl-phenyl)-thiazol-5-yl]-ethoxymethyl}-phenyl)-4H-[1,2,4]oxadiazol-5-one 3-(2-Fluoro-4-{2-[4-methyl-2-(4-trifluoromethyl-phenyl)-thiazol-5-yl]-hexyl}-phenyl)-4H-[1,2,4]oxadiazol-5-one 3-(2-Fluoro-4-{1-[4-methyl-2-(4-trifluoromethyl-phenyl)-thiazol-5-yl]-propoxy}-phenyl)-4H-1,2,4-oxadiazol-5-one 3-(2-Fluoro-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(2-Difluoromethoxy-4-{1-[4-methyl-2-(4-trifluoromethyl-phenyl)-thiazol-5-yl]-propoxy}-phenyl)-4H-1,2,4-oxadiazol-5-one 3-(2-Methoxy-4-{1-[4-methyl-2-(4-trifluoromethyl-phenyl)-thiazol-5-yl]-propoxy}-phenyl)-4H-1,2,4-oxadiazol-5-one 3-(2-Methoxy-4-{(R)-1-[4-methyl-2-(4-trifluoromethyl-phenyl)-thiazol-5-yl]-propoxy}-phenyl)-4H-1,2,4-oxadiazol-5-one 3-(2-Hydroxy-4-{1-[4-methyl-2-(4-trifluoromethyl-phenyl)-thiazol-5-yl]-propoxy}-phenyl)-4H-1,2,4-oxadiazol-5-one 3-(5-Fluoro-2-methoxy-4-{1-[4-methyl-2-(4-trifluoromethyl-phenyl)-thiazol-5-yl]-propoxy}-phenyl)-4H-1,2,4-oxadiazol-5-one 3-(5-Fluoro-2-methoxy-4-{(R)-1-[4-methyl-2-(4-trifluoromethyl-phenyl)-thiazol-5-yl]-propoxy}-phenyl)-4H-1,2,4-oxadiazol-5-one 3-(2-Difluoromethoxy-5-fluoro-4-{(R)-1-[4-methyl-2-(4-trifluoromethyl-phenyl)-thiazol-5-yl]-propoxy}-phenyl)-4H-1,2,4-oxadiazol-5-one 3-(2-Methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(5-Fluoro-2-methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(2-(2,2,2-Trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(2-Difluoromethoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(2-Difluoromethoxy-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-(2-Difluoromethoxy-5-fluoro-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one 3-[5-Fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one 3-[4-{1-[4-Methyl-2-(4-trifluoromethyl-phenyl)-thiazol-5-yl]-propoxy}-2-(2,2,2-trifluoro-ethoxy)-phenyl]-4H-1,2,4-oxadiazol-5-one 3-[4-{(R)-1-[4-Methyl-2-(4-trifluoromethyl-phenyl)-thiazol-5-yl]-propoxy}-2-(2,2,2-trifluoro-ethoxy)-phenyl]-4H-1,2,4-oxadiazol-5-one 3-(5-Fluoro-2-(2,2,2-trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one This invention also encompasses all combinations of preferred aspects of the invention described herein.

As used herein, the term alkyl is to be understood in the broadest sense to mean saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. The term "—(C0-C8)-alkyl" is a hydrocarbon residue containing 1, 2, 3, 4, 5, 6, 7 or 8 carbon atoms, in which the term "—C0-alkyl" is a covalent bond. All these statements apply also to the term alkylene.

As used herein, the term alkenyl is to be understood in the broadest sense to mean hydrocarbon residues which has 1 to 4 double bonds and can be linear, i.e. straight-chain, or branched. If not otherwise defined alkenyl has 2 to 8 carbon atoms. Examples of "—(C2-C8)-alkenyl" are alkenyl residues containing 2, 3, 4, 5, 6, 7 or 8 carbon atoms are, for example vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. All these statements apply also to the term alkenylene.

As used herein, the term alkynyl is to be understood in the broadest sense to mean hydrocarbon residues, which has 1 to 4 triple bonds and can be linear, i.e. straight-chain, or branched. If not otherwise defined alkynyl has 2 to 8 carbon atoms. Examples of "—(C2-C8)-alkynyl" are alkynyl residues containing 2, 3, 4, 5, 6, 7 or 8 carbon atoms are, for example ethynyl, 1-propynyl, 2-propynyl (=propargyl) or 2-butynyl. All these statements apply also to the term alkylidene.

All these statements also apply if an alkyl group occurs as a substituent on another residue, for example in an alkyloxy residue, an alkyloxycarbonyl residue or an arylalkyl residue.

If not otherwise defined, alkyl, alkylene, alkenyl, alkenylene, alkynyl and alkynylene are unsubstituted or mono, di- or tri-substituted independently of one another by suitable groups such as, for example: F, Cl, Br, 1, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C0-C4) alkylene-(C6-C10) aryl, CO—N((C0-C4) alkylene-H)—(C0-C4) alkylene-H, CO—N((C0-C4) alkylene-H)—(C0-C4) alkylene-(C3-C13)cycloalkyl, CO—N((C0-C4) alkylene-H)—(C0-C4) alkylene-(C3-C15) heterocycle, (C0-C4) alkylene-(C3-C6)cycloalkyl, (C0-C4) alkylene-(C6-C10)aryl, (C0-C4) alkylene-(C3-C15)heterocycle, (C2-C6)-alkenyl, (C2-C6)-alkynyl, O—(C0-C6)-alkyl, O—(C0-C4) alkylene-(C6-C10) aryl, O—(C0-C4) alkylene-(C3-C12)cycloalkyl, O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4)alkyl, SO—(C0-C4) alkylene-(C3-C13)cycloalkyl, SO—(C0-C4) alkylene-(C6-C10) aryl, SO—(C0-C4) alkylene-(C3-C15) heterocycle, SO2—(C1-C4)alkyl, SO2—(C0-C4) alkylene-(C3-C13)cycloalkyl, SO2—(C0-C4) alkylene-(C6-C10) aryl, SO2—(C0-C4) alkylene-(C3-C15) heterocycle, SO2—N((CO—C4)alkylene-H)—(C0-C4)alkylene-(C6-C10)aryl, SO2—N((C0-C4)alkylene-H)—(CO—C4)alkylene-H, SO2—N((C0-C4) alkylene-H)—(C0-C4)alkylene-(C3-C13) cycloalkyl, SO2—N((C0-C4)alkylene-H)—(C0-C4)alkylene-(C3-C15)heterocycle where the aryl ring or heterocyclic ring is unsubstituted or mono- or di-substituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H;

N((C0-C4)-alkylene-H)—(C0-C4)-alkylene-H, N((C0-C4) alkylene-H)—(C0-C4)alkylene-H)—(C1-C6)cycloalkyl, N((C0-C4)alkylene-H)—(C0-C4)alkylene-(C6-C12)-aryl, N((CO—C4)alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((CO—C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4) alkylene-H)—CO—O—(CO—C4)alkylene-(C6-C12)-aryl, N((C0-C4)alkylene-H)—CO—O—(C0-C4)alkyl, N((CO—C4) alkylene-H)—CO—O—(C0-C4)alkylene-(C3-C13) cycloalkyl, N((C0-C4)alkylene-H)—CO—O—(C0-C4) alkylene-(C3-C15)heterocycle, N((C0-C4) alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(CO—C4)alkylene-(C3-C13)cycloalkyl, N((C0-C4)alkylene-H)—CO—N((C0-C4)-alkylene-H)—(C0-C4)alkylene-(C3-C15)heterocycle, where the aryl ring or heterocyclic ring is unsubstituted or mono- or di-substituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2—CH3, COOH, COO—(C1-C6)-alkyl, SF5, CONH2.

The term cycloalkyl is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11,12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

The term cycloalkenyl is to be understood to mean unsaturated hydrocarbon cycle containing from 3 to 8 carbon atoms in a mono- or bicyclic, fused or bridged ring, wherein the one, two or three double bonds are not located within a cyclic alkyl group in such a manner that an aromatic system results. Examples of unsaturated cycloalkenyl groups are cyclopentenyl or cyclohexenyl, which can be bonded via any carbon atom. The term cycloalkenyl also includes bicyclic groups in which any of the above cycloalkenyl ring is fused to a benzene ring, for example 1,2-dihydronaphthalene, 1,4-dihydronaphthalene and 1H-indene.

If not otherwise defined cycloalkyl or cycloalkenyl are unsubstituted or mono, di- or tri-substituted independently of one another by suitable groups such as, for example: F, Cl, Br, 1, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C1-C6) alkylene-H, CO—N((C0-C4) alkylene-H)—(C1-C6) cycloalkyl, CON((C0-C4) alkylene-H)—(C0-C4)alkylene-(C6-C12)-aryl, (C0-C4) alkylene-(C3-C6)cycloalkyl, (C3-C6)alkyl, (C2-C6)-alkenyl, (C2-C6)-alkynyl, (C0-C4) alkylene-(C6-C10)aryl, (C0-C4) alkylene-(C3-C15)heterocycle, O—(C0-C6)-alkyl, (C0-C4) alkylene-O—(C0-C4) alkyl, (C0-C4) alkylene-O—(C0-C4) alkylene-(C3-C13)cycloalkyl, (C0-C4) alkylene-O—(C0-C4) alkylene-(C6-C10) aryl, (C0-C4) alkylene-O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, O—CO—N((C0-C4) alkylene-H)—(C0-C4) alkylene-(C6-C10) aryl, O—CO—N((C0-C4) alkylene-H)—(C0-C4) alkylene-H, O—CO—N((C0-C4) alkylene-H)—(C0-C4) alkylene-(C3-C13)cycloalkyl, O—CO—N((C0-C4) alkylene-H)—(C0-C4) alkylene-(C3-C15) heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4) alkyl, SO—(C0-C4) alkylene-(C3-C13)cycloalkyl, SO—(C0-C4) alkylene-(C6-C10) aryl, SO—(C0-C4) alkylene-(C3-C15) heterocycle, SO2—(C1-C4)alkyl, SO2—(C0-C4) alkylene-(C3-C13)cycloalkyl, SO2—(C0-C4) alkylene-(C6-C10) aryl, SO2—(C0-C4) alkylene-(C3-C15) heterocycle, SO2—N((C0-C4)alkylene-H)—(CO—C4)alkylene-(C6-C10)aryl, SO2—N((C0-C4)alkylene-H)—(C0-C4)alkylene-H, SO2—N((C0-C4) alkylene-H)—(C0-C4)alkylene-(C3-C13)cycloalkyl, SO2—N((C0-C4)alkylene-H)—(C0-C4) alkylene-(C3-C15)heterocycle, where the aryl ring or heterocyclic ring is unsubstituted or mono- or di-substituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H;

N((C0-C4)-alkylene-H)—(C0-C4)-alkylene-H, N((C0-C4) alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4) alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4) alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or di-substituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2—CH3, COOH, COO—(C1-C6)-alkyl, SF5, CONH2.

The term "aryl" is understood to mean aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenyl, for example 2-biphenyl, 3-biphenyl and 4-biphenyl, anthryl or fluorenyl. Biphenyl rings, naphthyl ring and, in particular, phenyl ring are further embodiments of aryl ring.

The terms heterocycle is understood to mean saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclicring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2, 3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or tri-substituted by suitable groups such as, for example: F, Cl, Br, I, CF3, NO2, CN, COOH, CO—O—(C0-C4) alkylene-(C6-C10) aryl, CO—O—(C1-C4) alkyl, CO—O—(C0-C4) alkylene-(C3-C13)cycloalkyl, CO—O—(C0-C4) alkylene-(C3-C15)heterocycle, CO—N((C0-C4) alkylene-H)—(C1-C6)alkylene-H, CO—N((C0-C4) alkylene-H)—(C1-C6)cycloalkyl, CON((C0-C4) alkylene-H)—(C0-C4)alkylene-(C6-C12)-aryl, (C0-C4) alkylene-(C3-C6)cycloalkyl, (C3-C6)alkyl, (C2-C6)-alkenyl, (C2-C6)-alkynyl, (C0-C4)alkylene-(C6-C10)aryl, (C0-C4) alkylene-(C3-C15)heterocycle, O—(C0-C6)-alkyl, (C0-C4) alkylene-O—(C0-C4) alkyl, (C0-C4) alkylene-O—(C0-C4) alkylene-(C3-C13)cycloalkyl, (C0-C4) alkylene-O—(C0-C4) alkylene-(C6-C10) aryl, (C0-C4) alkylene-O—(C0-C4) alkylene-(C3-C15)heterocycle, O—CO—O—(C0-C4) alkylene-(C6-C10) aryl, O—CO—O—(C1-C4) alkyl, O—CO—O—(C0-C4) alkylene-(C3-C13)cycloalkyl, O—CO—O—(C0-C4) alkylene-(C3-C15)heterocycle, O—CO—N((C0-C4) alkylene-H)—(C0-C4) alkylene-(C6-C10) aryl, O—CO—N((C0-C4) alkylene-H)—(C0-C4) alkylene-H, O—CO—N((C0-C4) alkylene-H)—(C0-C4) alkylene-(C3-C13)cycloalkyl, O—CO—N((C0-C4) alkylene-H)—(C0-C4) alkylene-(C3-C15) heterocycle, S—(C1-C4)alkyl, S—(C0-C4) alkylene-(C3-C13)cycloalkyl, S—(C0-C4) alkylene-(C6-C10) aryl, S—(C0-C4) alkylene-(C3-C15) heterocycle, SO—(C1-C4) alkyl, SO—(C0-C4) alkylene-(C3-C13)cycloalkyl, SO—(C0-C4) alkylene-(C6-C10) aryl, SO—(C0-C4) alkylene-(C3-C15) heterocycle, SO2—(C1-C4)alkyl, SO2—(C0-C4) alkylene-(C3-C13)cycloalkyl, SO2—(C0-C4) alkylene-(C6-C10) aryl, SO2—(C0-C4) alkylene-(C3-C15) heterocycle, SO2—N((C0-C4)alkylene-H)—(C0-C4)alkylene-(C6-C10) aryl, SO2—N((CO—C4)alkylene-H)—(C0-C4)alkylene-H, SO2—N((C0-C4) alkylene-H)—(C0-C4)alkylene-(C3-C13) cycloalkyl, SO2—N((C0-C4)alkylene-H)—(C0-C4)alkylene-(C3-C15)heterocycle, where the aryl ring or heterocyclic ring is unsubstituted or mono- or di-substituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H,;

N((C0-C4)-alkylene-H)—(C0-C4)-alkylene-H, N((C0-C4) alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4) alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4) alkylene-H)—CO—O—(C0-C4)alkylene-(C6-C12)-aryl, N((C0-C4)

alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4) alkylene-H)—CO—N((C0-C4)-alkylene-H)—(C0-C4)alkylene-(C6-C12)-aryl, N((C0-C4)alkylene-H)—CO—N((C0-C4)-alkylene-H)—(CO—C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or di-substituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2—CH3, COOH, COO—(C1-C6)-alkyl, SF5, CONH2.

The term "R5 and R6 together with the nitrogen atom to which they are bonded (Y=N(R6)) can form a (C3-C9)-heterocycle which for example can contain additionally 1 to 3 heteroatoms" refer to structures of heterocycles which can be derived from compounds such as for example pyrrolidine, morpholine, thiomorpholine, piperidine, piperazine, azetidine, 2,3-dihydro-1H-isoindole, piperazin-2-one, azetidine, isoindoline, 2,5-diazabicyclo[2.2.1]heptane, thiomorpholine 1-oxide, thiomorpholine 1,1-dioxide, piperidin-4-one, piperidin-3-one, homopiperidine, homopiperazine, homomorpholine, 2,3,6,7-tetrahydro-(1H)-1,4-diazepin-5(4H)-one, 4-oxazolidine, azetidin-3-one, thiazolidine, thiazolidine 1-oxide, thiazolidine 1,1-dioxide, 4-imidazolidinone, 5,6,7,8-tetrahydro-[1,2,4]triazolo[4,3-a]pyrazine, 1,4-diazabicyclo[4.3.0]nonane, 2-aza-5-oxabicyclo[2.2.1]heptane, 2-oxa-5-azabicyclo[2.2.1]heptane, diazabicyclo[4.4.0]decane, 4,5,6,7-tetrahydrothieno[3,2-c]pyridine, 4,5,6,7-tetrahydro-1H-imidazol[4,5-c]-pyridine, 4,5,6,7-tetrahydro-1H-pyrazolo[4,3-c]pyridine, 3,8-diaza-bicyclo[3.2.1]octane, octahydropyrrolo[3,4-c]pyrrole, 2,5-diazabicyclo[2.2.2]octane, 4-spiro-[3-(N-methyl-2-pyrrolidinone)]-piperidine, 2,8-diaza-spiro[5.5]undecane, 2,7-diaza-spiro[4.4]nonane, 3,9-diaza-spiro[5.5]undecane, 2,8-diaza-spiro[4.5]decane, 2,7-diaza-spiro[3.5]nonane, 2,9-diaza-spiro[5.5]undecane, 2,7-diaza-spiro[4.5]decane, 1-oxa-4,9-diaza-spiro[5.5]undecane, 1-oxa-4,8-diaza-spiro[5.5]undecane.

The term "R2 and R3 together with the C-atoms to which they are bonded form a (C6-C10) aryl- or a (C5-C10) heteroaryl ring"

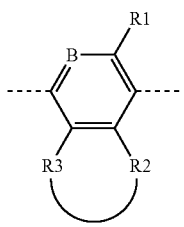

refer to structures of bicyclic aromatic or heteroaryl rings which comprise 10 to 14 (aryl) or 9 to 14 (heteroaryl) ring atoms in total.

The term "oxo-residue" or "=O" refers to residues such as carbonyl (—CO—), nitroso (—N=O), sulfinyl (—SO—) or sulfonyl (—SO$_2$—).

Halogen is fluorine, chlorine, bromine or iodine.

Optically active carbon atoms present in the compounds of formula I can independently of each other have R configuration or S configuration. The compounds of formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of formula I and it comprises all ratios of the stereoisomers in the mixtures. In case the compounds of formula I can be present as E isomers or Z isomers (or cis isomers or trans isomers) the invention relates both to pure E isomers and pure Z isomers and to E/Z mixtures in all ratios. The invention also comprises all tautomeric forms of the compounds of formula i.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of formula I can also be obtained by employing stereochemically uniform starting materials or by using stereoselective reactions.

The compounds of formula I may exist in the form of their racemates, racemic mixtures, pure enantiomers, diastereomers and mixtures of diastereomers as well in their tautomeric forms. The present invention encompasses all these isomeric and tautomeric forms of the compounds of formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of formula I of the invention, for example an ester, which on administration to a mammal such as, for example, a human is able to form (directly or indirectly) a compound of formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of formula I as described above, and their salts, solvates and physiologically functional derivatives as described herein.

Use

This invention relates further to the use of compounds of formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPARgamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5361). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang, Y-X. et al., Cell, 2003, 113, 159-170; Luquet, S. et al., FASEB J., 2003, 17, 209-226; Tanaka, T. et al., PNAS, 2003, 100, 15924-15929; Hoist, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457). Besides its actions as a regulator of the lipid-, glucose- and cholesterol-metabolism PPARdelta is known to play a role in embryonic development, implantation and bone formation (Lim, H. and Dey, S. K., Trends Endocrin Metab., 2000, 11(4), 137-42; Ding, N. Z. et al., Mol Reprod Dev., 2003, 66(3), 218-24; Mano, H. et al., J Biol. Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol. Biol., 2003, 85(2-5), 257-65; Tan, N. S. et al., Am J Clin Dermatol., 2003, 4(8), 523-30; Wahli, W., Swiss Med. Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299,1437,1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury. The present invention relates to compounds of formula I suitable for modulating the activity of PPARs, especially the activity of PPARdelta and PPARalpha. Depending on the modulation profile, the compounds of formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:

1. Disorders of fatty acid metabolism and glucose utilization disorders.
   Disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Disorders or conditions in which inflammatory reactions are involved:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   asthma
   lupus erythematosus (LE) or inflammatory rheumatic disorders such as, for example, rheumatoid arthritis
   other inflammatory states
6. Disorders of cell cycle or cell differentiation processes:
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
7. Demyelinating and other neurodegenerative disorders of the central and peripheral nervous systems including:
   Alzheimer's disease
   multiple sclerosis
   Parkinson's disease
   adrenoleukodystrophy (ALD)
   adrenomyeloneuropathy
   AIDS-vacuolar myelopathy
   HTLV-associated myelopathy
   Leber's hereditary optic atrophy
   progressive multifocal leukoencephalopathy (PML)
   subacute sclerosing panencephalitis
   Guillian-Barre syndrome
   tropical spastic paraparesis
   acute disseminated encephalomyelitis (ADEM)
   acute viral encephalitis
   acute transverse myelitis
   spinal cord and brain trauma
   Charcot-Marie-Tooth disease
8. Skin disorders and/or disorders of wound healing processes:
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   wound healing
9. Other disorders
   high blood pressure
   pancreatitis
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 368 (1986).

The compounds of formula I are distinguished by favorable effects on metabolic disorders. They beneficially influence lipid and sugar metabolism, in particular they lower the triglyceride level and are suitable for the prevention and treatment of type II diabetes and atherosclerosis and the diverse sequalae thereof.

Combinations with Other Medicaments

The compounds of the invention can be administered alone or in combination with one or more further pharmacologically active substances. In particular, the compounds of the invention can be administered in combination with active ingredients having a similar pharmacological action. For example, they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments, 4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of disorders of the central nervous system
13. active ingredients for the treatment of drug, nicotine and alcohol addiction
14. analgesics They can be combined with the compounds of the invention of formula I in particular for a synergistic enhancement of activity. Administration of the active ingredient combination can take place either by separate administration of the active ingredients to the patient or in the form of combination products in which a plurality of active ingredients are present in one pharmaceutical preparation.

Particularly suitable further active ingredients for the combination preparations are: All antidiabetics mentioned in the Rote Liste 2006, Chapter 12; all slimming agents/appetite suppressants mentioned in the Rote Liste 2006, Chapter 1; all lipid-lowering agents mentioned in the Rote Liste 2006, Chapter 58. They can be combined with the compound of formula I according to the invention in particular for a synergistic enhancement of activity. The active compound combination can be administered either by separate administration of the active compounds to the patient or in the form of combination preparations in which a plurality of active compounds are present in a pharmaceutical preparation. Most of the active compounds listed below are disclosed in USP Dictionary of USAN and International Drug Names, US Pharmacopeia, Rockville 2001.

Antidiabetics include insulin and insulin derivatives, such as, for example, Lantus® (see www.lantus.com) or HMR 1964 or those described in WO2005005477 (Novo Nordisk), fast-acting insulins (see U.S. Pat. No. 6,221,633), inhalable insulins, such as, for example, Exubera® or oral insulins, such as, for example, IN-105 (Nobex) or Oral-lyn™ (Generex Biotechnology), GLP-1 derivatives, such as, for example, Exenatide, Liraglutide or those disclosed in WO 98/08871 or WO2005027978 by Novo Nordisk A/S, in WO 01/04156 by Zealand or in WO 00/34331 by Beaufour-Ipsen, pramlintide acetate (Symlin; Amylin Pharmaceuticals), and also orally effective hypoglycemic active ingredients.

The active compounds preferably include
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of the glucose transporter 4 (GLUT4),
inhibitors of glutamine:fructose-6-phosphate amidotransferase (GFAT), GLP-1 agonists,
potassium channel openers, such as, for example, those disclosed in WO 97/26265 and WO 99/03861 by Novo Nordisk A/S,
inhibitors of dipeptidylpeptidase IV (DPP-IV),
insulin sensitizers,
inhibitors of liver enzymes involved in the stimulation of gluconeogenesis and/or glycogenolysis,
modulators of glucose uptake, glucose transport and glucose back resorption,
inhibitors of 11β-HSD1,
inhibitors of protein tyrosine phosphatase 1B (PTP1B),
modulators of the sodium/glucose cotransporter 1 or 2 (SGLT1, SGLT2),
compounds which alter lipid metabolism, such as antihyperlipidemic active ingredients and antilipidemic active ingredients,
compounds which reduce food intake or food absorption,
compounds which increase thermogenesis,
PPAR and RXR modulators and
active ingredients which act on the ATP-dependent potassium channel of the beta cells.

In one embodiment of the invention, the compound of formula I is administered in combination with a HMGCoA reductase inhibitor, such as simvastatin, fluvastatin, pravastatin, lovastatin, atorvastatin, cerivastatin, rosuvastatin or L-659699.

In one embodiment of the invention, the compound of formula I is administered in combination with a cholesterol resorption inhibitor, such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, the compound of formula I is administered in combination with a PPAR gamma agonist, such as, for example, rosiglitazone, pioglitazone, JTT-501, GI 262570, R-483 or CS-011 (rivoglitazone).

In one embodiment of the invention, the compound of formula I is administered in combination with a PPAR alpha agonist, such as, for example, GW9578, GW-590735, K-111, LY-674, KRP-101 or DRF-10945.

In one embodiment of the invention, the compound of formula I is administered in combination with a mixed PPAR alpha/gamma agonist, such as, for example, muraglitazar, tesaglitazar, naveglitazar, LY-510929, ONO-5129, E-3030 or as described in WO0/64888, WO0/64876, WO03/020269, WO2004075891, WO2004076402, WO2004075815, WO2004076447, WO2004076428, WO2004076401, WO2004076426, WO2004076427, WO2006018118, WO2006018115, and WO2006018116 or in J. P. Berger et al., TRENDS in Pharmacological Sciences 28(5), 244-251, 2005.

In one embodiment of the invention, the compound of formula I is administered in combination with a PPAR delta agonist, such as, for example, GW-501516 or as described in WO2005097762, WO2005097786, WO2005097763, and WO2006029699.

In one embodiment of the invention, the compound of formula I is administered in combination with metaglidasen or with MBX-2044 or other partial PPAR gamma agonists/antagonists.

In one embodiment of the invention, the compound of formula I is administered in combination with a fibrate, such as, for example, fenofibrate, clofibrate or bezafibrate.

In one embodiment of the invention, the compound of formula I is administered in combination with an MTP inhibitor, such as, for example, implitapide, BMS-201038, R-103757 or those described in WO2005085226.

In one embodiment of the invention, the compound of formula I is administered in combination with a CETP inhibitor, such as, for example, torcetrapib or JTT-705.

In one embodiment of the invention, the compound of formula I is administered in combination with a bile acid resorption inhibitor (see, for example, U.S. Pat. Nos. 6,245, 744, 6,221,897 or WO00/61568), such as, for example, HMR 1741 or those described in DE 10 2005 033099.1 and DE 10 2005 033100.9.

In one embodiment of the invention, the compound of formula I is administered in combination with a polymeric bile acid adsorber, such as, for example, cholestyramine or colesevelam.

In one embodiment of the invention, the compound of formula I is administered in combination with an LDL receptor inducer (see U.S. Pat. No. 6,342,512), such as, for example, HMR1171, HMR1586 or those described in WO2005097738.

In one embodiment, the compound of formula I is administered in combination with Omacor® (omega-3 fatty acids; highly concentrated ethyl esters of eicosapentaenoic acid and docosahexaenoic acid).

In one embodiment of the invention, the compound of formula I is administered in combination with an ACAT inhibitor, such as, for example, avasimibe.

In one embodiment of the invention, the compound of formula I is administered in combination with an antioxidant, such as, for example, OPC-14117, probucol, tocopherol, ascorbic acid, β-carotene or selenium.

In one embodiment of the invention, the compound of formula I is administered in combination with a vitamin, such as, for example, vitamin B6 or vitamin B12.

In one embodiment of the invention, the compound of formula I is administered in combination with a lipoprotein lipase modulator, such as, for example, ibrolipim (NO-1886).

In one embodiment of the invention, the compound of formula I is administered in combination with an ATP-citrate lyase inhibitor, such as, for example, SB-204990.

In one embodiment of the invention, the compound of formula I is administered in combination with a squalene synthetase inhibitor, such as, for example, BMS-188494 or as described in WO2005077907.

In one embodiment of the invention, the compound of formula I is administered in combination with a lipoprotein (a) antagonist, such as, for example, gemcabene (Cl-1027).

In one embodiment of the invention, the compound of formula I is administered in combination with an HM74A receptor agonists, such as, for example, nicotinic acid.

In one embodiment of the invention, the compound of formula I is administered in combination with a lipase inhibitor, such as, for example, orlistat or cetilistat (ATL-962).

In one embodiment of the invention, the compound of formula I is administered in combination with insulin.

In one embodiment of the invention, the compound of formula I is administered in combination with a sulfonylurea, such as, for example, tolbutamide, glibenclamide, glipizide or glimepiride.

In one embodiment of the invention, the compound of formula I is administered in combination with a biguanide, such as, for example, metformin.

In another embodiment of the invention, the compound of formula I is administered in combination with a meglitinide, such as, for example, repaglinide or nateglinide.

In one embodiment of the invention, the compound of formula I is administered in combination with a thiazolidinedione, such as, for example, troglitazone, ciglitazone, pioglitazone, rosiglitazone or the compounds disclosed in WO 97/41097 by Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of formula I is administered in combination with an α-glucosidase inhibitor, such as, for example, miglitol or acarbose.

In one embodiment of the invention, the compound of formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of formula I is administered in combination with more than one of the compounds mentioned above, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of formula I is administered in combination with an inhibitor of glycogen phosphorylase, such as, for example, PSN-357 or FR-258900 or those described in WO2003084922, WO2004007455, WO2005073229-31 or WO2005067932.

In one embodiment of the invention, the compound of formula I is administered in combination with glucagon receptor antagonists, such as, for example, A-770077, NNC-25-2504 or such as in WO2004100875 or WO2005065680.

In one embodiment of the invention, the compound of formula I is administered in combination with activators of glucokinase, such as, for example, RO-4389620, LY-2121260 (WO2004063179), PSN-105, PSN-110, GKA-50 or those described, for example, by Prosidion in WO2004072031, WO2004072066, WO 05103021 or WO 06016178, by Roche in WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, US 04067939 or WO 04052869, by Novo Nordisk in EP 1532980, WO 03055482, WO 04002481, WO 05049019, WO 05066145 or WO 05123132, by Merck/Banyu in WO 03080585, WO03097824, WO 04081001, WO 05063738 or WO 05090332, by Eli Lilly in WO 04063194, or by Astra Zeneca in WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment of the invention, the compound of formula I is administered in combination with an inhibitor of gluconeogenesis, such as, for example, FR-225654.

In one embodiment of the invention, the compound of formula I is administered in combination with inhibitors of fructose-1,6-bisphosphatase (FBPase), such as, for example, CS-917.

In one embodiment of the invention, the compound of formula I is administered in combination with modulators of the glucose transporter 4 (GLUT4), such as, for example, KST-48 (D.-O. Lee et al.: Arzneim.-Forsch. Drug Res. 54 (12), 835 (2004)).

In one embodiment of the invention, the compound of formula I is administered in combination with inhibitors of glutamine:fructose-6-phosphate amidotransferase (GFAT), as described, for example, in WO2004101528.

In one embodiment of the invention, the compound of formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964× or as described in WO2003074500, WO2003106456, WO200450658, WO2005058901, WO2005012312, WO2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of formula I is administered in combination with inhibitors of 11-beta-hydroxysteroid dehydrogenase-1 (11β-HSD1), such as, for example, BVT-2733 or those described, for example, in WO200190090-94, WO200343999, WO20041-12782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment of the invention, the compound of formula I is administered in combination with inhibitors of protein tyrosine phosphatase 1B (PTP1B), as described, for example, in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment of the invention, the compound of formula I is administered in combination with modulators of the sodium/glucose cotransporter 1 or 2 (SGLT1, SGLT2), such as, for example, KGA-2727, T-1095 and SGL-0010 or as described, for example, in WO2004007517, WO200452903, WO200452902, WO2005121161, WO2005085237, JP2004359630 or by A. L. Handlon in Expert Opin. Ther. Patents (2005) 15(11), 1531-1540.

In one embodiment of the invention, the compound of formula I is administered in combination with inhibitors of hormone-sensitive lipase (HSL), such as those described, for example, in WO01/17981, WO01/66531, WO2004035550, WO2005073199 or WO03/051842.

In one embodiment of the invention, the compound of formula I is administered in combination with inhibitors of acetyl-CoA carboxylase (ACC) such as those described, for example, in WO199946262, WO200372197, WO2003072197 or WO2005044814.

In one embodiment of the invention, the compound of formula I is administered in combination with an inhibitor of phosphoenolpyruvate carboxykinase (PEPCK), such as those described, for example, in WO2004074288.

In one embodiment of the invention, the compound of formula I is administered in combination with an inhibitor of glycogen synthase kinase-3 beta (GSK-3 beta), such as those described, for example, in US2005222220, WO2004046117, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment of the invention, the compound of formula I is administered in combination with an inhibitor of protein kinase C beta (PKC beta), such as, for example, ruboxistaurin.

In one embodiment of the invention, the compound of formula I is administered in combination with an endothelin-A receptor antagonist, such as, for example, avosentan (SPP-301).

In one embodiment of the invention, the compound of formula I is administered in combination with inhibitors of "I-kappaB kinase" (IKK inhibitors), such as those described, for example, in WO2001000610, WO2001030774, WO2004022553 or WO2005097129.

In one embodiment of the invention, the compound of formula I is administered in combination with modulators of the glucocorticoid receptor as described, for example, in WO2005090336.

In a further embodiment of the invention, the compound of formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, {4-[(4-aminoquinazolin-2-ylamino)methyl]-cyclohexylmethyl}naphthalene-1-sulfonamide hydrochloride (CGP 71683A);

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those described in WO2005080424;

cannabinoid receptor 1 antagonists, such as, for example, rimonabant, SR147778 or those described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897;

MC4 agonists (for example [2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydro-naphthalene-2-carboxamide; (WO 01/91752)) or LB53280, LB53279, LB53278 or THIQ, MB243, RY764, CHIR-785, PT-141 or those described in WO2005060985, WO2005079950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077 or WO2006024390;

orexin receptor antagonists (for example 1-(2-methylbenzoxazol-6-yl)-3-[1,5]naphthyridin-4-ylurea hydrochloride (SB-334867-A) or those described, for example, in WO200196302, WO200185693, WO2004085403 or WO2005075458); histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208) or those described in WO200064884, WO2005082893); CRF antagonists (for example [2-methyl-9-(2,4,6-trimethylphenyl)-9H-1,3,9-triazafluoren-4-yl]dipropylamine (WO 00/66585)); CRF BP antagonists (for example urocortin); urocortin agonists;

β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or those compounds described in WO2003/15769, WO2005085200, WO2005019240, WO2004011438, WO2004012648, WO2003015769, WO2004072025, WO2005070898, WO2005070925, WO2006018280, WO2006018279, WO2004039780, WO2003033476, WO2002006245, WO2002002744, WO2003004027 or FR2868780);

CCK-A agonists (such as, for example, {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (for example dexfenfluramine);

mixed serotonin- and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, APD-356, BVT-933 or those described in WO200077010, WO20077001-02, WO2005019180, WO2003064423, WO200242304 or WO2005082859);

5-HT6 receptor antagonists, such as described, for example, in WO2005058858;

bombesin receptor agonists (BRS-3 agonists);

galanin receptor antagonists;

growth hormone (for example human growth hormone or AOD-9604);

growth hormone releasing compounds (tert-butyl 6-benzyloxy-1-(2-diisopropylamino-ethylcarbamoyl)-3,4-dihydro-1H-isoquinoline-2-carboxylate (WO 01/85695));

growth hormone secretagog receptor antagonists (ghrelin antagonists) such as, for example, A-778193 or those described in WO2005030734;

TRH agonists (see, for example, EP 0 462 884);

uncoupling protein 2 or 3 modulators;

leptin agonists (see for example Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (as described, for example, in WO 00/40569);

inhibitors of diacylglycerol O-acyltransferases (DGATs) such as described, for example, in US2004/0224997, WO2004094618, WO200058491, WO2005044250, WO2005072740, JP2005206492 or WO2005013907;

inhibitors of fatty acid synthase (FAS) such as, for example, C75 or those described in WO2004005277;

oxyntomodulin;

oleoyl-estrone or thyroid hormone receptor agonists, such as, for example, KB-2115 or those described in WO20058279, WO200172692, WO200194293, WO2003084915, WO2004018421 or WO2005092316.

In one embodiment of the invention, the further active ingredient is leptin; see for example "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine.

In one embodiment of the invention, the further active ingredient is mazindol or phentermine.

In one embodiment, the compounds of formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of formula I and Caromax®. Caromax® can in this connection also be administered in the form of food products such as, for example, in bakery products or muesli bars.

In one embodiment of the invention, the compound of formula I is administered in combination with PDE (phosphodiesterase) inhibitors, as described, for example, in WO2003/077949 or WO2005012485.

In one embodiment of the invention, the compound of formula I is administered in combination with NAR-1 (nicotinic acid receptor) agonists as described, for example, in WO2004094429.

In one embodiment of the invention, the compound of formula I is administered in combination with CB2 (cannabinoid receptor) agonists as described, for example, in US2005/143448.

In one embodiment of the invention, the compound of formula I is administered in combination with histamine 1 agonists as described, for example, in WO2005101979.

In one embodiment of the invention, the compound of formula I is administered in combination with bupropion, as described in WO2006017504.

In one embodiment of the invention, the compound of formula I is administered in combination with opioid antagonists as described, for example, in WO2005107806 or WO2004094429.

In one embodiment of the invention, the compound of formula I is administered in combination with neutral endopeptidase inhibitors as described, for example, in WO200202513, WO2002/06492, WO 2002040008, WO2002040022 or WO2002047670.

In one embodiment of the invention, the compound of formula I is administered in combination with NPY inhibitors (neuropeptide Y) as described, for example, in WO2002047670.

In one embodiment of the invention, the compound of formula I is administered in combination with sodium/hydrogen exchange inhibitors as described, for example, in WO2003092694.

In one embodiment of the invention, the compound of formula I is administered in combination with modulators of the glucocorticoid receptor as described, for example, in WO2005090336.

In one embodiment of the invention, the compound of formula I is administered in combination with nicotine receptor agonists as described, for example, in WO2004094429.

In one embodiment of the invention, the compound of formula I is administered in combination with NR is (norepinephrine reuptake inhibitors) as described, for example, in WO2002053140.

In one embodiment of the invention, the compound of formula I is administered in combination with MOA (E-beta-methoxyacrylate), such as, for example, segeline, or as described, for example, in WO2002053140.

In one embodiment of the invention, the compound of formula I is administered in combination with antithrombotic active ingredients, such as, for example, clopidogrel. It is to be understood that each suitable combination of the compounds according to the invention with one or more of the compounds mentioned above and optionally one or more further pharmacologically active substances is meant to be included in the scope of the present invention. It will be appreciated that every suitable combination of the compounds of the invention with one or more of the aforementioned compounds and optionally one or more other pharmacologically active substances is regarded as falling within the protection conferred by the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow. Moreover, in the experimental descriptions and examples below, a number of abbreviations are used therein which may be defined as follows:

The formulae for some of the development codes mentioned above are given below.

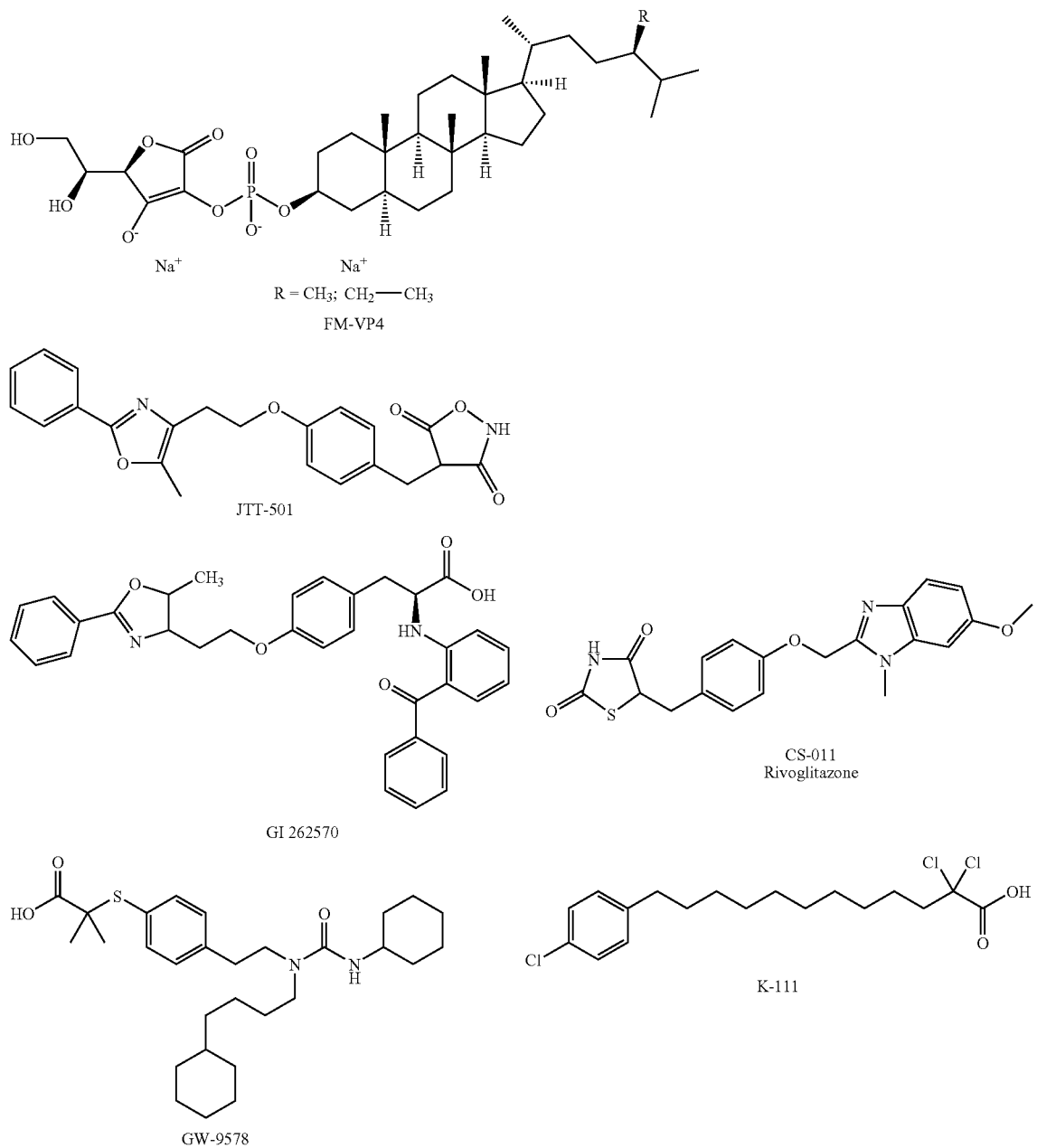

-continued
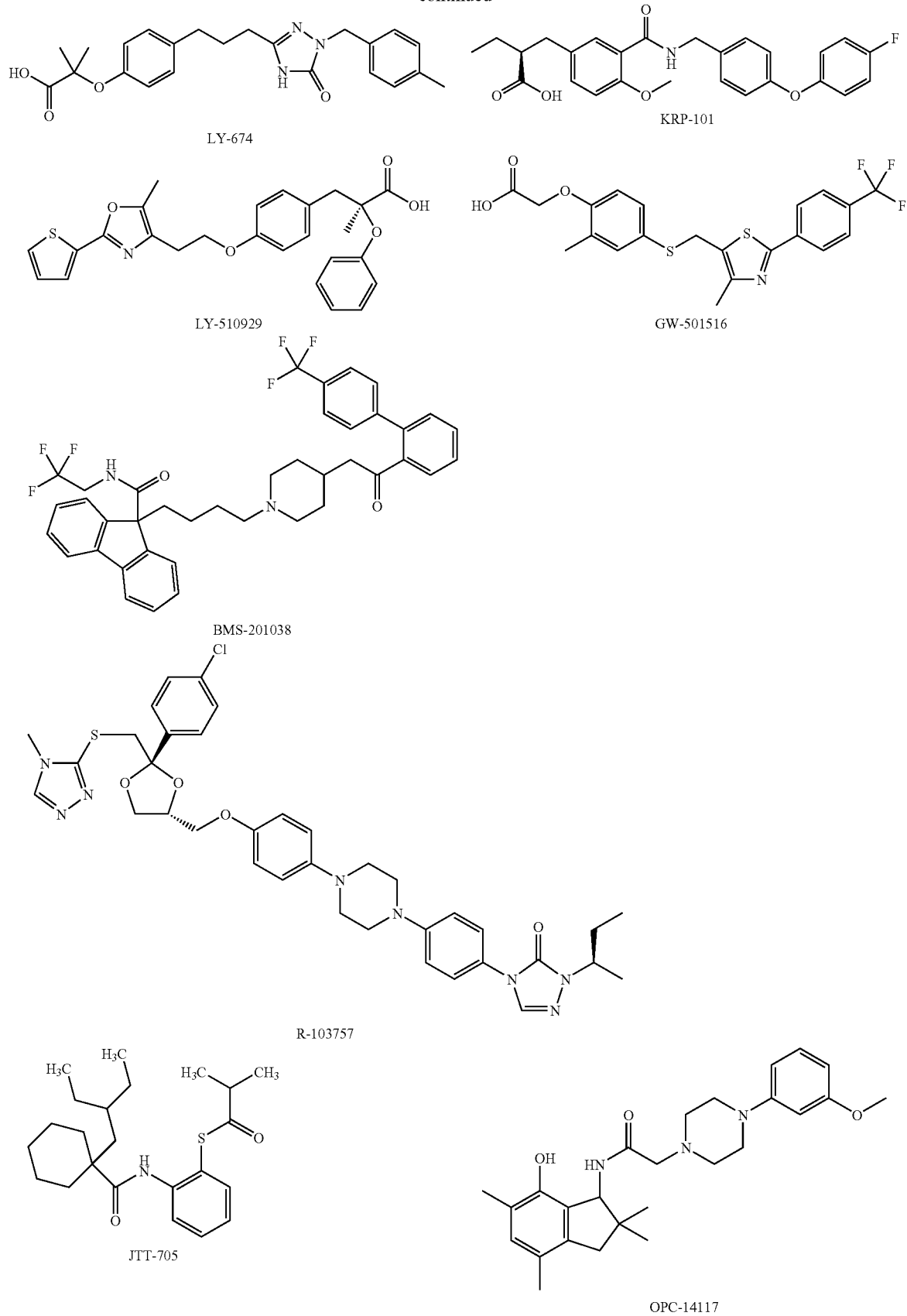

-continued
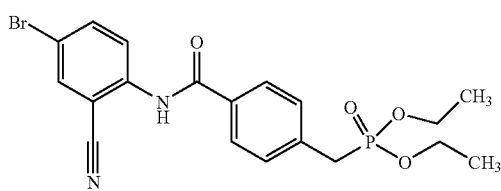
NO-1886
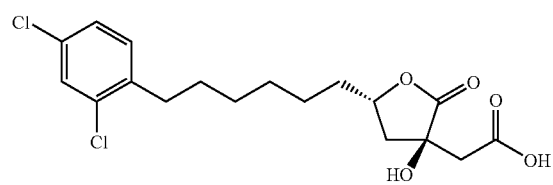
SB-204990
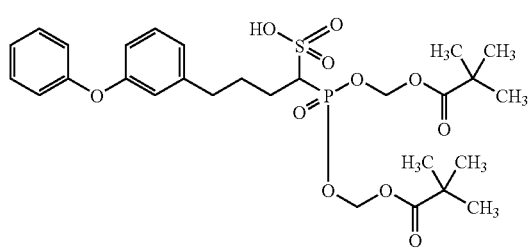
BMS-188494
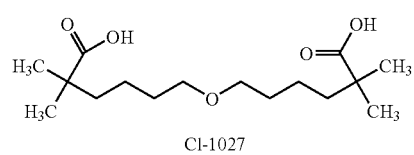
Cl-1027
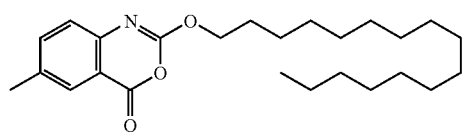
ATL-962
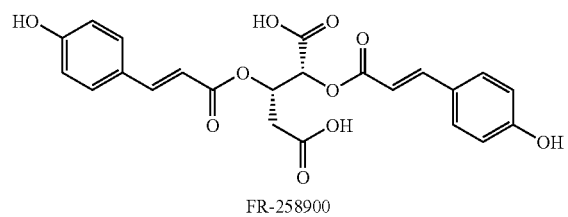
FR-258900
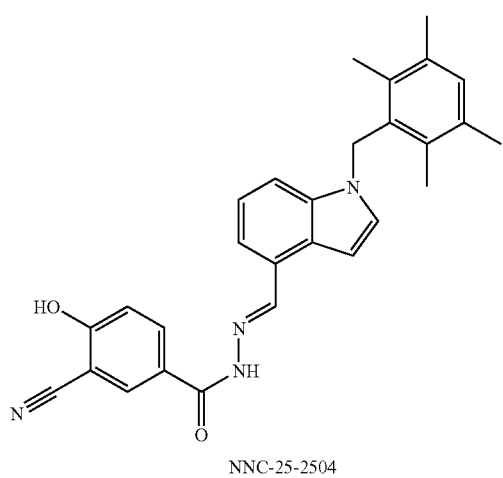
NNC-25-2504
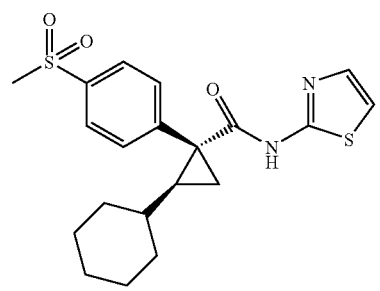
LY-2121260
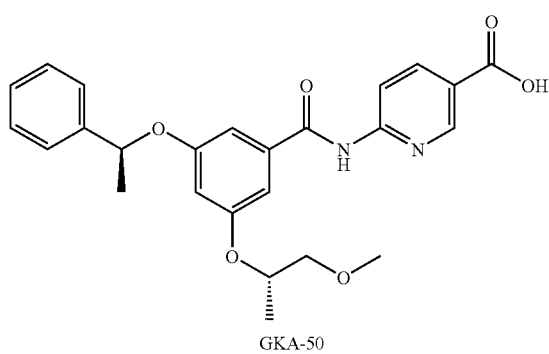
GKA-50
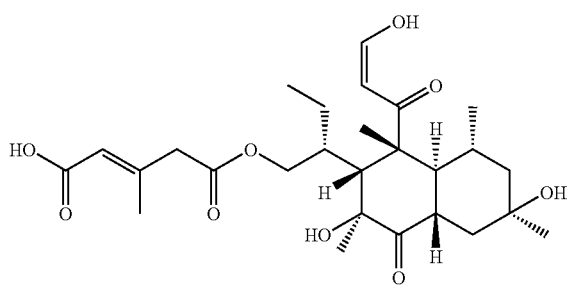
FR-225654

-continued
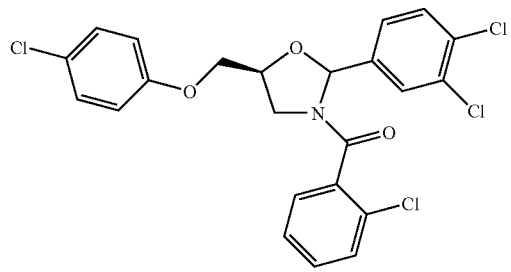
KST-48
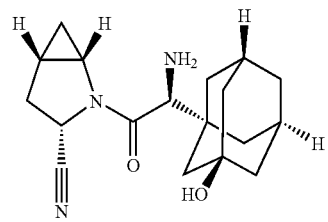
BMS-477118
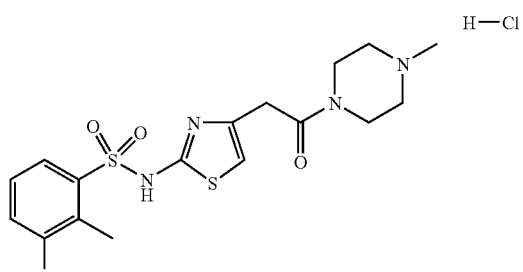
BVT-2733
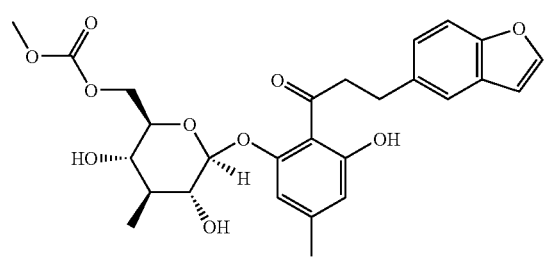
T-1095
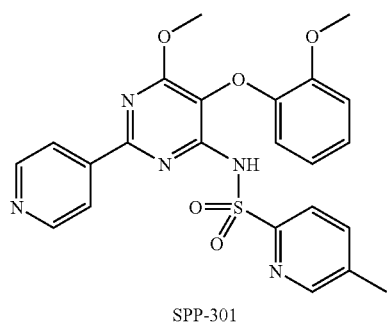
SPP-301
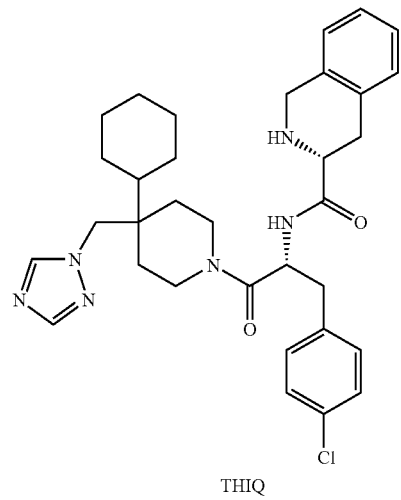
THIQ
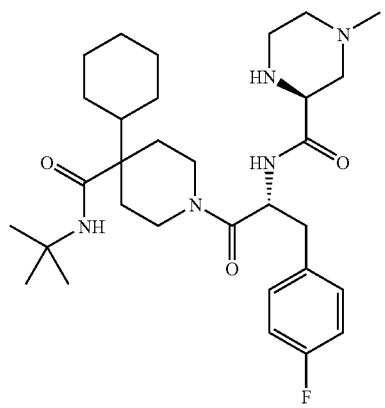
MB243
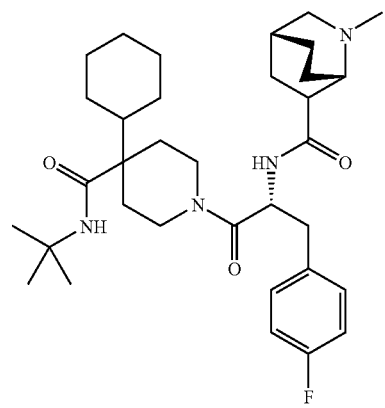
RY764

-continued
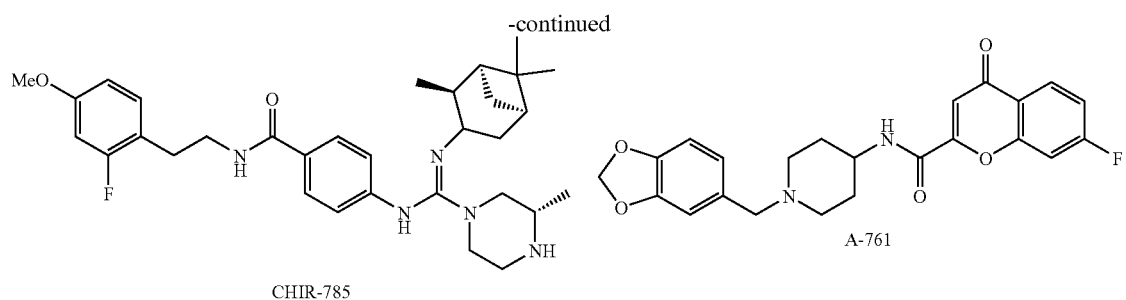
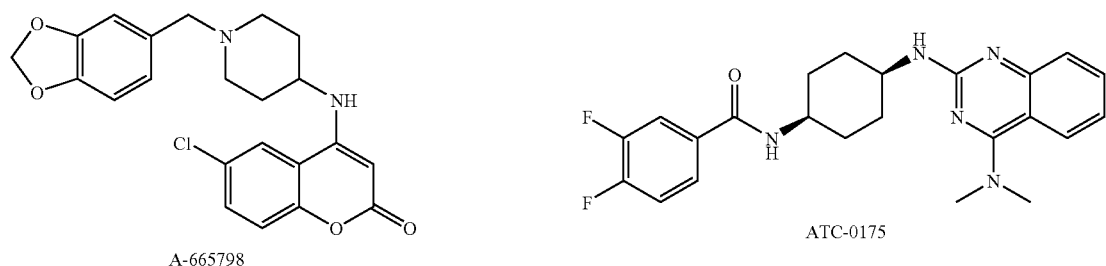
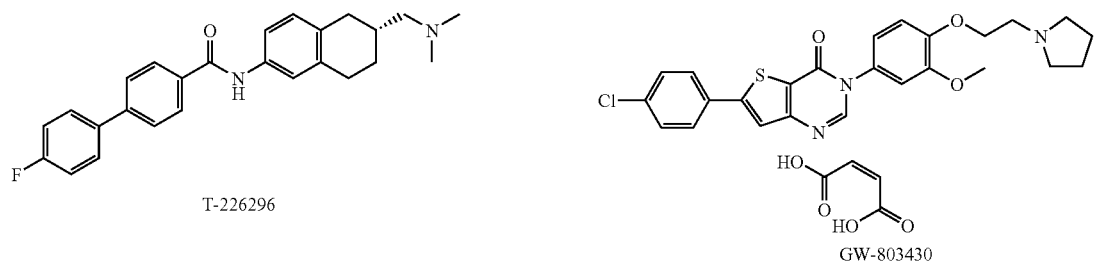
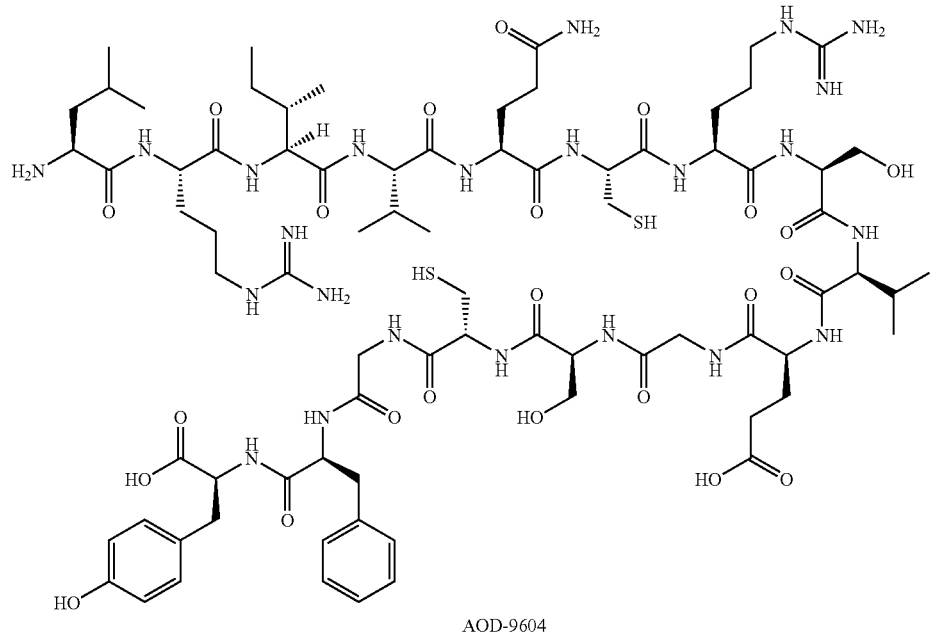

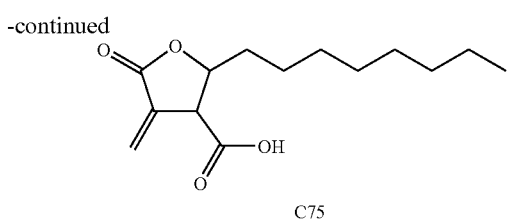

-continued

C75

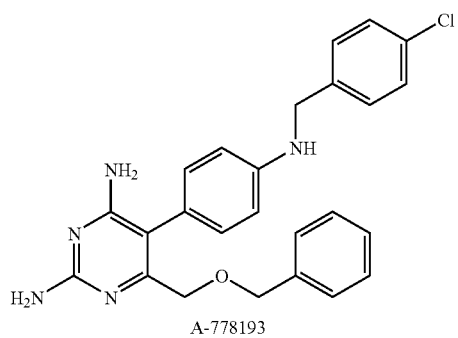

A-778193

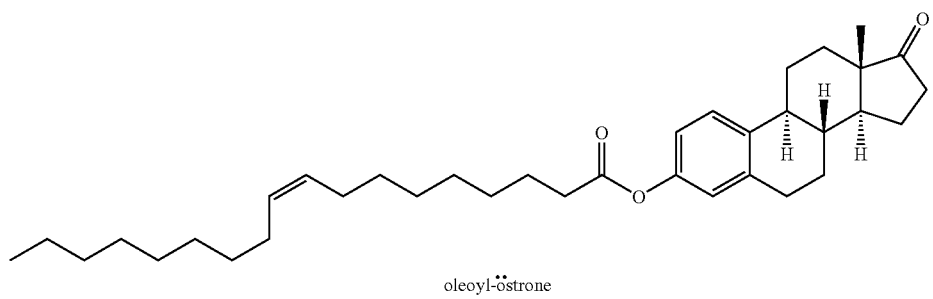

oleoyl-östrone

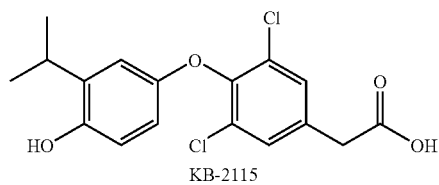

KB-2115

The activity of the compounds was tested through the determination of EC50 values of PPAR agonists in the cellular PPARalpha assay. The potency of substances which bind to human PPARalpha and activate it in an agonistic manner was analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanP-PARalpha-LBD) which mediates expression of the luciferase reporter element depending on a PPARalpha ligand. The stably and constitutively expressed fusion protein GR-GAL4-humanPPARalpha-LBD binds in the cell nucleus of the PPA-Ralpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

I. Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession # AF264724) were cloned in 5'-upstream of a 68 bp-long minimal MMTV promoter (Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Accession # M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARalpha receptor (amino acids S167-Y468; Accession # S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

II. Assay Procedure

The activity of PPARalpha agonists was determined in a 3-day assay, which is described below:

Day 1

The PPARalpha reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10136-027, Invitrogen), 1% penicillin-streptomycin solution (#15140-122, Invitrogen) and 2 mM L-glutamine (#25030-024, Invitrogen). The cultivation takes place in standard cell culture bottles (# 353612, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

III. Data Evaluation

The raw data from the luminometer are transferred into a Microsoft Excel file. Dose-effect plots and EC50 values of PPAR agonists are calculated using the XL.Fit program as specified by the manufacturer (IDBS). The PPARalpha EC50 values for the compounds of Examples 1 to 49 in this assay are in the range from 5 nM to >33 µM. The compounds of the present invention of formula I activate the PPARalpha receptor.

The potency of substances which bind to human PPARdelta and activate it in an agonistic manner was analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanPPARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARdelta receptor (amino acids S139-Y441; Accession # L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

The three (3) day assay to determine the activity of PPARdelta agonists is the same as that described above for the PPARalpha reporter cell line except that the PPARdelta reporter cell line and a specific PPARdelta agonist was used as a standard to control test efficacy. PPARdelta EC50 values in the range from 0.2 nM to >10 μM were measured for the PPAR agonists of Examples 1 to 49 described in this application. Compounds of the invention of formula I activate the PPARdelta receptor.

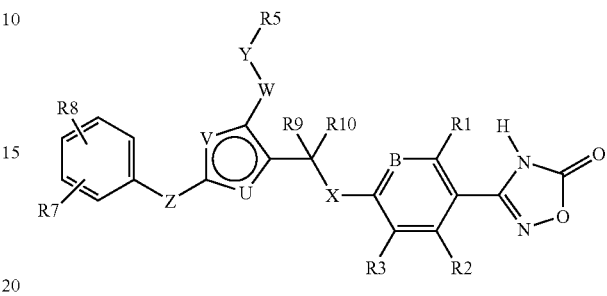

where R8 and R10=H and Z is a bond.

A dotted line means the point of attachment.

TABLE I

| Example | X | W | Y | R5 | R6 | U | V | R1 | R2 | R3 | R7 | B | R9 |
|---|---|---|---|---|---|---|---|---|---|---|---|---|---|
| 1 | O | —CH2— | bond | H | — | S | N | Cl | H | H | p-CF3 | CH | —CH3 |
| 2 | O | —CH2— | bond | H | — | S | N | Cl | H | H | p-CF3 | CH | —CH(CH3)2 |
| 3 | O | —CH2— | bond | H | — | S | N | Cl | H | H | p-CF3 | CH | —CH2CH(CH3)2 |
| 4 | O | —CH2— | bond | H | — | S | N | Cl | H | H | p-CF3 | CH | —CH2CH3 |
| 5 | O | —CH2— | bond | H | — | S | N | Cl | H | H | p-CF3 | CH | —CH2-Ph |
| 6 | O | —CH2— | bond | H | — | S | N | Cl | H | H | p-CF3 | CH | -Ph |
| 7 | O | —CH2— | bond | H | — | S | N | Cl | H | H | p-CF3 | CH | —(CH2)2Ph |
| 8 | O | —CH2— | bond | H | — | O | N | Cl | H | H | p-CF3 | CH | —(CH2)2Ph |
| 9 | O | —CH2— | bond | H | — | S | N | Cl | H | H | p-CF3 | CH | CH2-C6H4-F |
| 10 | O | —CH2— | bond | H | — | S | N | Cl | H | H | p-CF3 | CH | CH2-pyridyl |
| 11 | O | —CH2— | bond | H | — | S | N | Br | H | H | p-CF3 | CH | —CH2CH3 |
| 12 | O | —CH2— | bond | H | — | S | N | —CH2OCH2CF3 | H | H | p-CF3 | CH | —CH2CH3 |
| 13 | O | —CH2— | bond | H | — | S | N | —CH2OCH3 | H | H | p-CF3 | CH | —CH2CH3 |
| 14 | O | —CH2— | bond | H | — | S | N | —CH2OCH2CH3 | H | H | p-CF3 | CH | —CH2CH3 |
| 15 | O | —CH2— | bond | H | — | S | N | —CH2CH3 | H | H | p-CF3 | CH | —CH2CH3 |
| 16 | O | —CH2— | bond | H | — | S | N | cyclopropyl | H | H | p-CF3 | CH | —CH2CH3 |
| 17 | O | —CH2— | bond | H | — | S | N | H | phenyl | | p-CF3 | CH | —CH2CH3 |
| 18 | O | —CH2— | bond | H | — | S | N | —CF3 | H | H | p-CF3 | CH | —CH2CH3 |
| 19 | O | —CH2— | bond | H | — | S | N | C6H4-F | H | H | p-CF3 | CH | —CH2CH3 |
| 20 | O | —CH2— | bond | H | — | S | N | Cl | H | H | p-CF3 | CH | —CF3 |
| 21 | O | —CH2— | bond | H | — | S | N | Cl | H | H | p-CF3 | CH | —CH2CH3 |
| 22 | —OCH2— | —CH2— | bond | H | — | S | N | F | H | H | p-CF3 | CH | —CF3 |
| 23 | —OCH2— | —CH2— | bond | H | — | S | N | Cl | H | H | p-CF3 | CH | —CF3 |

TABLE I-continued

| Example | X | W | Y | R5 | R6 | U | V | R1 | R2 | R3 | R7 | B | R9 |
|---|---|---|---|---|---|---|---|---|---|---|---|---|---|
| 24 | —OCH2— | —CH2— | bond | H | — | S | N |  | H | H | p-CF3 | CH | —CF3 |
| 25 | —OCH2— | —CH2— | bond | H | — | S | N | H | 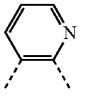 | | p-CF3 | CH | —CF3 |
| 26 | —OCH2— | —CH2— | bond | H | — | S | N | H | 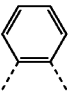 | | p-CF3 | CH | —CF3 |
| 27 | —OCH2— | —CH2— | bond | H | — | S | N | Cl | H | H | p-CF3 | N | —CF3 |
| 28 | —OCH2— | —CH2— | bond | H | — | S | N | F | H | H | p-CF3 | CH | —CH2CH3 |
| 29 | —OCH2— | —CH2— | bond | H | — | S | N | H | 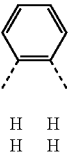 | | p-CF3 | CH | —CH2CH3 |
| 30 | —OCH2— | —CH2— | bond | H | — | S | N | H | H | H | p-CF3 | CH | —CH2CH3 |
| 31 | —OCH2— | —CH2— | bond | H | — | S | N | H | H | H | p-CF3 | CH | —CF2CH2CH3 |
| 32 | —OCH2— | —CH2— | bond | H | — | S | N | H | H | H | p-CF3 | CH | 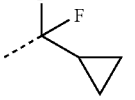 |
| 33 | —OCH2— | —CH2— | bond | H | — | S | N | H | H | H | p-CF3 | CH | 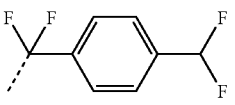 |
| 34 | —CH2— | —CH2— | bond | H | — | S | N | F | H | H | p-CF3 | CH | —(CH2)3CH3 |
| 35 | O | —CH2— | bond | H | — | S | N | F | H | H | p-CF3 | CH | —CH2CH3 |
| 36 | O | —CH2— | 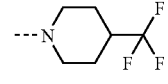 | | | S | N | F | H | H | p-CF3 | CH | —CH2CH3 |
| 37 | O | —CH2— | bond | H | — | S | N | —OCHF2 | H | H | p-CF3 | CH | —CH2CH3 |
| 38 | O | —CH2— | bond | H | — | S | N | —OCH3 | H | H | p-CF3 | CH | —CH2CH3 |
| 39 | O | —CH2— | bond | H | — | S | N | —OH | H | H | p-CF3 | CH | —CH2CH3 |
| 40 | O | —CH2— | bond | H | — | S | N | —OCH3 | H | F | p-CF3 | CH | —CH2CH3 |
| 41 | O | —CH2— | bond | H | — | S | N | —OCHF2 | H | F | p-CF3 | CH | —CH2CH3 |
| 42 | O | —CH2— | 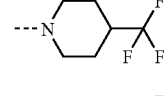 | | | S | N | —OCH3 | H | H | p-CF3 | CH | —CH2CH3 |
| 43 | O | —CH2— | 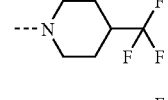 | | | S | N | —OCH3 | H | F | p-CF3 | CH | —CH2CH3 |
| 44 | O | —CH2— | 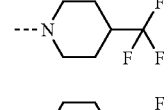 | | | S | N | —OCH2CF3 | H | H | p-CF3 | CH | —CH2CH3 |
| 45 | O | —CH2— | 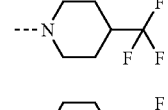 | | | S | N | —OCHF2 | H | H | p-CF3 | CH | —CH2CH3 |
| 46 | O | —CH2— | 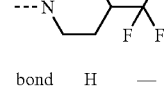 | | | S | N | —OCHF2 | H | F | p-CF3 | CH | —CH2CH3 |
| 47 | O | —CH2— | bond | H | — | S | N | —OCH2CF3 | H | F | p-CF3 | CH | —CH2CH3 |
| 48 | O | —CH2— | bond | H | — | S | N | —OCH2CF3 | H | H | p-CF3 | CH | —CH2CH3 |

TABLE I-continued

| Example | X | W | Y | R5 | R6 | U | V | R1 | R2 | R3 | R7 | B | R9 |
|---|---|---|---|---|---|---|---|---|---|---|---|---|---|
| 49 | O | —CH2— | ![piperidine-CF3] | | | S | N | —OCH2CF3 | H | F | p-CF3 | CH | —CH2CH3 |

The potency of some of the described examples in the GAL4 assays are indicated in the following table:

| Example | PPARdelta EC50 (µM) | PPARalpha EC50 (µM) |
|---|---|---|
| 4 | 0.0002 | 0.012 |
| 10 | 0.006 | 4.38 |
| 16 | 0.001 | 0.117 |
| 20 | 0.001 | 0.307 |
| 22 | 0.017 | 2.64 |
| 25 | 0.003 | 0.544 |
| 27 | 0.017 | 1.21 |
| 32 | 0.127 | >33 |
| 34 | 0.001 | 1.07 |
| 35 | 0.004 | 0.269 |

-continued

| Example | PPARdelta EC50 (µM) | PPARalpha EC50 (µM) |
|---|---|---|
| 37 | 0.0005 | 0.223 |
| (+)-40 | 0.001 | 0.677 |
| 42 | 0.008 | >33 |
| (+)-45 | 0.0003 | 1.23 |
| 48 | 0.001 | 0.087 |

Processes

The compounds of the general formula I according to the invention can be obtained as outlined to the reaction schemes below:

Process A

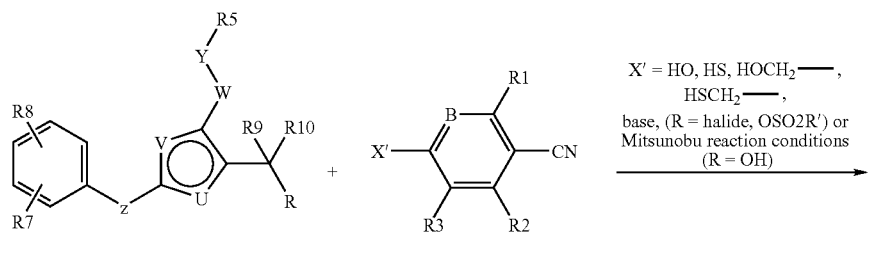

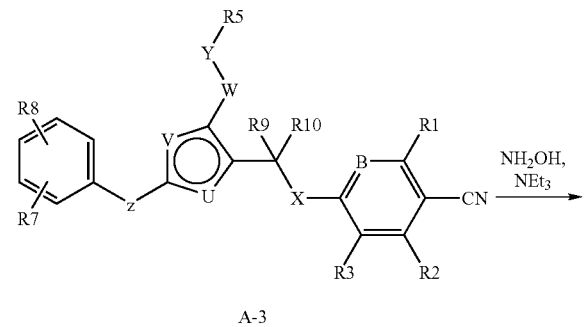

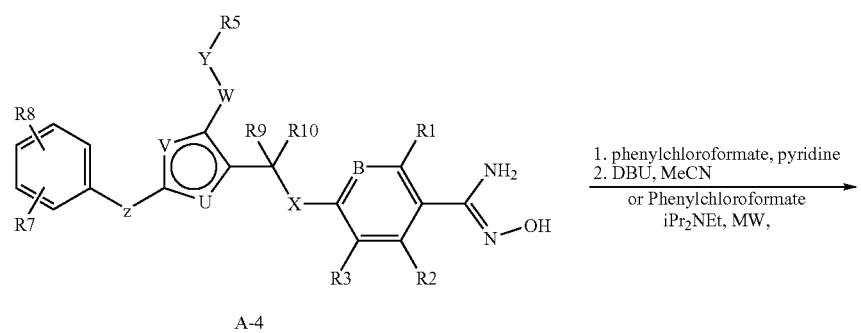

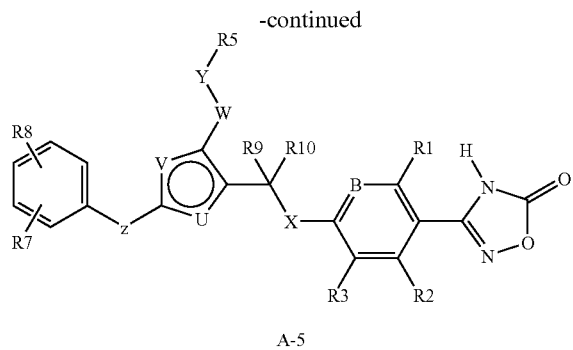

A-5

A compound of general formula A-2 where X' is —OH, —SH, —CH2OH or —CH2SH and R1, R2, R3 and B are as defined above is either reacted with a compound of general formula A-1 where R is halide (I, Br, Cl) or a sulfonate (OSO$_2$CH$_3$, OSO$_2$C$_6$H$_4$—CH$_3$) and R5, R7, R8, R9, R10, U, V, W, Y and Z are as defined above in the presence of a base as cesium carbonate or sodium hydride in a solvent as dimethylformamide or with an alcohol of general formula A-1 where R=OH and R5, R7, R8, R9, R10, U, V, W, Y and Z are as defined above under Mitsunobu reaction conditions (triphenylphosphine, diethylazodicarboxylate for instance) in an apolar solvent as dichloromethane to give a compound of general formula A-3 where X=O, S, —OCH$_2$— or —SCH$_2$—. The compound of general formula A-3 is reacted with hydroxylamine hydrochloride in the presence of a base as triethylamine in a solvent as tetrahydrofuran and methanol to obtain a compound of general formula A-4. This reaction can be facilitated by heating the reaction mixture under microwave irradiation. This compound of general formula A-4 is converted to the product of general formula A-5 by reaction with phenylchloroformate in the presence of a base as pyridine or diisopropylethylamine followed by heating the reaction mixture with microwave irradiation to allow cyclization or alternatively isolating the resulting intermediate and treating it with a base as 1,8-diazabicyclo[5.4.0]undec-7-ene in a solvent as acetonitrile.

Examples 1-10 and 35-36 were obtained according to process A.

Other compounds can also be obtained by process A accordingly or by processes known to those skilled in the art.

Process B

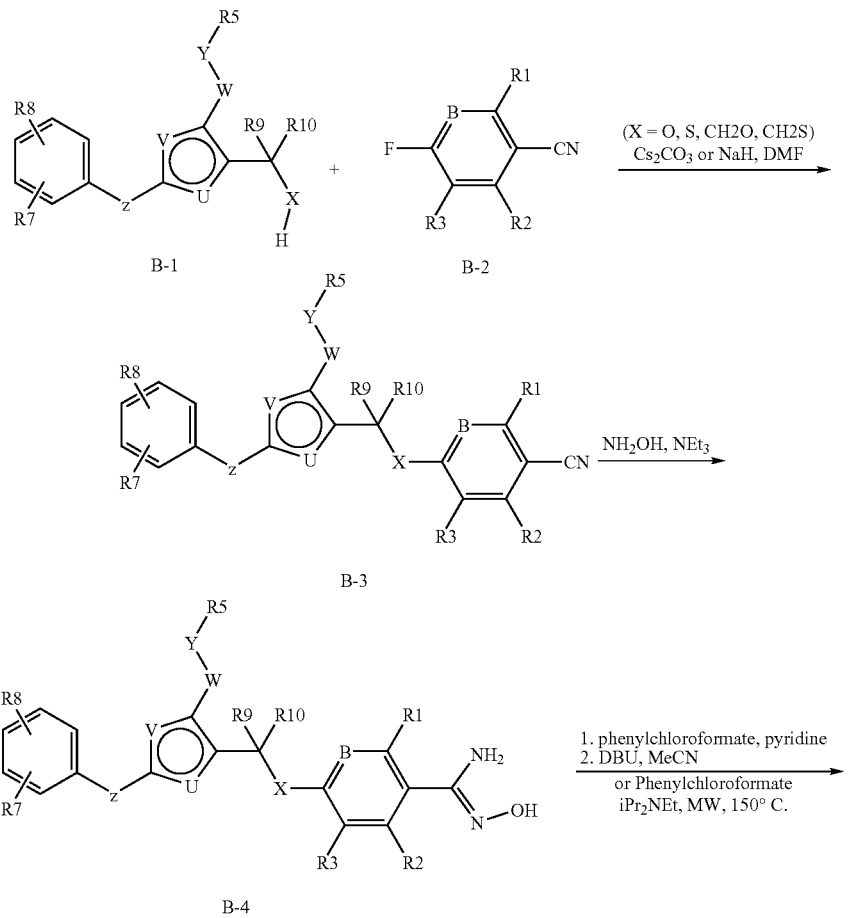

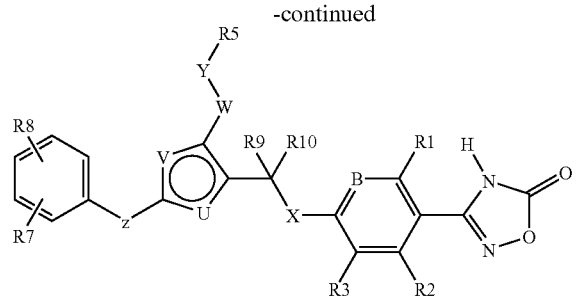

B-5

A compound of general formula B-1 where X is O, S, CH$_2$O or CH$_2$S and R5, R7, R8, R9, R10, U, V, W, Y and Z are as defined above is reacted with a fluoro-nitrile of general formula B-2 where R1, R2, R3 and B are as defined above in the presence of a base such as cesium carbonate or sodium hydride in a solvent such as dimethylformamide to give a compound of general formula B-3. As described in process A, compound B-3 is treated with hydroxylamine hydrochloride in the presence of a base such as triethylamine in a solvent as tetrahydrofuran and methanol to obtain a compound of general formula B-4. This reaction can be facilitated by heating the reaction mixture under microwave irradiation. Compound B-4 is converted to the product of general formula B-5 by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Examples 11-21 and 37-46 were obtained according to process B.

Other compounds can be obtained accordingly or by known processes.

Process C

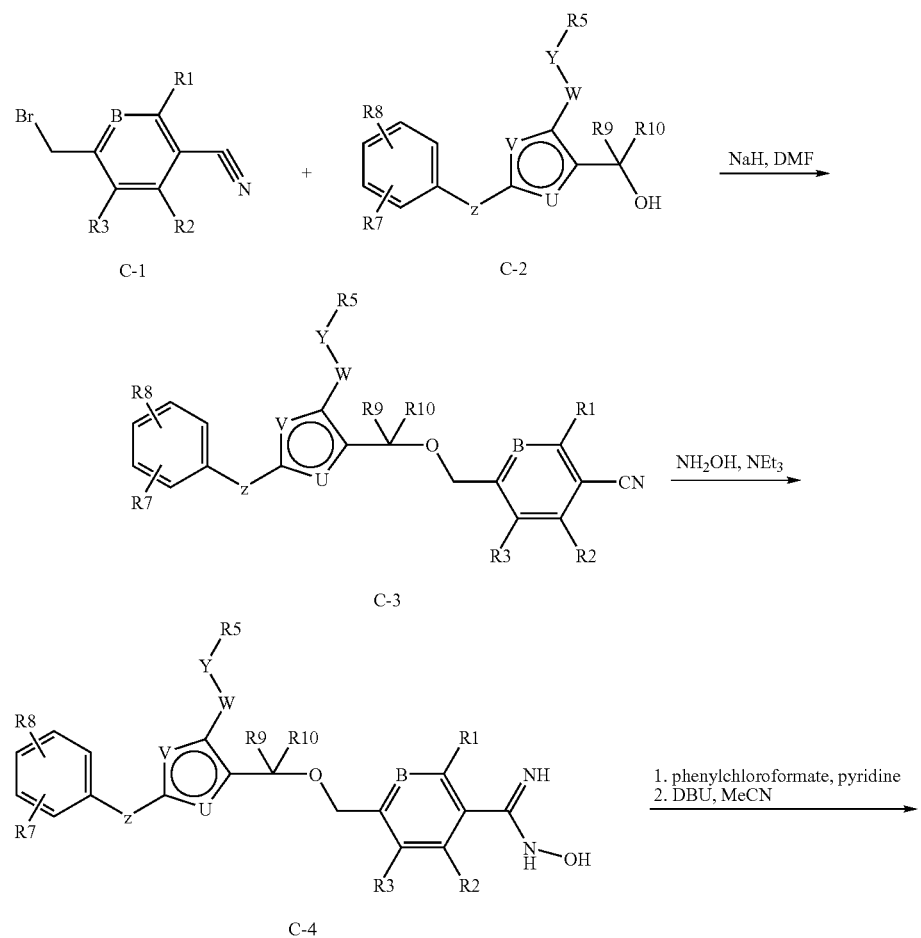

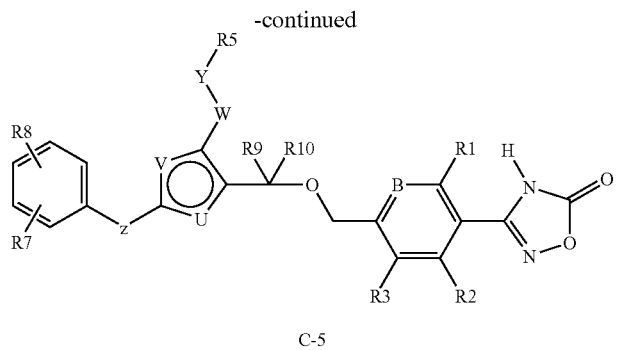

C-5

A compound of general formula C-2 where R5, R7, R8, R9, R10, U, V, W, Y and Z are as defined above is reacted with a benzylic bromide of general formula C-1 where B, R1, R2, R3 and R4 are as defined above in the presence of a base such as sodium hydride in a solvent such as dimethylformamide to give a compound of general formula C-3. As described in process A, compound C-3 is treated with hydroxylamine hydrochloride in the presence of a base such as triethylamine in a solvent as tetrahydrofuran and methanol to obtain a compound of general formula C-4. This reaction can be facilitated by heating the reaction mixture under microwave irradiation. Compound C-4 is converted to the product of general formula C-5 by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Examples 21-33 were obtained according to process C.

Process D:

This process is used for synthesizing the building blocks D-8, which correspond to general formula A-1 of process A, general formula B-1 of process B and general formula C-2 of process C, where R=OH, R10=H, V is N and U, W, Y, Z, R5, R7, R8 and R9 are as defined above.

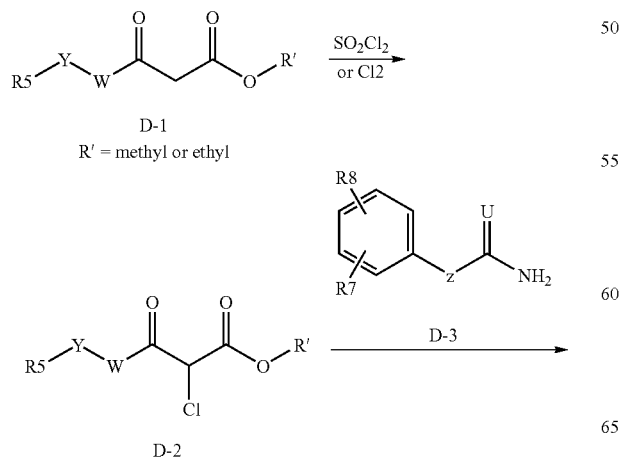

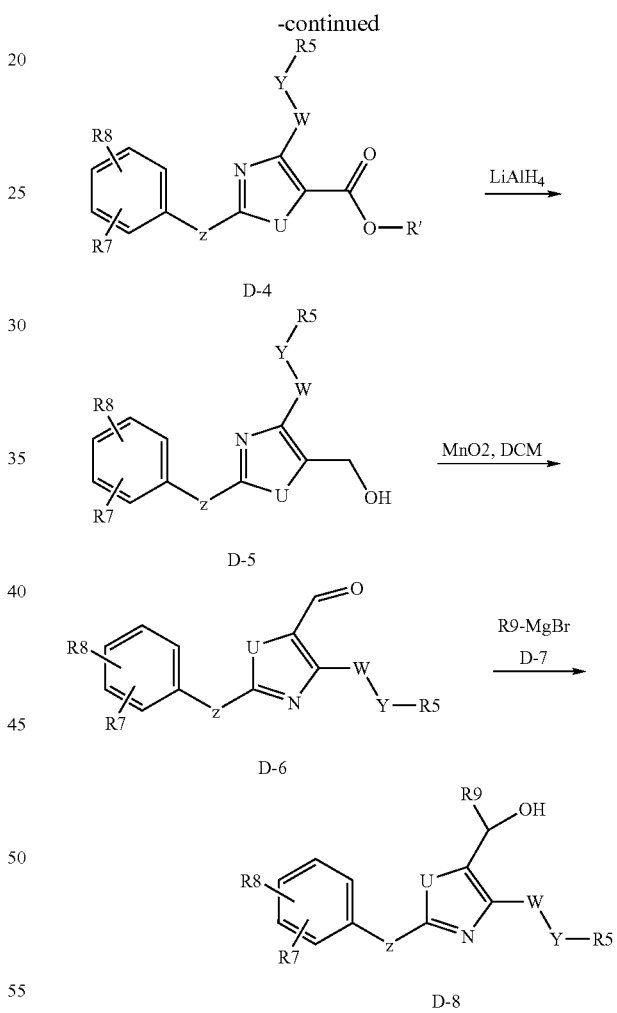

A 3-oxo-carboxylic acid methyl- or ethyl ester of general formula D-1 where R5, Y and W are as defined above is reacted with sulfuryl chloride or chlorine to yield the corresponding chloride of general formula D-2. This compound of general formula D-2 is reacted with a benzamide or thiobenzamide of general formula D-3, where U is S or O and R7, R8 and Z are as defined above to obtain a thiazole or oxazole ester of general formula D-4. The ester of general formula D-4 is reduced with a reducing agent, for example lithium aluminum hydride, to the alcohol of general formula D-5, where R5, R7, R8, U, W, Y and Z are as defined above.

A compound of general formula D-5 is treated with an oxidizing agent as manganese dioxide in an apolar solvent as dichloromethane to obtain an aldehyde of general formula D-6 where W, Y, U, Z, A, R5, R7 and R8 are as defined above. The aldehyde of general formula D-6 is reacted with a Grignard reagent of general formula D-7, where R9 is as defined above to obtain an secondary alcohol of general formula D-8.

Other compounds can be obtained accordingly or by known processes.

Process E:

This process is used for synthesizing the building blocks E-3, which correspond to general formula A-1 of process A, general formula B-1 of process B and general formula C-2 of process C, where R=OH, R9 is —CF2R", R10=H, V is N and U, W, Y, Z, R5, R7 and R8 are as defined above.

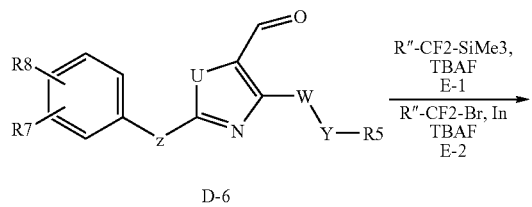

D-6

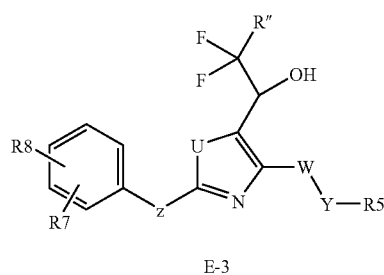

E-3

A compound of general formula D-6 (derived from process D) is treated with a difluorotrimethylsilyl reagent of general formula E-1 where R" is (C1-C5)alkyl, (C2-C5)alkenyl, (C0-C5) alkylene-(C6-C14) aryl, (C0-C5) alkylene-(C5-C15) heteroaryl, (C0-C5) alkylene-(C3-C8) cycloalkyl, (C0-C5) alkylene-(C3-C8) cycloalkenyl, wherein alkyl and alkylene are unsubstituted or mono-, di- or tri-substituted by F and aryl, heteroaryl, cycloalkyl and heterocycloalkyl are unsubstituted or mono-, di- or tri-substituted by halogen, (C1-C4) alkyl, —CF3, —CHF2, or O—(C1-C4)alkyl; in a polar solvent as tetrahydrofuran with catalytic amounts of a fluoride ion source such as KF or tetrabutyl ammonium fluoride or alternatively with a bromodifluoromethyl reagent of general formula E-2 in the presence of indium in a polar solvent as tetrahydrofuran in an ultrasonic bath to obtain a secondary alcohol of general formula E-3.

Other compounds can be obtained accordingly or by known processes.

Process F:

This process is used for synthesizing the building blocks F-3, which corresponds to general formula C-1 of process C.

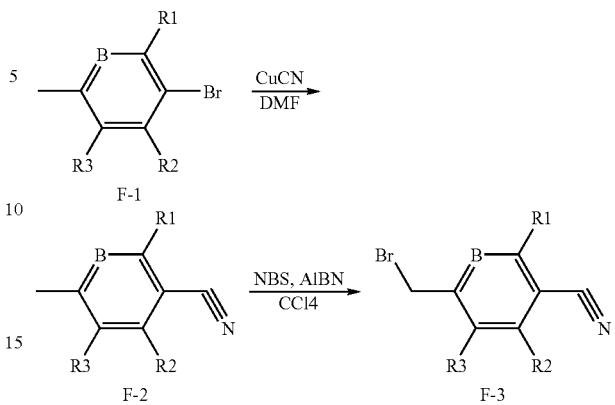

A 1-bromo-4-methyl-benzene of general formula F-1, where B, R1, R2, R3 and R4 are as defined above is reacted with copper cyanide in a polar solvent as dimethylformamide at elevated temperature as for example 150-200° C. to obtain the 4-methyl-benzonitrile of general formula F-2. The 4-methyl-benzonitrile of general formula F-2 is brominated by the treatment with N-bromosuccinimide in refluxing tetrachloromethane in the presence of a radical initiator like AIBN to obtain the 4-Bromomethyl-benzonitrile of general formula F-3.

Process G:

This process is used for synthesizing the building blocks G-3, which corresponds to general formula B-2 of process B, where B=C(R4), R1=—CH2-Nuc and R2, R3 and R4 are as defined.

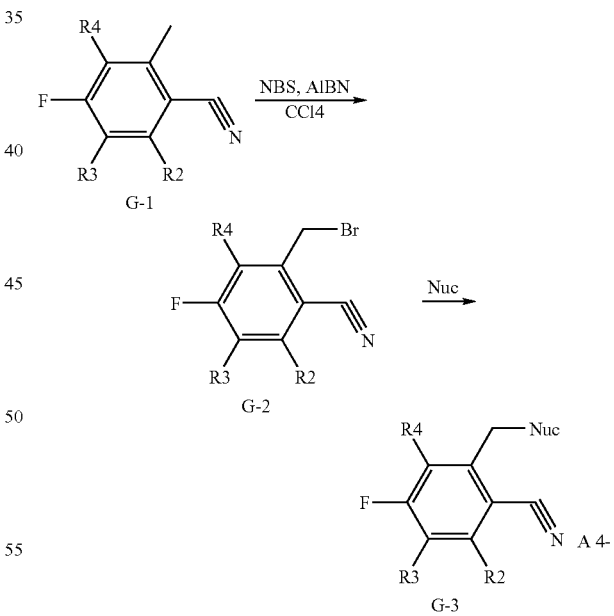

fluoro-2-methylbenzonitrile of general formula G-1 is brominated by the treatment with N-bromosuccinimide in refluxing tetrachloromethane in the presence of a radical initiator like AIBN to obtain the 2-Bromomethyl-benzonitrile of general formula G-2. The compound of general formula G-2 is reacted with a nucleophile, for example a primary or secondary amine or a sodium salt of a thiol or an alcohol, in a polar solvent such a dimethylformamide to obtain the compound of general formula G-3.

Process H:
This process is used for synthesizing the building blocks H-3, which correspond to general formula B-2 of process B, where B=C(R4), R1, R2, R3 and R4 are as defined.

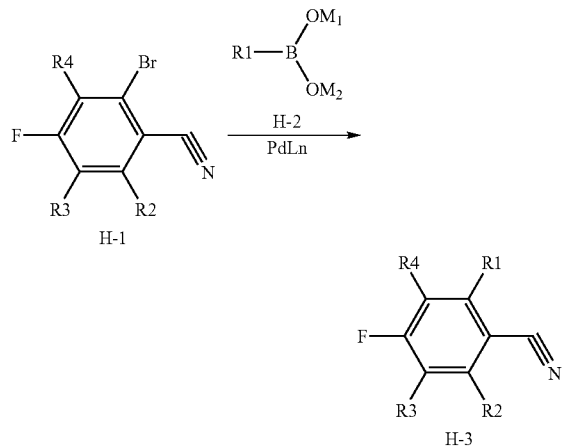

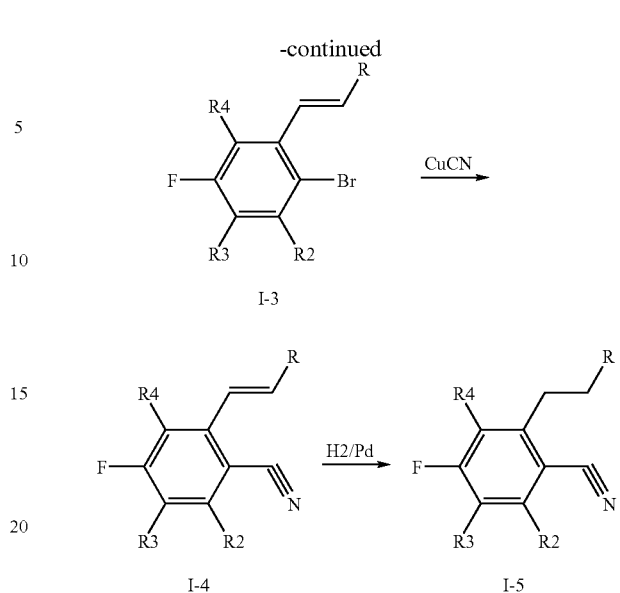

A 4-fluoro-2-bromobenzonitrile of general formula H-1 is converted to a compound of the general formula H-3 by reacting with a boronic acid or a boronic ester of general formula H-2, where M1 & M2 can be independently hydrogen or (C1-C8) alkyl. In the case of alkyl, M1/M2 can form a ring system and R1 is as defined above, using a catalytic amount of a transition metal as for example Palladium and a ligand as for example triphenylphosphin in the presence of a base as for example $Cs_2CO_3$ in a solvent as for example DMF/water.

Process I:
This process is used for synthesizing the building blocks I-5, which correspond to general formula B-2 of process B, where B=C(R4), R1 is —CH2CH2R and R2, R3 and R4 are as defined.

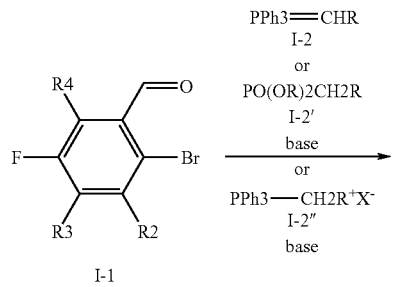

A 2-bromo-5-fluorobenzaldehyde of general formula I-1 where R2, R3 and R4 are as defined above is reacted under Wittig type reaction conditions either with a triphenylphosphoranylidene of general formula I-2 where R is (C1-C7) alkyl, wherein alkyl is 1- to 5-fold substituted by F;

or with a phosphonat of general formula I-2' where R is (C1-C7) alkyl, wherein alkyl is 1- to 5-fold substituted by F in the presence of a base like sodium hydride or with a phosphonium salt of general formula I-2" where R is (C1-C7) alkyl, wherein alkyl is 1- to 5-fold substituted by F in the presence of a base as n-butyl lithium in a polar solvent as tetrahydrofuran to obtain a compound of general formula I-3 where R2, R3, R4 and R are as defined above. The bromide of general formula I-3 where R2, R3, R4 and R are as defined above is reacted with copper cyanide in a polar solvent as dimethylformamide at elevated temperature as for example 150-200° C. to obtain the 4-fluoro-benzonitrile of general formula I-4 where R2, R3, R4 and R are as defined above. The double bond of the compound of general formula I-4 may be hydrogenated with hydrogen and a palladium catalyst in a polar solvent as methanol to obtain the compound of general formula I-5 where R2, R3, R4 and R are as defined above.

Process J

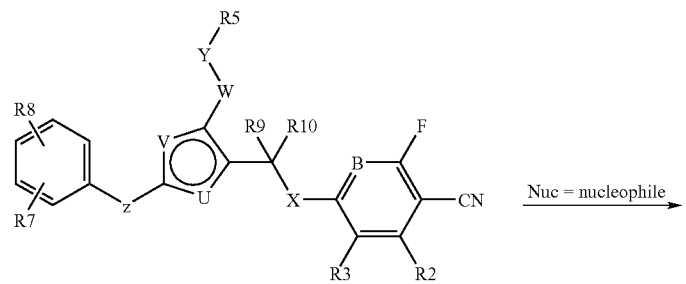

-continued

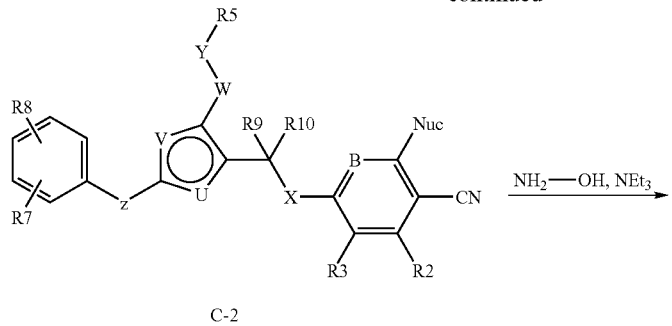

C-2

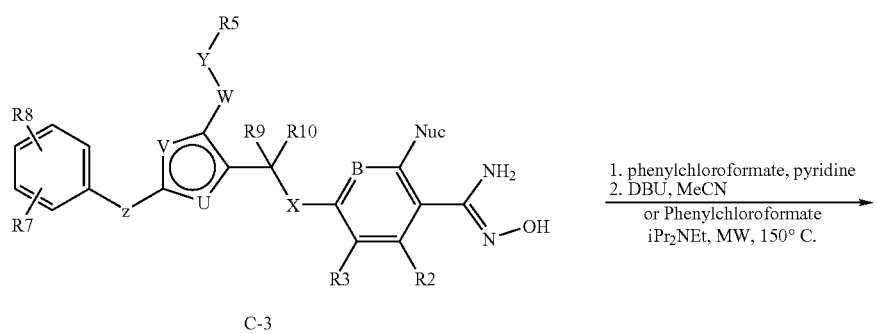

C-3

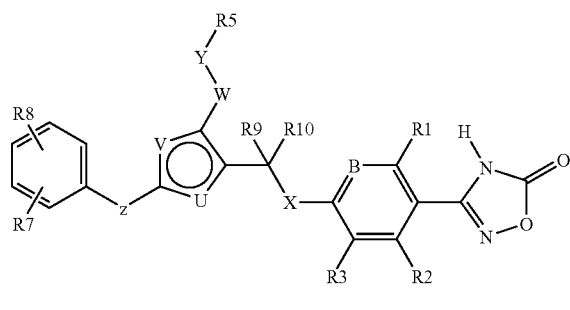

C-4

A compound of general formula C-1 where R1=F and B. R2, R3, R5, R7, R8, R9, R10, U, V, W, Y and Z are as defined above is reacted with a nucleophile, e.g. sodium methylate, to obtain a compound of general formula C-2. A compound of general formula C-2 is reacted with hydroxylamine hydrochloride in the presence of a base as triethylamine in a solvent as tetrahydrofuran and methanol to obtain a compound of general formula C-3. This reaction can be facilitated by heating the reaction mixture under microwave irradiation. A compound of general formula C-3 is converted to the product of general formula C-4 by reaction with phenylchloroformate in the presence of a base as pyridine or diisopropylethylamine followed by heating the reaction mixture with microwave irradiation to allow cyclization or alternatively isolating the resulting intermediate and treating it with a base as 1,8-diazabicyclo[5.4.0]undec-7-ene in a solvent as acetonitrile.

Examples 47-49 were obtained according to process J.

Process J

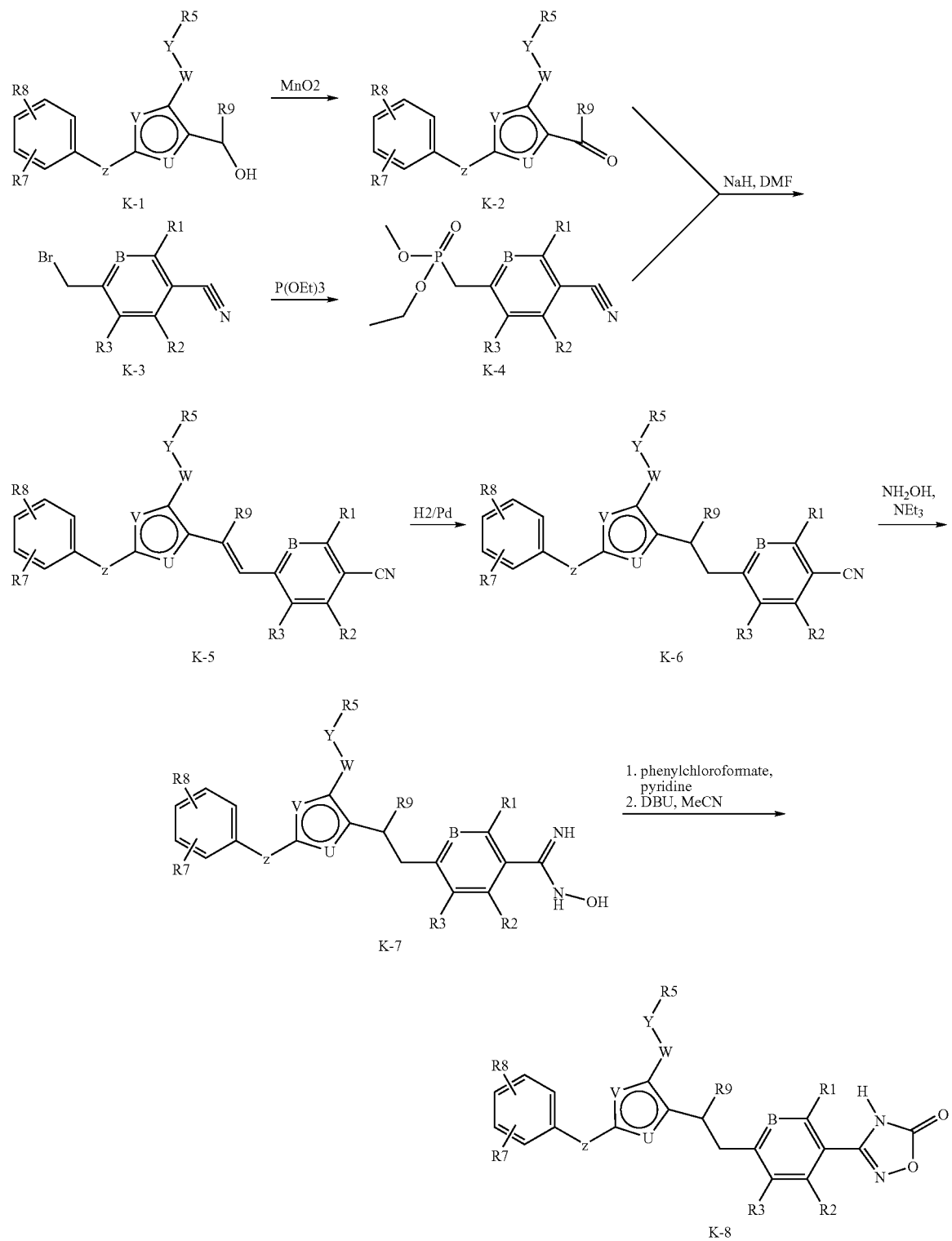

A compound of general formula K-1 where R5, R7, R8, R9, U, V, W, Y and Z are as defined above is treated with an oxidizing agent as manganese dioxide in an apolar solvent as dichloromethane to obtain a ketone of general formula K-2 where R5, R7, R8, R9, U, V, W, Y and Z are as defined above. A 4-bromomethyl-benzonitrile of general formula K-3, where R1, R2, R3, R4 and B are as defined above is reacted with a phosphite such as triethylphosphite under elevated temperature as for example 120-180° C. to obtain a phosphonate of general formula K-4 where R1, R2, R3, R4 and B are as defined above. The phosphonate of general formula K-4 where R1, R2, R3, R4 and B are as defined above and the ketone of general formula K-2 where R5, R7, R8, R9, U, V, W, Y and Z are as defined above are reacted under Wittig type conditions in the presence of a base as sodium hydride in a polar solvent as tetrahydrofuran to obtain the compound of general formula K-5 where R1, R2, R3, R4, R5, R7, R8, R9, B, U, V, W, Y and Z are as defined above. The double bond of the compound of general formula K-5 is hydrogenated with hydrogen and a palladium catalyst in a polar solvent as methanol to obtain the compound of general formula K-6 where R1, R2, R3, R4, R5, R7, R8, R9, B, U, V, W, Y and Z are as defined above. As described in process A, compound K-6 where R1, R2, R3, R4, R5, R7, R8, R9, B, U, V, W, Y and Z are as defined above is treated with hydroxylamine hydrochloride in the presence of a base such as triethylamine in a solvent as tetrahydrofuran and methanol to obtain a compound of general formula K-7 where R1, R2, R3, R4, R5, R7, R8, R9, B, U, V, W, Y and Z are as defined above. This reaction can be facilitated by heating the reaction mixture under microwave irradiation. Compound K-7 is converted to the product of general formula K-8 where R1, R2, R3, R4, R5, R7, R8, R9, B, U, V, W, Y and Z are as defined above by reaction with phenylchloroformate in the presence of a base as pyridine or diisopropylethylamine followed by heating the reaction mixture under microwave irradiation to allow cyclization or alternatively isolating the resulting intermediate and treating it with a base as 1,8-diazabicyclo[5.4.0]undec-7-ene in a solvent as acetonitrile.

Example 34 was obtained according to process K.

Process L:

This process is used for synthesizing the building blocks L-3, which corresponds to general formula B-2 of process B, where B=C(R4), R1=OR, R is (C1-C4)alkyl or (C0-C2)alkylene-(C3-C6)cycloalkyl wherein alkyl and alkylene are unsubstituted or mono, di- or trisubstituted by F, and where R2, R3 and R4 are as defined above.

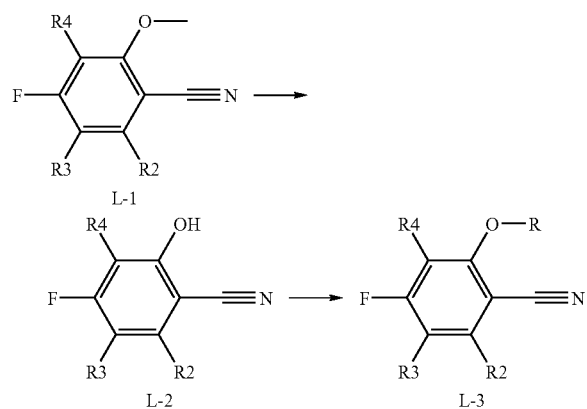

The aryl methyl ether of general formula L-1 where R2, R3 and R4 are as defined above, is demethylated by the treatment with aluminum trichloride in refluxing dichloroethane to give the phenol of general formula L-2. The phenol of general formula L-2 is reacted with an electrophile RX where X is a leaving group such as halide or a sulfonate in a polar solvent like dimethylformamide in the presence of a base like potassium carbonate to obtain a compound of general formula L-3.

When methyl chlorodifluororacetate is used as electrophile and the reaction mixture is heated to 60-120° C. in a solvent such as dimethylformamide or dimethylacetamide, the compound of general formula L-3 where R is CHF2 is obtained.

Other compounds can be obtained accordingly or by known processes.

Process M:

This process is used for synthesizing the building blocks M-2, which corresponds to general formula B-2 of process B, where B=C(R4), R1=OR, R is (C1-C4) alkyl or (C0-C2) alkylene-(C3-C6)cycloalkyl wherein alkyl and alkylene are unsubstituted or mono, di- or trisubstituted by F, and where R2, R3 and R4 are H.

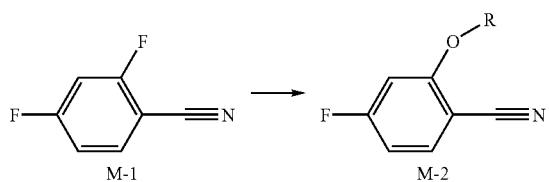

2,4-Difluoro-benzonitrile of formula M-1 is treated with an alcohol ROH in a solvent such as tetrahydrofuran in presence of a base such as potassium tert-butoxide at 0-5° C. to give the ether of general formula M-2 where R is (C1-C4) alkyl or (C0-C2)alkylene-(C3-C6)cycloalkyl wherein alkyl and alkylene are unsubstituted or mono, di- or trisubstituted by F.

Other compounds can be obtained accordingly or by known processes.

Process N:

This process is used for synthesizing the building blocks N-4 and N-7, which corresponds to general formula A-1 of process A where R=OH, general formula B-1 of process B where X is O, and general formula C-2 of process C, where W is CH2, R10 is H, Z is bond, and U, V, Y, R5, R7 and R8 are as defined above, and R9 is H for N-4 or as defined as above for N-7.

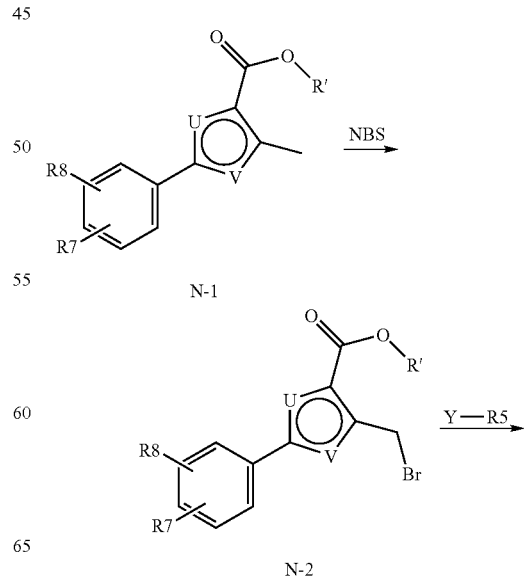

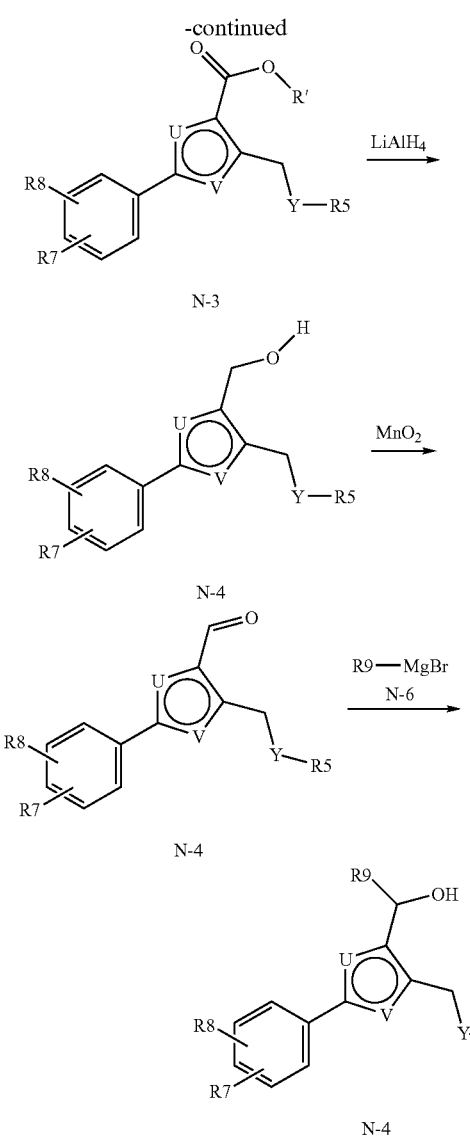

The oxazole or thiazole ester of general formula N-1 where R' is lower alkyl, U, V, R7 and R8 are as defined above, is brominated by the treatment with N-bromosuccinimide in refluxing tetrachloromethane or dichloromethane in the presence of a radical initiator like AIBN or benzoyl peroxide to yield the brominated product of general formula N-2. The alkyl bromide of general formula N-2 is reacted with a nucleophile Y—R5, where Y is OH or Y is NH(R6) and R5, R6 are as defined above, in a polar solvent like acetonitrile in the presence of a base like potassium carbonate to obtain a compound of general formula N-3. The ester of general formula N-3 is reduced with a reducing agent, such as lithium aluminum hydride, to the alcohol of general formula N-4. A compound of general formula N-4 is treated with an oxidizing agent such as manganese dioxide in an apolar solvent as dichloromethane to obtain an aldehyde of general formula N-5 where Y, U, V, R5, R7 and R8 are as defined above. The aldehyde of general formula N-5 is reacted with a Grignard reagent of general formula N-6, where R9 is as defined above to obtain an secondary alcohol of general formula N-7.

Other compounds can be obtained accordingly or by known processes.

List of abbreviation:
Ac acetyl
AIBN 2,2'-azobis(2-methylpropionitrile)
Bn benzyl
iBu isobutyl
tBu tert-Butyl
BuLi n-butyllithium
Bz benzoyl
CI Chemical ionization (MS)
Cy cyclohexyl
DBU 1,8-diazabicyclo[5.4.0]undec-7-ene
DEAD diethylazodicarboxylate
DCI Direct chemical ionization (MS)
DCM dichloromethane
DMAP N,N-dimethylaminopyridine
DMF N,N-dimethylformamide
DMSO dimethylsulfoxide
EE ethyl acetate
eq equivalents
EI Electron impact ionization (MS)
ESI electrospray-Ionization (MS)
FG Functional group
F-TEDA 1-chloromethyl-4-fluoro-1,4-diazoniabicyclo [2.2.2]octane bis(tetrafluoroborate)
Hal halogen
HPLC High performance liquid chromatography
LC-MS liquid chromatography coupled with mass-spectroscopy
LG Leaving Group
Me methyl
MCPBA Meta-chloroperbenzoic acid
MS mass-spectroscopy
MsCl Methanesulfonylchloride
MW microwave
NBS N-bromosuccinimide
NMR Nuclear magnetic resonance
p para
Pd/C palladium on carbon
PG Protecting Group
iPr isopropyl
nPr n-propyl
pTsOH p-toluenesulfonic acid
Rf retention factor (TLC)
SFC Supercritical fluid chromatography
TBAF Tetrabutyl ammonium fluoride
tert Tertiary
TLC Thin layer chromatography
TMS trimethylsilyl Further compounds of formula I can be prepared correspondingly or by known processes.

The experimental procedures for preparing the examples mentioned above are described below:

Building Block Synthesis According to Process D:

1-[4-Methyl-2-(4-trifluoromethyl-phenyl)-thiazol-5-yl]-ethanol

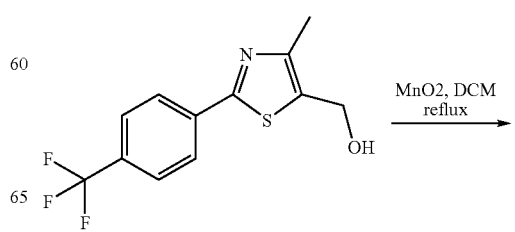

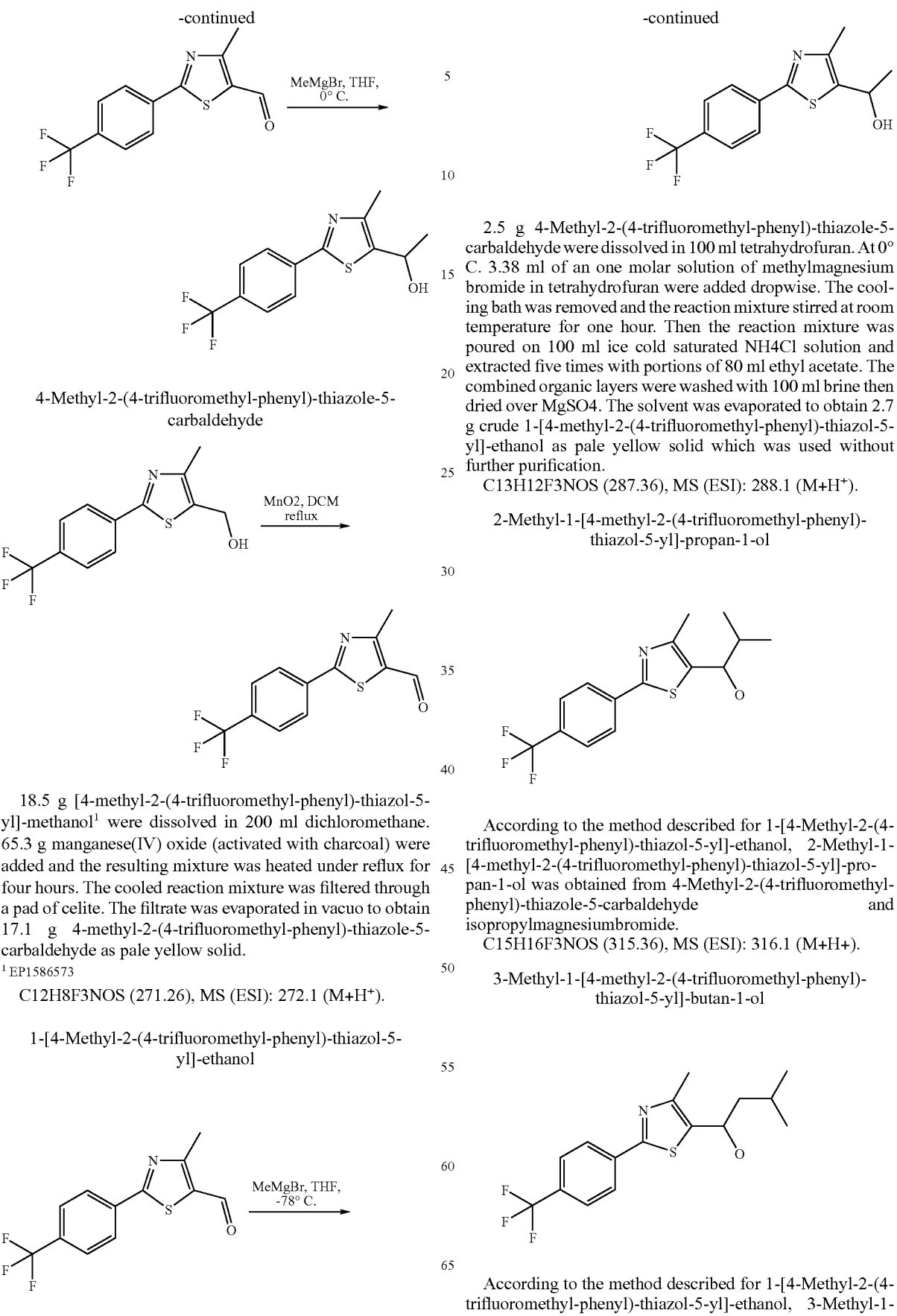

4-Methyl-2-(4-trifluoromethyl-phenyl)-thiazole-5-carbaldehyde 18.5 g [4-methyl-2-(4-trifluoromethyl-phenyl)-thiazol-5-yl]-methanol[1] were dissolved in 200 ml dichloromethane. 65.3 g manganese(IV) oxide (activated with charcoal) were added and the resulting mixture was heated under reflux for four hours. The cooled reaction mixture was filtered through a pad of celite. The filtrate was evaporated in vacuo to obtain 17.1 g 4-methyl-2-(4-trifluoromethyl-phenyl)-thiazole-5-carbaldehyde as pale yellow solid.

[1] EP1586573

C12H8F3NOS (271.26), MS (ESI): 272.1 (M+H$^+$).

1-[4-Methyl-2-(4-trifluoromethyl-phenyl)-thiazol-5-yl]-ethanol 2.5 g 4-Methyl-2-(4-trifluoromethyl-phenyl)-thiazole-5-carbaldehyde were dissolved in 100 ml tetrahydrofuran. At 0° C. 3.38 ml of an one molar solution of methylmagnesium bromide in tetrahydrofuran were added dropwise. The cooling bath was removed and the reaction mixture stirred at room temperature for one hour. Then the reaction mixture was poured on 100 ml ice cold saturated NH4Cl solution and extracted five times with portions of 80 ml ethyl acetate. The combined organic layers were washed with 100 ml brine then dried over MgSO4. The solvent was evaporated to obtain 2.7 g crude 1-[4-methyl-2-(4-trifluoromethyl-phenyl)-thiazol-5-yl]-ethanol as pale yellow solid which was used without further purification.

C13H12F3NOS (287.36), MS (ESI): 288.1 (M+H$^+$).

2-Methyl-1-[4-methyl-2-(4-trifluoromethyl-phenyl)-thiazol-5-yl]-propan-1-ol

According to the method described for 1-[4-Methyl-2-(4-trifluoromethyl-phenyl)-thiazol-5-yl]-ethanol, 2-Methyl-1-[4-methyl-2-(4-trifluoromethyl-phenyl)-thiazol-5-yl]-propan-1-ol was obtained from 4-Methyl-2-(4-trifluoromethyl-phenyl)-thiazole-5-carbaldehyde and isopropylmagnesiumbromide.

C15H16F3NOS (315.36), MS (ESI): 316.1 (M+H+).

3-Methyl-1-[4-methyl-2-(4-trifluoromethyl-phenyl)-thiazol-5-yl]-butan-1-ol

According to the method described for 1-[4-Methyl-2-(4-trifluoromethyl-phenyl)-thiazol-5-yl]-ethanol, 3-Methyl-1-

[4-methyl-2-(4-trifluoromethyl-phenyl)-thiazol-5-yl]-butan-1-ol was obtained from 4-Methyl-2-(4-trifluoromethyl-phenyl)-thiazole-5-carbaldehyde and isobutylmagnesiumbromide.

C16H18F3NOS (329.39), MS (ESI): 330.0 (M+H+).

1-[4-Methyl-2-(4-trifluoromethyl-phenyl)-thiazol-5-yl]-propan-1-ol

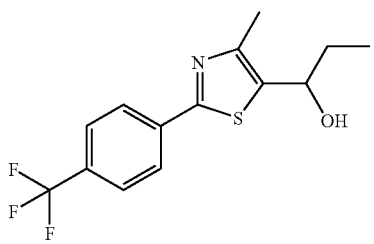

According to the method described for 1-[4-methyl-2-(4-trifluoromethyl-phenyl)-thiazol-5-yl]-ethanol, 1-[4-methyl-2-(4-trifluoromethyl-phenyl)-thiazol-5-yl]-propan-1-ol was obtained from 4-methyl-2-(4-trifluoromethyl-phenyl)-thiazole-5-carbaldehyde and ethylmagnesiumbromide.

C14H14F3NOS (301.33), MS (ESI): 302.0 (M+H+).

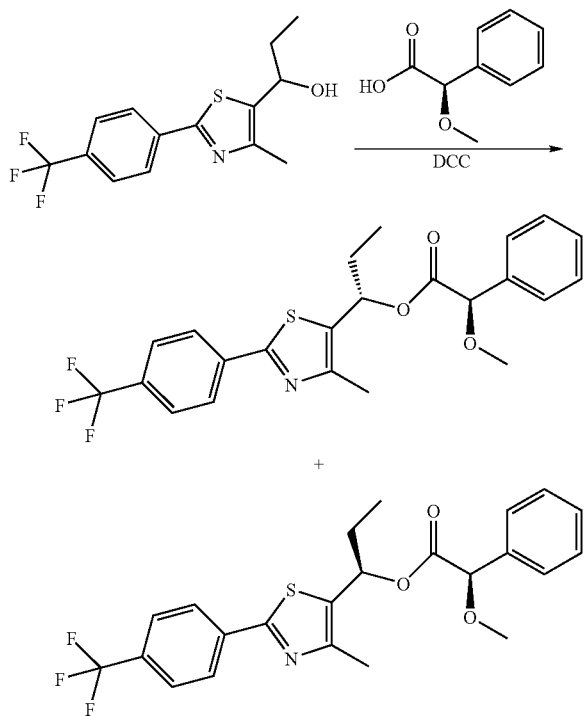

To a solution of 10.48 g of racemic 1-[4-methyl-2-(4-trifluoromethyl-phenyl)-thiazol-5-yl]-propan-1-ol in 210 mL of tetrahydrofuran was added 5.9 g of (R)-(−)-α-methoxyphenyl acetic acid, 40 mL of a molar solution of N,N-dicyclohexylcarbodiimide in dichloromethane and a few mg of N,N-dimethylaminopyridine. The resulting mixture was stirred at room temperature for 1 hour then filtered. The filtrate was concentrated under reduced pressure and the diastereomers were separated by column chromatography on silica gel (gradient from heptane 100 to heptane 90/ethyl acetate 10) to give:

4.09 g of (+)-(R)-methoxy-phenyl-acetic acid (S)-1-[4-methyl-2-(4-trifluoromethyl-phenyl)-thiazol-5-yl]-propyl ester (less polar fraction) according to $^1$H NMR analysis[2] C23H22F3NO3S (449.50), MS (ESI): 450.1 (M+H$^+$), and 5.42 g of (−)-(R)-methoxy-phenyl-acetic acid (R)-1-[4-methyl-2-(4-trifluoromethyl-phenyl)-thiazol-5-yl]-propyl ester (more polar fraction) according to $^1$H NMR analysis[2] C23H22F3NO3S (449.50), MS (ESI): 450.1 (M+H$^+$).

[2] Trost, B. M.; Belletire, J. L.; Godleski, S.; McDougal, P. G.; Balkovec, J. M. J. Org. Chem. 1986, 51, 2370

(+)-(R)-1-[4-Methyl-2-(4-trifluoromethyl-phenyl)-thiazol-5-yl]-propan-1-ol

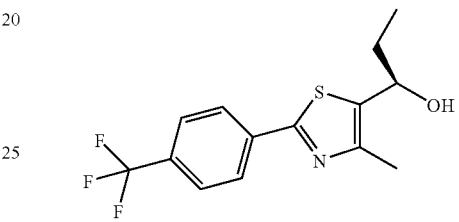

To a solution of 3.74 g of (−)-(R)-methoxy-phenyl-acetic acid (R)-1-[4-methyl-2-(4-trifluoromethyl-phenyl)-thiazol-5-yl]-propyl ester in 19 mL of tetrahydrofuran and 19 mL of ethanol at 0° C. was dropwise added 24.5 mL of a molar solution of sodium hydroxide in 20.4 mL of water. The resulting mixture was stirred at 0° C. for 15 minutes then 24.5 mL of a 5N solution of hydrochloric acid in 20.4 mL of water was added. After removal of the organic solvents under vacuum, the mixture was extracted with ethyl acetate, filtered through a silicone treated paper filter and concentrated under reduced pressure. The residue was purified by column chromatography on silica gel (dichloromethane 90/ethyl acetate 10) to give 2.09 g of (+)-(R)-1-[4-methyl-2-(4-trifluoromethyl-phenyl)-thiazol-5-yl]-propan-1-ol.

C14H14F3NOS (301.33), MS (EI): 301 (M$^+$).

(−)-(S)-1-[4-Methyl-2-(4-trifluoromethyl-phenyl)-thiazol-5-yl]-propan-1-ol

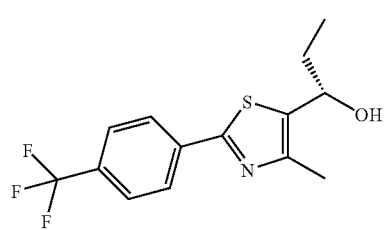

According to the method described for (+)-(R)-1-[4-methyl-2-(4-trifluoromethyl-phenyl)-thiazol-5-yl]-propan-1-ol, (−)-(S)-1-[4-methyl-2-(4-trifluoromethyl-phenyl)-thiazol-5-yl]-propan-1-ol was obtained by saponification of (+)-(R)-methoxy-phenyl-acetic acid (S)-1-[4-methyl-2-(4-trifluoromethyl-phenyl)-thiazol-5-yl]-propyl ester.

C14H14F3NOS (301.33), MS (ESI): 302.2 (M+H$^+$).

1-[4-Methyl-2-(4-trifluoromethyl-phenyl)-thiazol-5-yl]-pentan-1-ol

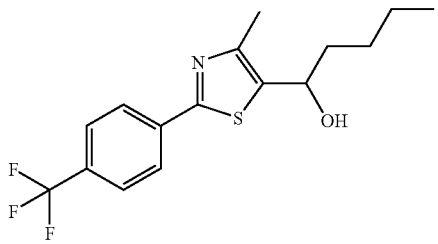

According to the method described for 1-[4-Methyl-2-(4-trifluoromethyl-phenyl)-thiazol-5-yl]-ethanol, 1-[4-Methyl-2-(4-trifluoromethyl-phenyl)-thiazol-5-yl]-pentan-1-ol was obtained from 4-Methyl-2-(4-trifluoromethyl-phenyl)-thiazole-5-carbaldehyde and Butylmagnesiumbromide.

C16H18F3NOS (329.39), MS (ESI): 330.1 (M+H$^+$), Rf (n-heptane:ethyl acetate=1:1)=0.46.

1-[4-Methyl-2-(4-trifluoromethyl-phenyl)-thiazol-5-yl]-2-phenyl-ethanol

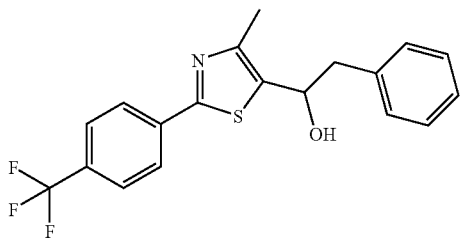

According to the method described for 1-[4-Methyl-2-(4-trifluoromethyl-phenyl)-thiazol-5-yl]-ethanol, 1-[4-Methyl-2-(4-trifluoromethyl-phenyl)-thiazol-5-yl]-2-phenyl-ethanol was obtained from 4-Methyl-2-(4-trifluoromethyl-phenyl)-thiazole-5-carbaldehyde and benzylmagnesiumbromide.

C19H16F3NOS (363.40), MS (ESI): 364.0 (M+H$^+$).

1-[4-Methyl-2-(4-trifluoromethyl-phenyl)-thiazol-5-yl]-2-pyridin-2-yl-ethanol

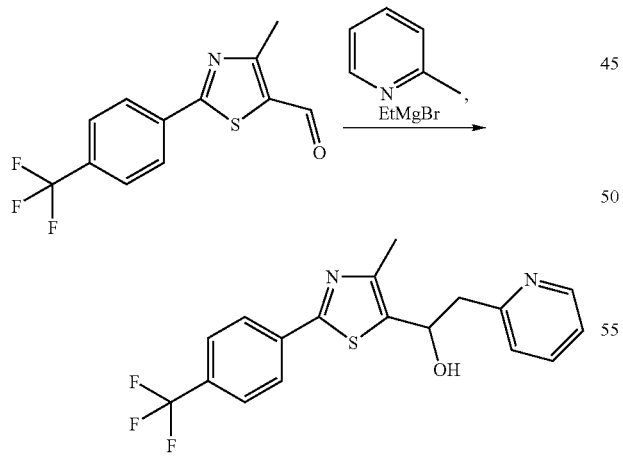

1.47 ml of a 3M solution of ethylmagnesiumbromide was added to a solution of 0.44 ml 2-picoline in 40 ml dibutylether. The reaction mixture was stirred at 140° C. for forty minutes. Then an argon current was bubbled through the reaction mixture for ten minutes. The mixture was cooled to 70° C. 1.0 g 4-Methyl-2-(4-trifluoromethyl-phenyl)-thiazole-5-carbaldehyde, dissolved in 50 ml tetrahydrofuran, were added and stirred at room temperature for thirty minutes. The reaction mixture was poured on ice and extracted three times with portions of 80 ml ethyl acetate. The combined organic layers were dried over MgSO4. The solvent was evaporated in vacuo obtain 1.49 g crude 1-[4-Methyl-2-(4-trifluoromethyl-phenyl)-thiazol-5-yl]-2-pyridin-2-yl-ethanol as an oil. This material was used without purification.

C18H15F3N2OS (364.39), MS (ESI): 365.1 (M+H+), Rf(n-heptane:ethyl acetate=1.1)=0.08.

2-(4-Fluoro-phenyl)-1-[4-methyl-2-(4-trifluoromethyl-phenyl)-thiazol-5-yl]-ethanol

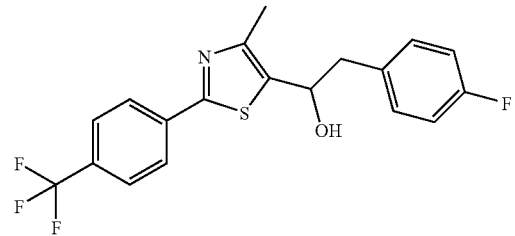

According to the method described for 1-[4-Methyl-2-(4-trifluoromethyl-phenyl)-thiazol-5-yl]-ethanol, 2-(4-Fluoro-phenyl)-1-[4-methyl-2-(4-trifluoromethyl-phenyl)-thiazol-5-yl]-ethanol was obtained from 4-Methyl-2-(4-trifluoromethyl-phenyl)-thiazole-5-carbaldehyde and 4-fluorbenzylmagnesiumbromide.

C13H13F3N2OS (302.32), MS (ESI): 303.1 (M+H+).

[4-Methyl-2-(4-trifluoromethyl-phenyl)-thiazol-5-yl]-phenyl-methanol

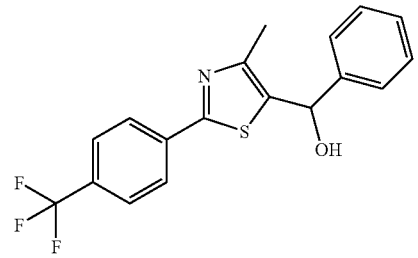

According to the method described for 1-[4-Methyl-2-(4-trifluoromethyl-phenyl)-thiazol-5-yl]-ethanol, [4-Methyl-2-(4-trifluoromethyl-phenyl)-thiazol-5-yl]-phenyl-methanol was obtained from 4-Methyl-2-(4-trifluoromethyl-phenyl)-thiazole-5-carbaldehyde and phenylmagnesiumchloride.

C19H15F4NOS (381.40), MS (ESI): 382.0 (M+H+).

1-[4-Methyl-2-(4-trifluoromethyl-phenyl)-thiazol-5-yl]-3-phenyl-prop-2-yn-1-ol

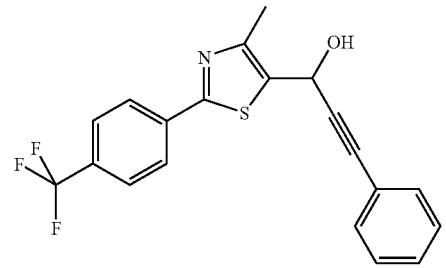

According to the method described for 1-[4-Methyl-2-(4-trifluoromethyl-phenyl)-thiazol-5-yl]-ethanol, 1-[4-Methyl-2-(4-trifluoromethyl-phenyl)-thiazol-5-yl]-3-phenyl-prop-2-yn-1-ol was obtained from 4-Methyl-2-(4-trifluoromethylphenyl)-thiazole-5-carbaldehyde and phenylethynylmagnesiumbromide.

C20H14F3NOS (373.40), MS (ESI): 374.0 (M+H+).

1-[4-Methyl-2-(4-trifluoromethyl-phenyl)-thiazol-5-yl]-3-Phenyl-propan-1-ol

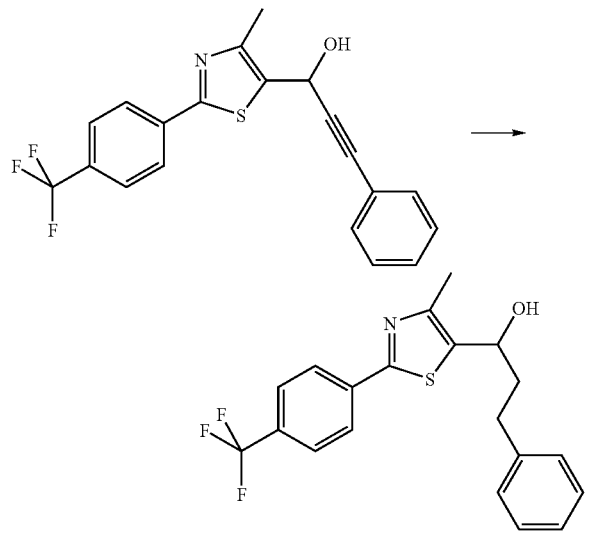

1-[4-Methyl-2-(4-trifluoromethyl-phenyl)-thiazol-5-yl]-3-phenyl-propan-1-ol was obtained by hydrogenation of 1-[4-Methyl-2-(4-trifluoromethyl-phenyl)-thiazol-5-yl]-3-phenyl-prop-2-yn-1-ol in methanol with palladium on carbon (10%) in a hydrogen atmosphere overnight.

C20H18F3NOS (377.43), MS (ESI): 376.1 (M+H+).

1-[4-Methyl-2-(4-trifluoromethyl-phenyl)-oxazol-5-yl]-3-phenyl-prop-2-yn-1-ol

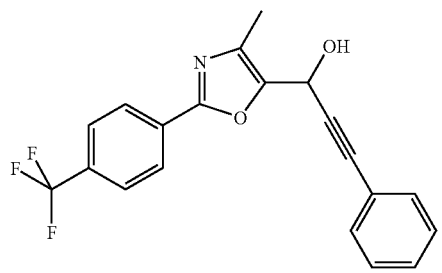

According to the method described for 1-[4-Methyl-2-(4-trifluoromethyl-phenyl)-thiazol-5-yl]-ethanol, 1-[4-Methyl-2-(4-trifluoromethyl-phenyl)-oxazol-5-yl]-3-phenyl-prop-2-yn-1-ol was obtained from 4-Methyl-2-(4-trifluoromethyl-phenyl)-oxazole-5-carbaldehyde (obtained from [4-Methyl-2-(4-trifluoromethyl-phenyl)-oxazol-5-yl]-methanol[3] and manganese (IV) dioxide according to the synthesis described for 4-methyl-2-(4-trifluoromethyl-phenyl)-thiazole-5-carbaldehyde) and phenylethynylmagnesiumbromide.

[3] Bioorganic & Medicinal Chemistry Letters (2003), 13(9), 1517-1521.

C20H14F3NO2 (357.34), MS (ESI): 358.1 (M+H+).

1-[4-Methyl-2-(4-trifluoromethyl-phenyl)-oxazol-5-yl]-3-phenyl-Propan-1-ol

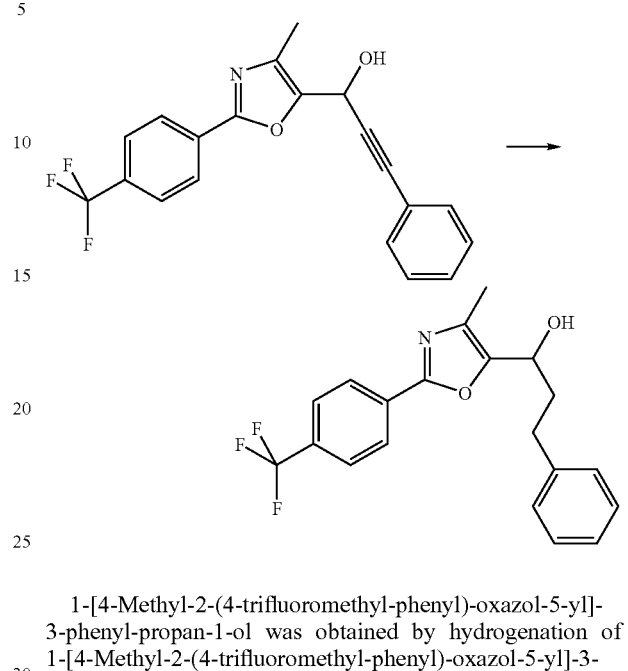

1-[4-Methyl-2-(4-trifluoromethyl-phenyl)-oxazol-5-yl]-3-phenyl-propan-1-ol was obtained by hydrogenation of 1-[4-Methyl-2-(4-trifluoromethyl-phenyl)-oxazol-5-yl]-3-phenyl-prop-2-yn-1-ol in methanol with palladium on carbon (10%) in a hydrogen atmosphere overnight.

C20H18F3NO2 (361.37), MS (ESI): 362.0 (M+H+).

Building block synthesis according to process E:

2,2,2-Trifluoro-1-[4-methyl-2-(4-trifluoromethyl-phenyl)-thiazol-5-yl]-ethanol

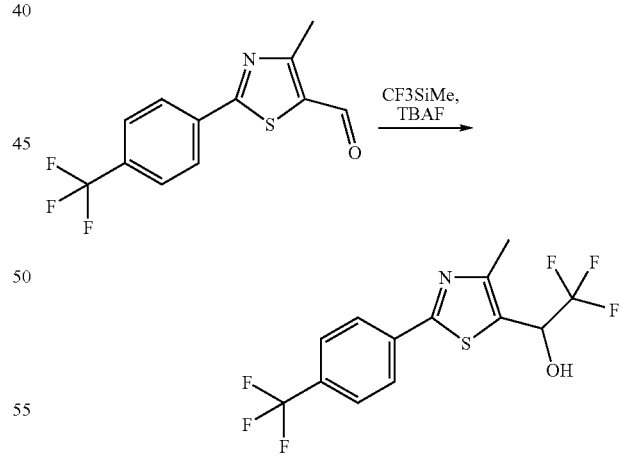

To an ice cooled solution of 1.0 g 4-Methyl-2-(4-trifluoromethyl-phenyl)-thiazole-5-carbaldehyde and 0.55 ml (trifluoromethyl)trimethylsilane in 10 ml tetrahydrofuran were added 100 mg tetrabutylammoniumfluoride. The reaction mixture was stirred at room temperature for thirty minutes. Then 20 ml 2NHCL were added and the mixture stirred at room temperature for thirty minutes. The mixture was extracted three times with portions of 50 ml ethyl acetate. The combined organic layers were dried over MgSO4. The solvent was evaporated in vacuo to obtain 2,2,2-Trifluoro-1-[4-methyl-2-(4-trifluoromethyl-phenyl)-thiazol-5-yl]-ethanol as a solid.

C13H9F6NOS (341.28), MS (ESI): 342.0 (M+H⁺), Rf(n-heptane:ethyl acetate=1:1)=0.54.

2,2-Difluoro-1-[4-methyl-2-(4-trifluoromethyl-phenyl)-thiazol-5-yl]-but-3-en-1-ol

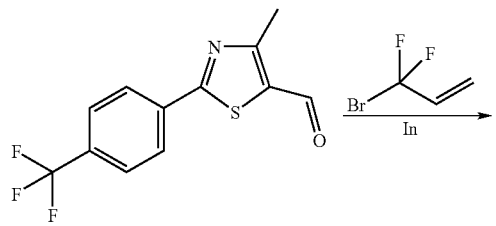

To a solution of 1.0 g 4-Methyl-2-(4-trifluoromethyl-phenyl)-thiazole-5-carbaldehyde and 868 mg 3-bromo-3,3-difluorpropene in 10 ml dimethylformamide 425 mg Indium were added and the resulting suspension was stirred in an ultrasonic bath for two hours. Then 20 ml 1 N hydrochloric acid were added and the mixture stirred at room temperature for thirty minutes. The mixture was extracted three times with portions of 50 ml ethyl acetate. The combined organic layers were dried over MgSO4. The solvent was evaporated in vacuo. The resulting residue was purified by reversed phase HPLC to obtain 740 mg 2,2-Difluoro-1-[4-methyl-2-(4-trifluoromethyl-phenyl)-thiazol-5-yl]-but-3-en-1-ol as a colorless lyophilisate.

C15H12F5NOS (349.32), MS (ESI): 350.1 (M+H+), Rf(n-heptane:ethyl acetate=1:1)=0.52.

2,2-Difluoro-1-[4-methyl-2-(4-trifluoromethyl-phenyl)-thiazol-5-yl]-butan-1-ol

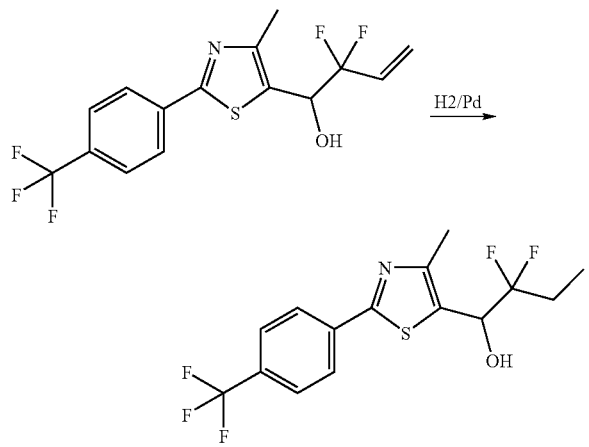

740 mg 2,2-Difluoro-1-[4-methyl-2-(4-trifluoromethyl-phenyl)-thiazol-5-yl]-but-3-en-1-ol were dissolved in 50 ml ethyl acetate. 50 mg palladium (5% on charcoal) were added and the reaction mixture stirred at room temperature under a hydrogen atmosphere. After three hours the catalyst was filtered off and the filtrate evaporated in vacuo to obtain 720 mg 2,2-Difluoro-1-[4-methyl-2-(4-trifluoromethyl-phenyl)-thiazol-5-yl]-butan-1-ol as a white solid.

C15H14F5NOS (351.34), MS (ESI): 352.1 (M+H+).

2-Cyclopropyl-2,2-difluoro-1-[4-methyl-2-(4-trifluoromethyl-phenyl)-thiazol-5-yl]-ethanol

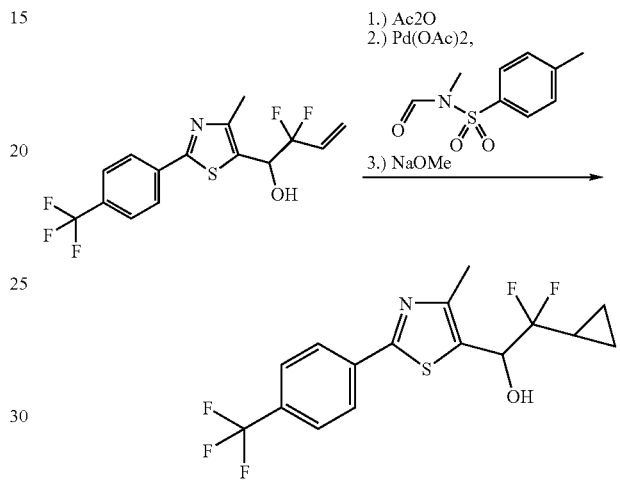

To an ice cooled solution of 365 mg 2,2-Difluoro-1-[4-methyl-2-(4-trifluoromethyl-phenyl)-thiazol-5-yl]-but-3-en-1-ol in 10 ml pyridine were added 5 ml acetic acid anhydride. The ice bath was removed and the reaction mixture stirred at room temperature for one hour. The ice was added and the reaction mixture diluted by addition of 100 ml dichloromethane. The organic layer was separated and washed with 50 ml water, 1 M HCl, saturated NaHCO3 solution and brine. Then the organic layer was dried over MgSO4 and the solvent removed in vacuo. The resulting residue was dissolved in 30 ml diethyl ether (flask 1). 246 mg palladium, (II) acetate were added and the mixture cooled in an ice bath. In a second flask 4.0 g N-methyl-N-nitroso-p-toluenesulfonamide were suspended in 30 ml ethanol. An argon current was bubbled permanently through flask 2 and afterwards through flask 1. 2N NaOH was added dropwise to flask 2 until dissolution of N-methyl-N-nitroso-p-toluenesulfonamide, then the argon current was stopped. The reaction mixture (flask 1) was stirred at 0° C. for an additional hour. Then 10 ml acetic acid were added and the reaction mixture diluted by addition of 80 ml ethyl acetate. The organic layer was washed with brine and dried over MgSO4. The solvent was removed in vacuo. The resulting residue was dissolved in 20 ml methanol, 1 ml sodium methylate solution (30%) were added and the reaction mixture was stirred at room temperature for one hour. The reaction mixture was then neutralized by addition of acetic acid, the solvent was removed in vacuo and the residue purified by reversed phase HPLC to obtain 120 mg 2-Cyclopropyl-2,2-difluoro-1-[4-methyl-2-(4-trifluoromethyl-phenyl)-thiazol-5-yl]-ethanol as lyophilisate.

C16H14F5NOS (363.35), MS (ESI): 364.1 (M+H+).

2-(4-Difluoromethyl-phenyl)-2,2-difluoro-1-[4-methyl-2-(4-trifluoromethyl-phenyl)-thiazol-5-yl]-ethanol

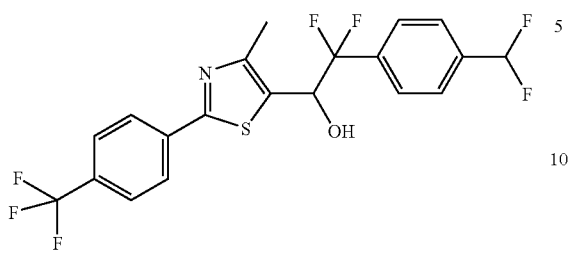

To a solution of 1.0 g 4-Methyl-2-(4-trifluoromethyl-phenyl)-thiazole-5-carbaldehyde and 1.42 g 4-(bromodifluoromethyl)-1-(difluoromethyl)benzene in 10 ml dimethylformamide 508 mg Indium were added and the resulting suspension was stirred in an ultrasonic bath for twelve hours. Then additional 1.42 g 4-(bromodifluoromethyl)-1-(difluoromethyl) benzene and 508 mg Indium were added and the resulting suspension was stirred in an ultrasonic bath for additional twelve hours. Then 20 ml 1 N hydrochloric acid were added and the mixture stirred at room temperature for thirty minutes. The mixture was extracted three times with portions of 50 ml ethyl acetate. The combined organic layers were dried over MgSO4. The solvent was evaporated in vacuo. The resulting residue was purified by reversed phase HPLC to obtain 620 mg 2-(4-Difluoromethyl-phenyl)-2,2-difluoro-1-[4-methyl-2-(4-trifluoromethyl-phenyl)-thiazol-5-yl]-ethanol as a colorless lyophilisate.

C20H14F7NOS (449.39), MS (ESI): 450.1 (M+H+),

Building block synthesis according to process N:

1-[2-(4-Trifluoromethyl-phenyl)-4-(4-trifluoromethyl-piperidin-1-ylmethyl)-thiazol-5-yl]-propan-1-ol

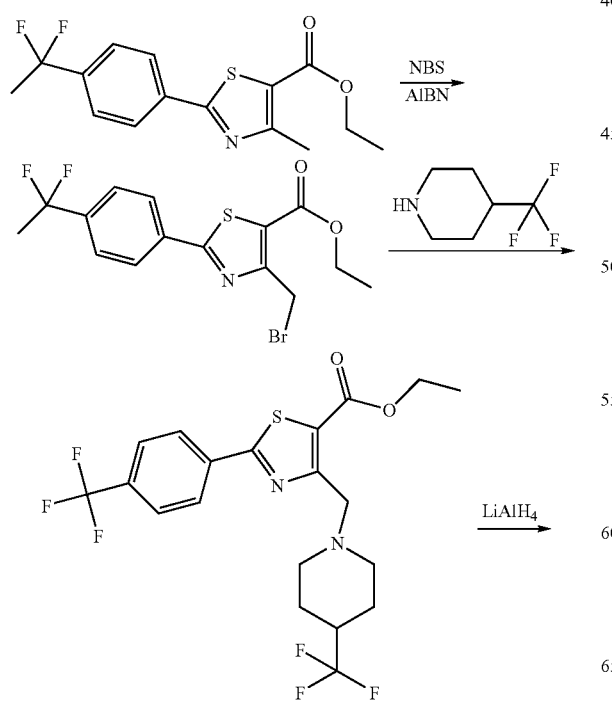

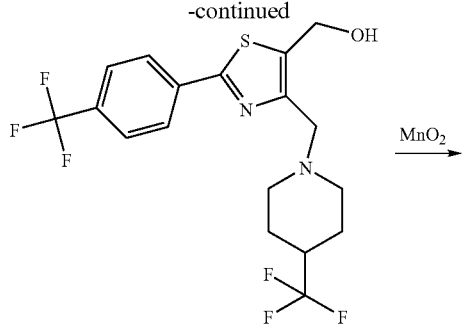

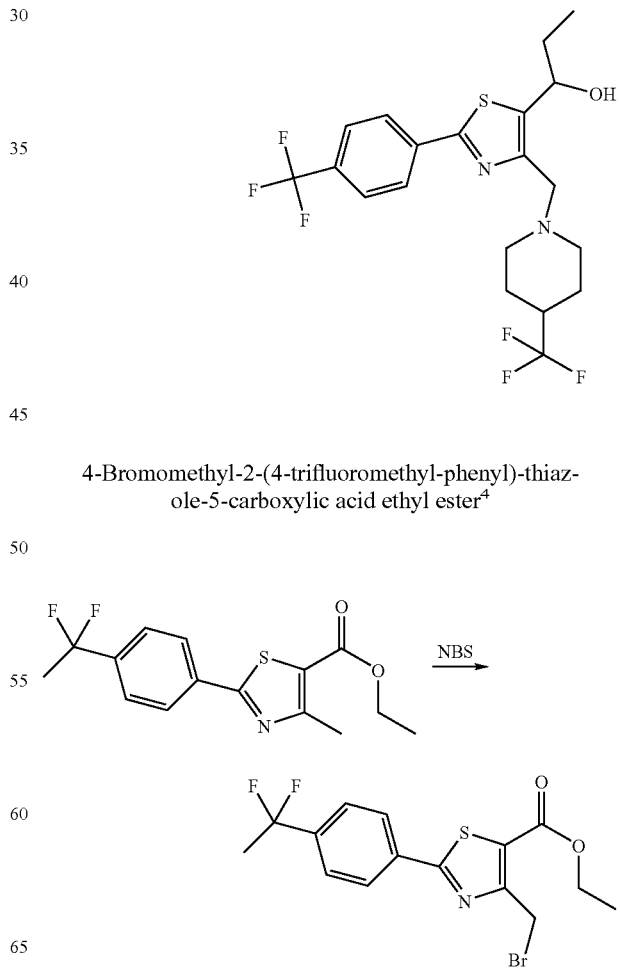

4-Bromomethyl-2-(4-trifluoromethyl-phenyl)-thiazole-5-carboxylic acid ethyl ester[4]

To a solution of 200 g of commercially available 4-methyl-2-(4-trifluoromethyl-phenyl)-thiazole-5-carboxylic acid ethyl ester in 1.6 L of dichloromethane were added 20.5 g of benzoyl peroxide and 124 g of NBS. The resulting mixture was refluxed in the dark for 22 h. After cooling to 0° C., the mixture was filtered. The filtrate was concentrated to half volume under reduced pressure, washed with water, dried over magnesium sulfate, filtered and concentrated under reduced pressure to give a white solid. The solid was recrystallized in 900 mL of diisopropyl ether 80/dichloromethane 20 to give a first crop of 101 g of 4-bromomethyl-2-(4-trifluoromethyl-phenyl)-thiazole-5-carboxylic acid ethyl ester. The filtrate was concentrated under reduced pressure then recrystallized in 300 mL of diisopropyl ether 90/dichloromethane 10 to give a second crop of 72 g. A total of 173 g of 4-bromomethyl-2-(4-trifluoromethyl-phenyl)-thiazole-5-carboxylic acid ethyl ester was obtained as a white solid.
[4] WO02067912

C14H11BrF3NO2S (394.21), MS (EI): 394 (M+).

2-(4-Trifluoromethyl-phenyl)-4-(4-trifluoromethyl-piperidin-1-ylmethyl)-thiazole-5-carboxylic acid ethyl ester

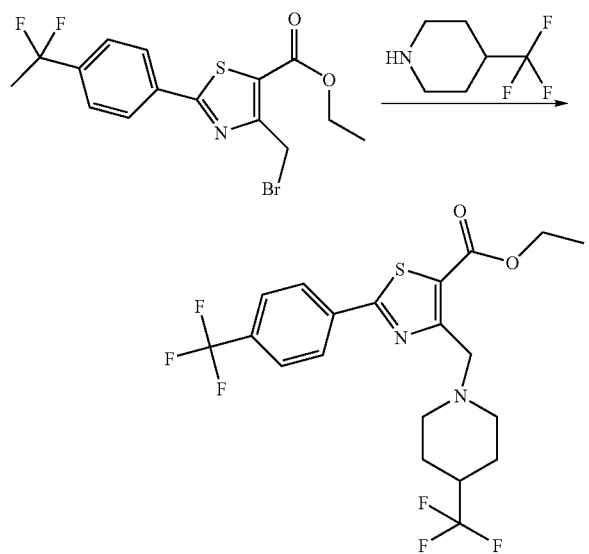

To a solution of 107.7 g of 4-trifluoromethyl piperidine hydrochloride in 450 mL of water were added 2.7 L of acetonitrile, 224 g of 4-bromomethyl-2-(4-trifluoromethyl-phenyl)-thiazole-5-carboxylic acid ethyl ester and 157 g of potassium carbonate. The resulting mixture was heated to 40° C. for 2 h, allowed to cool to room temperature then concentrated under reduced pressure. The residue was taken into 2 L of dichloromethane then washed twice with 500 mL of water. The organic layer was dried over magnesium sulfate, filtered, and concentrated under reduced pressure. The crude product was purified by column chromatography on silica gel (gradient of dichloromethane/ethanol from 100/0 to 90/10) followed by washing of the collected solid with diisopropyl ether to give 212 g of 2-(4-trifluoromethyl-phenyl)-4-(4-trifluoromethyl-piperidin-1-ylmethyl)-thiazole-5-carboxylic acid ethyl ester as a white solid.

C20H20F6N2O2S (466.45), MS (EI): 466 (M+).

[2-(4-Trifluoromethyl-phenyl)-4-(4-trifluoromethyl-piperidin-1-ylmethyl)-thiazol-5-yl]-methanol

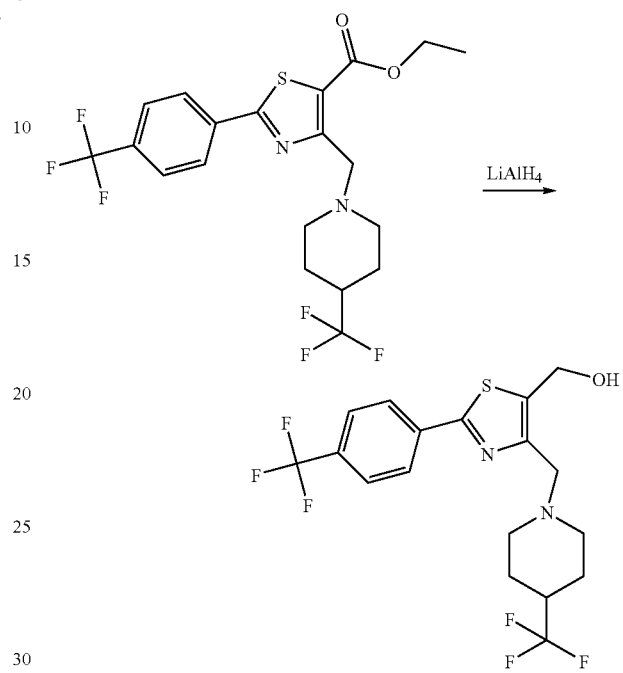

To a solution of 220 g of 2-(4-trifluoromethyl-phenyl)-4-(4-trifluoromethyl-piperidin-1-ylmethyl)-thiazole-5-carboxylic acid ethyl ester in 2.2 L of tetrahydrofuran at 0° C. was dropwise added 250 mL of a 2M solution of lithium aluminum hydride in tetrahydrofuran. The resulting mixture was stirred for 1 h allowing it to warm up to room temperature then slowly poured into 1 L of cold water and extracted twice with 1.5 L of ethyl acetate. The combined organic extracts were dried over magnesium sulfate, filtered, and concentrated under reduced pressure. The crude product was washed with 500 mL of hot diisopropyl ether then purified by column chromatography on silica gel (gradient of dichloromethane/ethanol from 100/0 to 90/10) to give 163 g of [2-(4-trifluoromethyl-phenyl)-4-(4-trifluoromethyl-piperidin-1-ylmethyl)-thiazol-5-yl]-methanol as a white solid.

C18H18F6N2OS (424.41), MS (ESI): 425 (M+H+).

2-(4-Trifluoromethyl-phenyl)-4-(4-trifluoromethyl-piperidin-1-ylmethyl)-thiazole-5-carbaldehyde

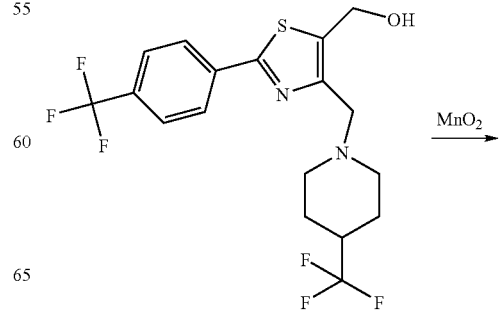

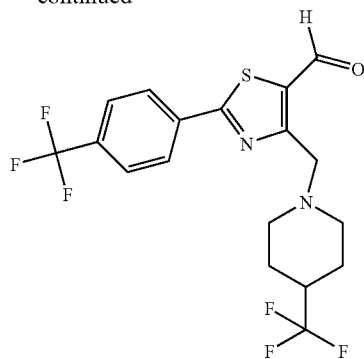

To a solution of 1 g of [[2-(4-trifluoromethyl-phenyl)-4-(4-trifluoromethyl-piperidin-1-ylmethyl)-thiazol-5-yl]-methanol in 7 ml of dichloromethane was added 2.35 g of manganese(IV)oxide (activated with charcoal). The resulting mixture was heated under reflux for four hours. The cooled reaction mixture was filtered through a pad of celite. The filtrate was concentrated under reduced pressure and purified by column chromatography on silica gel (heptane 80/ethyl acetate 20) to give 0.53 g of 2-(4-trifluoromethyl-phenyl)-4-(4-trifluoromethyl-piperidin-1-ylmethyl)-thiazole-5-carbaldehyde.

C18H16F6N2OS (422.39), MS (ESI): 423.0 (M+H$^+$).

1-[2-(4-Trifluoromethyl-phenyl)-4-(4-trifluoromethyl-piperidin-1-ylmethyl)-thiazol-5-yl]-propan-1-ol

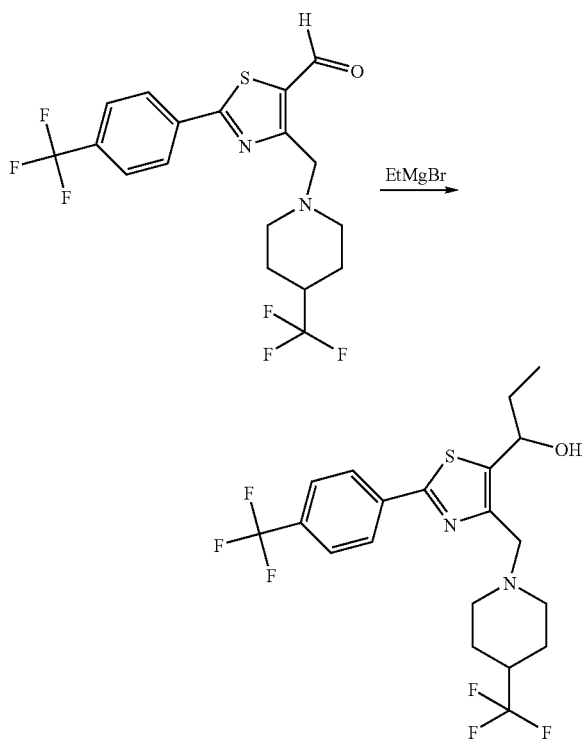

To a solution of 530 mg of 2-(4-trifluoromethyl-phenyl)-4-(4-trifluoromethyl-piperidin-1-ylmethyl)-thiazole-5-carbaldehyde in 43 ml tetrahydrofuran at 0° C. was slowly added 2.2 ml of a molar solution of ethylmagnesium bromide in tert-butyl methyl ether. The reaction mixture was stirred at 0° C. for one hour then poured onto an aqueous solution of KH2PO4 and extracted with dichloromethane. The combined organic extracts were dried over magnesium sulfate, filtered, and concentrated under reduced pressure to give 545 mg 1-[2-(4-trifluoromethyl-phenyl)-4-(4-trifluoromethyl-piperidin-1-ylmethyl)-thiazol-5-yl]-propan-1-ol which was used without further purification.

C20H22F6N2OS (452.47), MS (ESI): 453 (M+H$^+$).

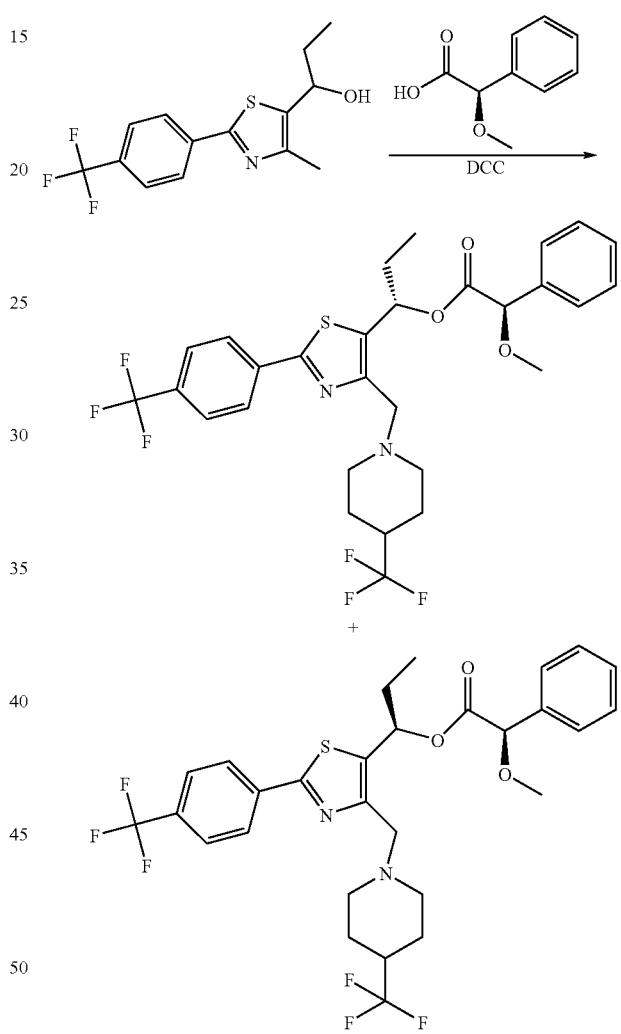

To a solution of 3.78 g of racemic 1-[2-(4-trifluoromethyl-phenyl)-4-(4-trifluoromethyl-piperidin-1-ylmethyl)-thiazol-5-yl]-propan-1-ol in 66 mL of tetrahydrofuran was added 1.5 g of (R)-(−)-α-methoxyphenyl acetic acid, 9 mL of a molar solution of N,N-dicyclohexylcarbodiimide in dichloromethane and a few mg of N,N-dimethylaminopyridine. The resulting mixture was stirred at room temperature overnight then filtered. The filtrate was concentrated under reduced pressure and the diastereomers were separated by column chromatography on silica gel (gradient from dichloromethane 100 to dichloromethane 90/ethyl acetate 10) to give: 1.06 g of (−)-(R)-methoxy-phenyl-acetic acid (S)-1-[2-(4-trifluoromethyl-phenyl)-4-(4-trifluoromethyl-piperidin- 1-ylmethyl)-thiazol-5-yl]-propyl ester (less polar fraction) according to ¹H NMR analysis²

C29H30F6N2O3S (600.62), MS (ESI): 601.2 (M+H⁺), and 0.67 g of (+)-(R)-methoxy-phenyl-acetic acid (R)-1-[2-(4-trifluoromethyl-phenyl)-4-(4-trifluoromethyl-piperidin-1-ylmethyl)-thiazol-5-yl]-propyl ester (more polar fraction) according to ¹H NMR analysis²

C29H30F6N2O3S (600.62), MS (ESI): 601.2 (M+H⁺).

(R)-1-[2-(4-Trifluoromethyl-phenyl)-4-(4-trifluoromethyl-piperidin-1-ylmethyl)-thiazol-5-yl]-propan-1-ol

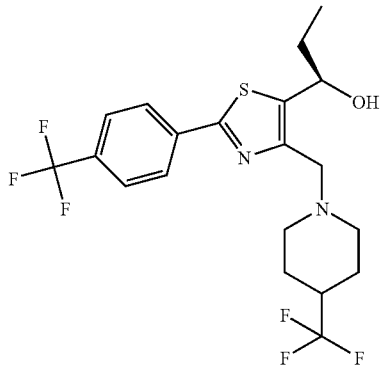

To a solution of 0.67 g of (R)-methoxy-phenyl-acetic acid (R)-1-[2-(4-trifluoromethyl-phenyl)-4-(4-trifluoromethyl-piperidin-1-ylmethyl)-thiazol-5-yl]-propyl ester in 2.5 mL of tetrahydrofuran and 2.5 mL of ethanol at 0° C. was dropwise added 3.5 mL of a molar solution of sodium hydroxide in 2.7 mL of water. The resulting mixture was stirred at 0° C. for 15 minutes then 0.6 mL of a 5N solution of hydrochloric acid in 2.7 mL of water was added. After removal of the organic solvents under vacuum, the mixture was extracted with dichloromethane, filtered through a silicone treated filter and concentrated under reduced pressure. The residue was purified by column chromatography on silica gel (dichloromethane 90/ethyl acetate 10) to give 270 mg of (R)-1-[2-(4-trifluoromethyl-phenyl)-4-(4-trifluoromethyl-piperidin-1-ylmethyl)-thiazol-5-yl]-propan-1-ol.

C20H22F6N2OS (452.46), MS (ESI): 453.2 (M+H⁺).

(S)-1-[2-(4-Trifluoromethyl-phenyl)-4-(4-trifluoromethyl-piperidin-1-ylmethyl)-thiazol-5-yl]-propan-1-ol

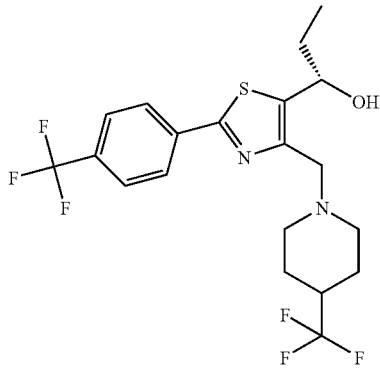

According to the method described for (R)-1-[2-(4-trifluoromethyl-phenyl)-4-(4-trifluoromethyl-piperidin-1-ylmethyl)-thiazol-5-yl]-propan-1-ol, (S)-1-[2-(4-trifluoromethyl-phenyl)-4-(4-trifluoromethyl-piperidin-1-ylmethyl)-thiazol-5-yl]-propan-1-ol was obtained by saponification of (R)-methoxy-phenyl-acetic acid (S)-1-[2-(4-trifluoromethyl-phenyl)-4-(4-trifluoromethyl-piperidin-1-ylmethyl)-thiazol-5-yl]-propyl ester.

C20H22F6N2OS (452.46), MS (ESI): 453.1 (M+H⁺).

Building Block Synthesis According to Process F:

4-Bromomethyl-2-chloro-benzonitrile

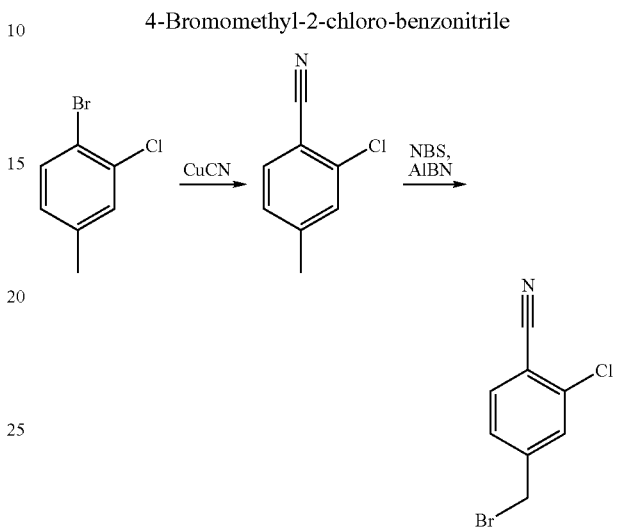

2-Chloro-4-methyl-benzonitrile

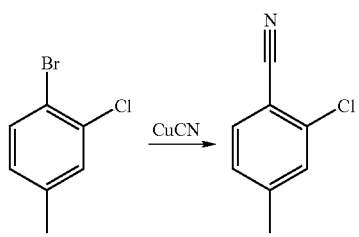

25.0 g 4-bromo-3-chlorotoluene and 21.8 g copper (I) cyanide were dissolved in 200 ml dimethylformamide and stirred at 150° C. for three hours. The cooled reaction mixture was diluted by addition of 300 ml ethyl acetate and washed three times with portions of 150 ml saturated NH4Cl solution. The precipitates were filtered off and the filtrate dried over MgSO4 and then reduced in vacuo to obtain 17.3 g 2-Chloro-4-methyl-benzonitrile. This material was used without purification in the next step.

C8H6ClN (151.60).

4-Bromomethyl-2-chloro-benzonitrile

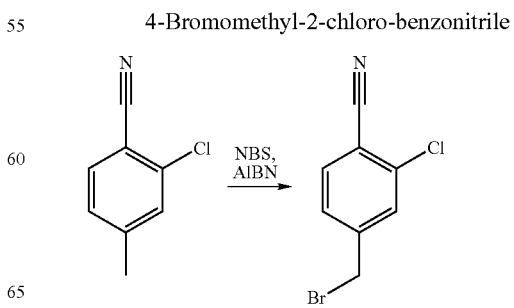

17.3 g 2-Chloro-4-methyl-benzonitrile were dissolved in 50 ml tetrachloromethane and heated to reflux. A mixture of 24.3 g N-bromosuccinimide and 7.48 g 2,2'-azobis(2-methylpropionitrile) were added in five portions over a period of one hour. The reaction mixture was heated under reflux for additional three hours. The cooled reaction mixture was then filtered through a celite pad. The filtrate was washed with 100 ml saturated NaHCO3 solution, dried over MgSO4 and the solvent was removed in vacuo. The resulting residue was dissolved in 200 ml tetrahydrofuran and cooled in an ice bath to 0° C. 88.0 ml diethyl phosphite were added, followed by the addition of 117.0 ml N,N-diisopropylethylamine. The cooling bath was removed and the reaction mixture stirred at room temperature for four hours. The reaction mixture was poured in 400 ml 50% NaHCO3 solution and extracted with 400 ml diethylether. The organic layer was separated and washed with 200 ml 50% NaHCO3 solution and 200 ml water and then dried over MgSO4. The solvent was removed in vacuo. The resulting residue was purified on silica gel with the eluent n-heptane:ethyl acetate=19:1 to obtain 13.0 g 4-Bromomethyl-2-chloro-benzonitrile as a solid.

C8H5BrClN (230.49), Rf(n-heptane:ethyl acetate=4:1)=0.31.

8-Methyl-quinoline-5-carbonitrile

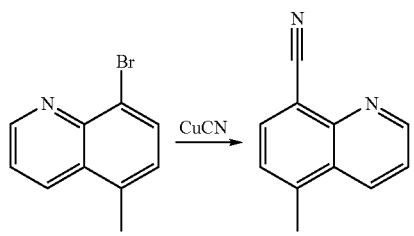

4.0 g 8-Bromo-5-methyl-quinoline and 1.69 g copper (I) cyanide were dissolved in 16 ml dimethylformamide and stirred at 200° C. for thirty minutes under microwave irradiation. The cooled reaction mixture was poured in 50 ml 2N HCL and extracted with 100 ml ethyl acetate. The organic layer was washed with 50 ml 2N HCl and 30 ml brine and then dried over MgSO4. The solvent was removed in vacuo. The resulting residue was purified on silica gel with the eluent n-heptane ethyl acetate=2:1 to obtain 3.0 g 8-Methyl-quinoline-5-carbonitrile.

C11H8N2 (168.20), Rf(n-heptane:ethyl acetate=4:1)=0.20.

8-Bromomethyl-quinoline-5-carbonitrile

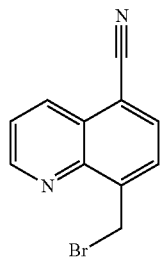

According to the method described for 4-Bromomethyl-2-chloro-benzonitrile, 8-Bromomethyl-quinoline-5-carbonitrile was obtained from 8-Methyl-quinoline-5-carbonitrile.

C11H7BrN2 (247.10), Rf(n-heptane:ethyl acetate=4:1)=0.24.

4-Bromomethyl-naphthalene-1-carbonitrile

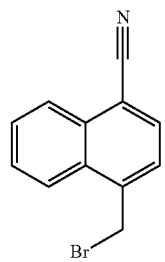

According to the method described for 4-Bromomethyl-2-chloro-benzonitrile, 4-Bromomethyl-naphthalene-1-carbonitrile was obtained from commercially available 1-cyano-4-methylnaphthalene.

C12H8BrN (246.11), Rf(n-heptane:ethyl acetate=4:1)=0.38.

2-Bromo-4-bromomethyl-benzonitrile

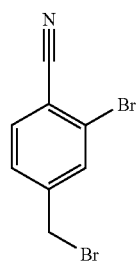

According to the method described for 4-Bromomethyl-2-chloro-benzonitrile, 2-Bromo-4-bromomethyl-benzonitrile was obtained from commercially available 2-Bromo-4-methyl-benzonitrile.

C8H5Br2N (274.94), Rf(n-heptane:ethyl acetate=4:1)=0.30.

6-Bromomethyl-2-chloro-nicotinonitrile

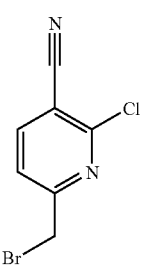

According to the method described for 4-Bromomethyl-2-chloro-benzonitrile, 6-Bromomethyl-2-chloro-nicotinonitrile was obtained from commercially available 2-Chloro-6-methyl-nicotinonitrile.

C7H4BrClN2 (231.48), Rf(n-heptane:ethyl acetate=1:1)=0.48.

4-Bromomethyl-2-fluoro-benzonitrile

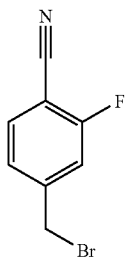

According to the method described for 4-Bromomethyl-2-chloro-benzonitrile, 4-Bromomethyl-2-fluoro-benzonitrile was obtained from commercially available 2-Fluoro-4-methyl-benzonitrile.

C8H5BrFN (214.04), Rf(n-heptane:ethyl acetate=4:1)=0.25.

Building Block Synthesis According to Process G:

4-Fluoro-2-methoxymethyl-benzonitrile

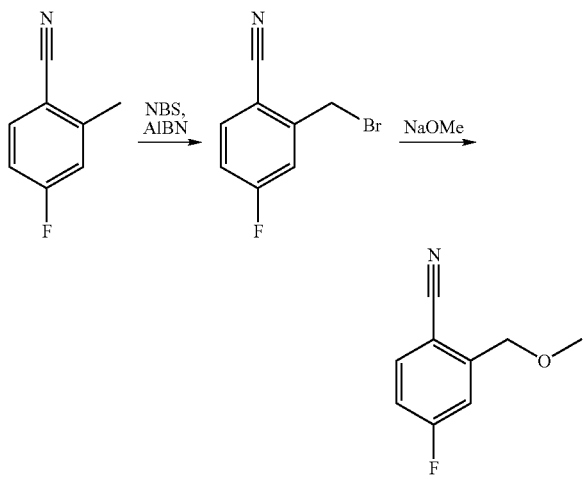

2-Bromomethyl-4-fluoro-benzonitrile

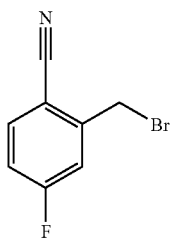

According to the method described for 4-Bromomethyl-2-chloro-benzonitrile, 2-Bromomethyl-4-fluoro-benzonitrile was obtained from commercially available 4-Fluoro-2-methylbenzonitrile.

C8H5BrFN (214.04), Rf(n-heptane:ethyl acetate=4:1)=0.25.

4-Fluoro-2-methoxymethyl-benzonitrile

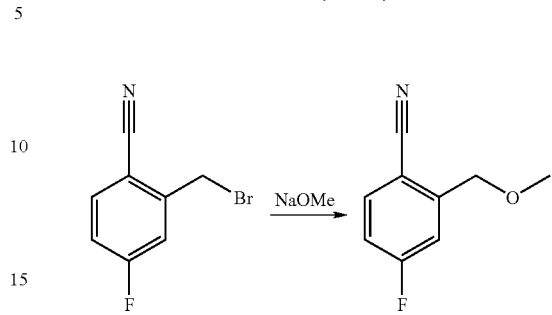

1.0 g 2-Bromomethyl-4-fluoro-benzonitrile were dissolved in a mixture of 10 ml methanol and 10 ml tetrahydrofuran. 500 mg sodium methylate were added and the reaction mixture stirred at room temperature overnight. The reaction mixture was poured on 30 ml water and extracted five times with portion of 25 ml ethyl acetate. The combined organic layers were dried over MgSO4, the solvent removed in vacuo and the resulting residue purified on silica gel with the eluent heptane=>n-heptane:ethyl acetate=9:1 to obtain 526 mg 4-Fluoro-2-methoxymethyl-benzonitrileas an oil.

C9H8FNO (165.17), Rf(n-heptane:ethyl acetate=9:1)=0.25.

4-Fluoro-2-(2,2,2-trifluoro-ethoxymethyl)-benzonitrile

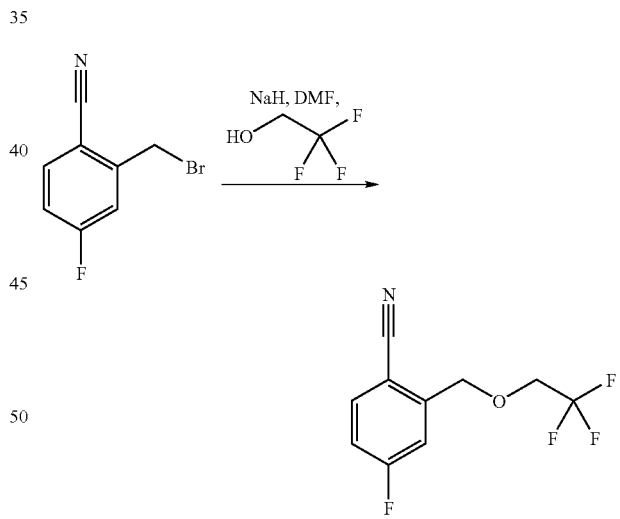

336 µl 2,2,2-Trifluoroethanol were dissolved in 10 ml dimethylformamide. 243 mg sodium hydride were added and the mixture stirred at room temperature for one hour. Then 1.0 g 2-Bromomethyl-4-fluoro-benzonitrile were added in one portion and the reaction mixture was stirred at room temperature for three hours. The reaction mixture was poured on 50 ml water and extracted five times with portion of 25 ml ethyl acetate. The combined organic layers were dried over MgSO4, the solvent removed in vacuo and the resulting residue purified on silica gel with the eluent heptane=>n-heptane:ethyl acetate=4:1 to obtain 750 mg 4-Fluoro-2-(2,2,2-trifluoro-ethoxymethyl)-benzonitrile.

C10H7F4NO (233.17), Rf(n-heptane:ethyl acetate=4:1)= 0.31.

2-Ethoxymethyl-4-fluoro-benzonitrile

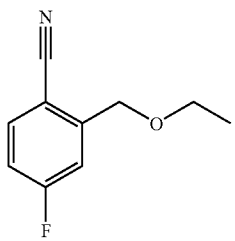

According to the method described for 4-Fluoro-2-(2,2,2-trifluoro-ethoxymethyl)-benzonitrile, 2-Ethoxymethyl-4-fluoro-benzonitrile was obtained from 2-Bromomethyl-4-fluoro-benzonitrile and ethanol.

C10H10FNO (179.20).

Building Block Synthesis According to Process H:

2-Cyclopropyl-4-fluoro-benzonitrile

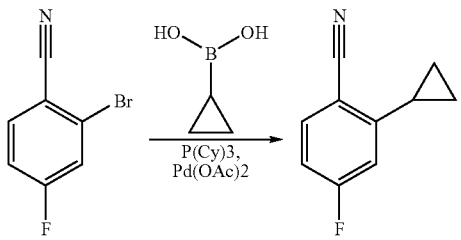

500 mg commercially available 2-Bromo-4-fluorobenzonitrile, 70 mg tricyclohexylphosphine, 2.04 g tri potassium phosphate mono hydrate and 278 mg cyclopropylboronic acid placed in a reaction vessel and 11 ml toluene were added. The mixture was degassed with argon, then 561 mg palladium (II)acetate were added and the reaction mixture stirred at 100° C. for 1.5 hours. To the cooled reaction mixture was added 30 ml water and the mixture was extracted five times with portions of 30 ml ethyl acetate. The combined organic layers were dried over MgSO4, the solvent removed in vacuo and the resulting residue purified on silica gel with the eluent heptane=>n-heptane:ethyl acetate=5:1 to obtain 310 mg 2-Cyclopropyl-4-fluoro-benzonitrile as yellow solid.

C10H8FN (161.18), Rf(n-heptane:ethyl acetate=4:1)= 0.48.

5,4'-Difluoro-biphenyl-2-carbonitrile

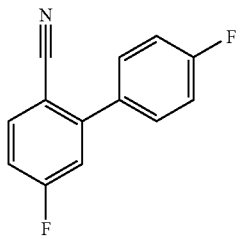

According to the method described for 2-Cyclopropyl-4-fluoro-benzonitrile, 5,4'-Difluoro-biphenyl-2-carbonitrile was obtained from 2-Bromo-4-fluorobenzonitrile and 4-fluorobenzene boronic acid.

C13H7F2N (215.20).

Building Block Synthesis According to Process I:

2-Ethyl-4-fluoro-benzonitrile

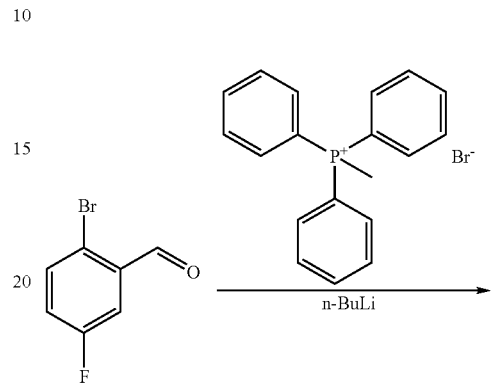

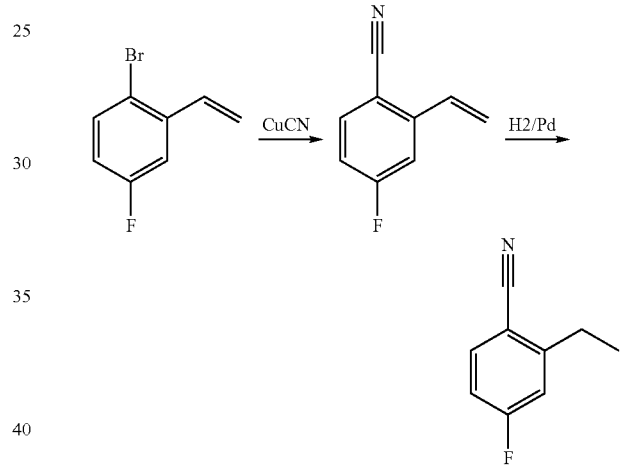

1-Bromo-4-fluoro-2-vinyl-benzene

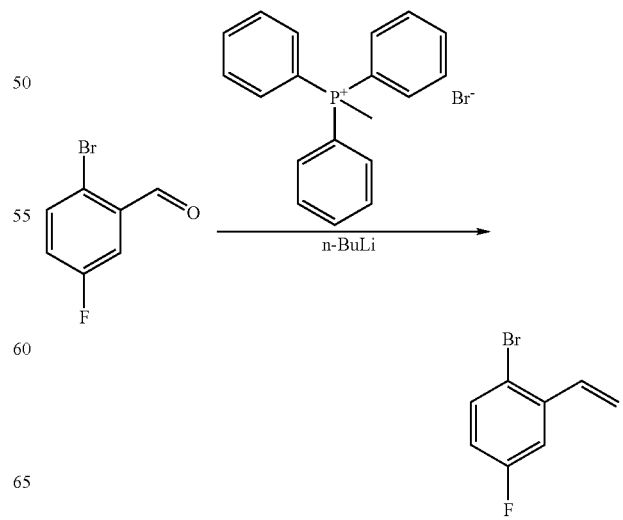

21.12 g Methyltriphenylphosphonium bromide were suspended in 150 ml tetrahydrofuran and cooled in an ice bath. 21.68 ml n-butyl lithium (2.5 M in n-heptane) were added dropwise and the reaction mixture stirred at 0° C. for thirty minutes. Then 10.0 g commercially available 2-bromo-5-fluorobenzaldehyde were added slowly so that the reaction temperature did not exceed +5° C. After completion of the addition the cooling bath was removed and the reaction mixture stirred at room temperature for one hour. The reaction mixture was diluted by addition of 300 ml ethyl acetate and washed three times with portions of 120 ml brine. The organic phase was dried over MgSO4, the solvent removed in vacuo and the resulting residue purified on silica gel with the eluent heptane=>n-heptane:ethyl acetate=9:1 to obtain 7.9 g 1-Bromo-4-fluoro-2-vinyl-benzene as an oil.

C8H6BrF (201.04), Rf(n-heptane:ethyl acetate=9:1)= 0.61.

4-Fluoro-2-vinyl-benzonitrile

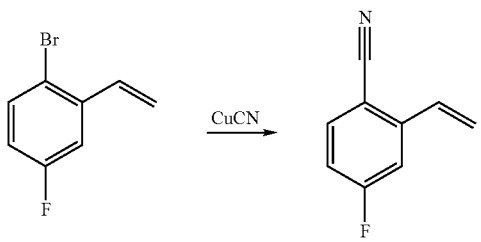

4.0 g 1-Bromo-4-fluoro-2-vinyl-benzene and 1.87 g copper (I) cyanide were dissolved in 16 ml dimethylformamide and heated under microwave irradiation at 200° C. for 25 minutes. The cooled reaction mixture was poured into 200 ml 1 M HCl and extracted five times with portions of 60 ml ethyl acetate. The combined organic layers were washed with 100 ml 1 N HCl, dried over MgSO4, then the solvent was removed in vacuo and the resulting residue purified on silica gel with the eluent heptane=>n-heptane:ethyl acetate=6:1 to obtain 1.77 g 4-Fluoro-2-vinyl-benzonitrile as a solid.

C9H6FN (147.15), Rf(n-heptane:ethyl acetate=4:1)=0.33.

2-Ethyl-4-fluoro-benzonitrile

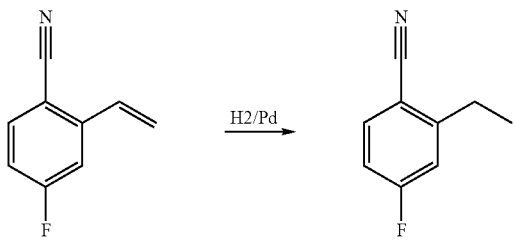

800 mg 4-Fluoro-2-vinyl-benzonitrile were dissolved in 5 ml methanol. 80 mg palladium (10% on charcoal) were added and the reaction was stirred under a hydrogen atmosphere for one hour. The catalyst was filtered off trough a pad of celite. The filtrate was evaporated to obtain 625 mg 2-Ethyl-4-fluoro-benzonitrile.

C9H8FN (149.17), Rf(n-heptane:ethyl acetate=4:1)=0.37.

Building Block Synthesis According to Process L:

2-Difluoromethoxy-4-fluoro-benzonitrile

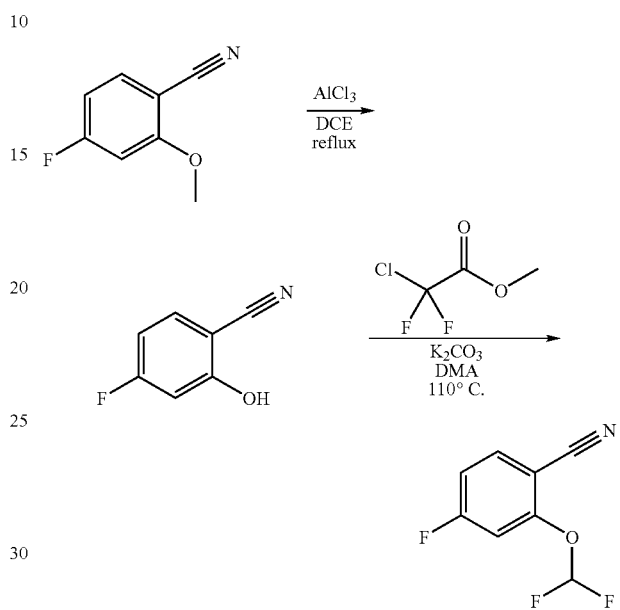

4-Fluoro-2-methoxy-benzonitrile was prepared according to a previous publication:[5]

[5] JP9143139

To a solution of 1 g of 4-fluoro-2-methoxy-benzonitrile in 15 mL of dichloroethane was added 1.1 g of aluminum trichloride. The resulting mixture was refluxed for 1 day then poured slowly into water and extracted with ethyl acetate. The organic extracts were washed twice with 10% aqueous solution of sodium hydroxide. The combined basic layers were washed twice with ethyl acetate, acidified with concentrated aqueous solution of hydrochloric acid and extracted three times with ethyl acetate. The combined organic extracts were washed with water, with brine, dried over magnesium sulfate, filtered and concentrated under reduced pressure to give 0.78 g of 4-fluoro-2-hydroxy-benzonitrile as a white solid.

C7H4FNO (137.11), MS (ESI): 138.17 (M+H$^+$).

To a solution of 4.6 g of 4-fluoro-2-hydroxy-benzonitrile in 15 mL of anhydrous dimethylacetamide were added 6.8 g of methyl chlorodifluoroacetate and 6.5 g of potassium carbonate. The resulting mixture was degassed by bubbling argon through it and heated to 110° C. for 2 h then an additional 6.5 g of methyl chlorodifluoroacetate and 6.5 g of potassium carbonate were added. The resulting mixture was heated to 110° C. for another hour then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 4.78 g of 2-difluoromethoxy-4-fluoro-benzonitrile as a yellowish liquid.

C8H4F3NO (187.12), MS (ESI): 188.0 (M+H⁺).

2-Difluoromethoxy-4,5-difluoro-benzonitrile

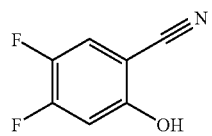 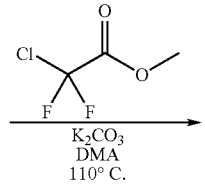

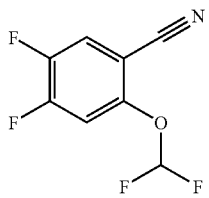

To a solution of 1 g of commercially available 4,5-difluoro-2-hydroxy-benzonitrile in 5 mL of anhydrous dimethylacetamide were added 1.3 g of methyl chlorodifluororacetate and 1.28 g of potassium carbonate. The resulting mixture was degassed by bubbling argon through it and heated to 110° C. for 1.5 h then concentrated under reduced pressure. The residue was taken into ethyl acetate, washed twice with a molar aqueous solution of sodium hydroxide, with water and brine, dried over magnesium sulfate, filtered and concentrated under reduced pressure. The crude product was purified by column chromatography on silica gel (gradient from heptane 100 to heptane 80/ethyl acetate 20) to give 0.42 g of 2-difluoromethoxy-4,5-difluoro-benzonitrile as a yellowish liquid.

C8H3F4NO (205.11), MS (EI): 205 (M⁺).

Building Block Synthesis According to Process M:

4-Fluoro-2-(2,2,2-trifluoro-ethoxy)-benzonitrile

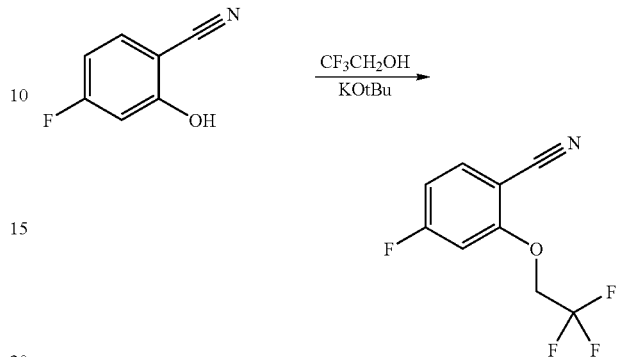

To a solution of 359 mg of trifluoroethanol in 3 mL of anhydrous tetrahydrofuran at 5° C. was slowly added 3.6 mL of a molar solution of potassium tert-butoxide in tert-butanol. The resulting solution was stirred for 30 minutes at 5° C. and slowly added to a solution of 500 mg of 2,4-difluoro-benzonitrile in 3 mL of anhydrous tetrahydrofuran at 5° C. The resulting mixture was stirred for 1 h at 5° C., then poured into water and extracted with ethyl acetate. The organic extracts were dried over magnesium sulfate, filtered and concentrated under reduced pressure. The crude product was purified by column chromatography on silica gel (gradient from heptane 100 to heptane 90/ethyl acetate 10) to give 640 mg of 4-fluoro-2-(2,2,2-trifluoro-ethoxy)-benzonitrile as a white solid.

C9H5F4NO (219.14), MS (ESI): 220 (M+H⁺).

The following examples were prepared according to process A:

EXAMPLE 1

3-(2-Chloro-4-{1-[4-methyl-2-(4-trifluoromethyl-phenyl)-thiazol-5-yl]-ethoxy}-phenyl)-4H-[1,2,4]oxadiazol-5-one

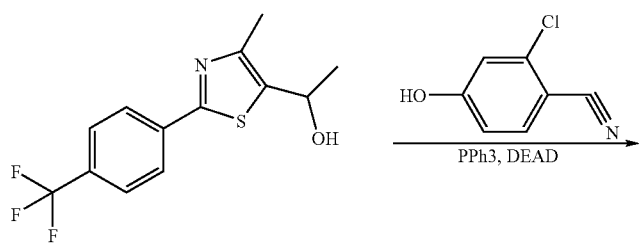

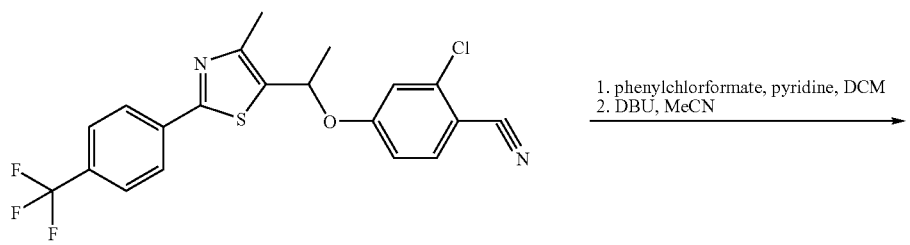

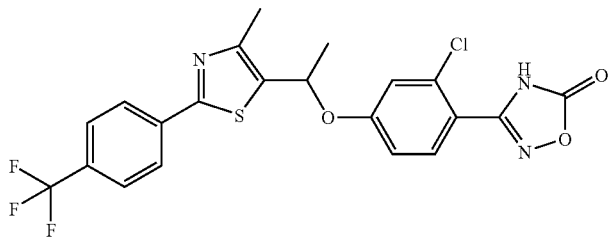

2-Chloro-4-{1-[4-methyl-2-(4-trifluoromethyl-phenyl)-thiazol-5-yl]-ethoxy}-benzonitrile

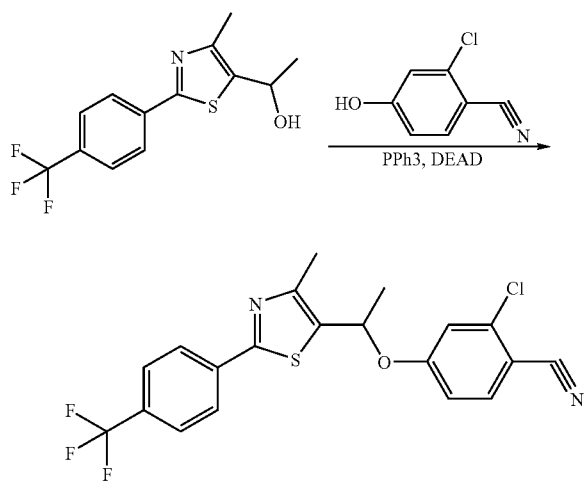

2.0 g 1-[4-Methyl-2-(4-trifluoromethyl-phenyl)-thiazol-5-yl]-ethanol and 1.18 g 2-chloro-4-hydroxybenzonitrile were dissolved in 50 ml tetrahydrofuran. At −20° C. 2.74 g triphenylphosphine and 1.82 g diethylazodicarboxylate were added. The cooling bath was removed and the reaction mixture stirred at room temperature for four hours. Then the reaction mixture was poured on 100 ml ice cold saturated NH4Cl solution and extracted five times with portions of 80 ml ethyl acetate. The combined organic layers were washed with 100 ml brine then dried over MgSO4. The solvent was evaporated in vacuo and the resulting residue purified by chromatography on silica gel with the eluent n-heptane: ethyl acetate=4:1 to obtain 2.1 g 2-chloro-4-{1-[4-methyl-2-(4-trifluoromethyl-phenyl)-thiazol-5-yl]-ethoxy}-benzonitrile as pale yellow solid.

C20H14ClF3N2OS (422.86), MS (ESI): 422.9 (M+H+).

3-(2-Chloro-4-{1-[4-methyl-2-(4-trifluoromethyl-phenyl)-thiazol-5-yl]-ethoxy}-phenyl)-4H-[1,2,4]oxadiazol-5-one

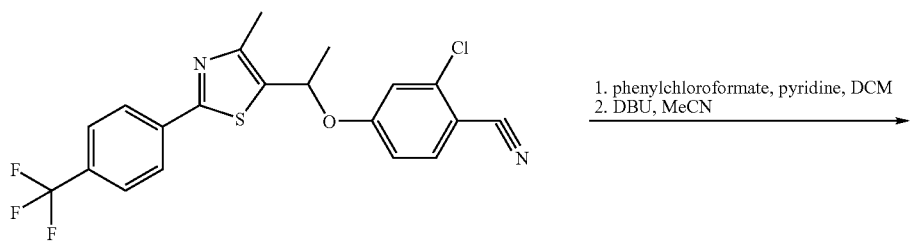

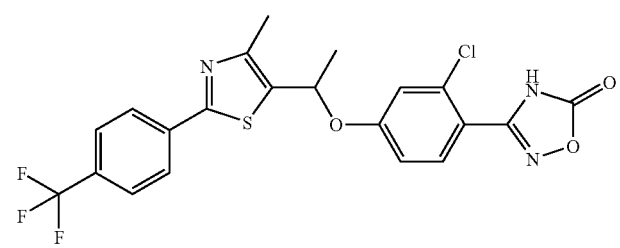

2.1 g 2-Chloro-4-{1-[4-methyl-2-(4-trifluoromethyl-phenyl)-thiazol-5-yl]-ethoxy}-benzonitrile were dissolved in a mixture of 20 ml tetrahydrofuran and 20 ml methanol. 3.29 g hydroxylamine hydrochloride were added followed by the addition of 5.74 ml triethylamine. The reaction mixture was stirred at 60° C. overnight. The solvents were removed in vacuo and the resulting residue poured into water and extracted five times with ethyl acetate. The combined organic extracts were washed with brine, dried over MgSO4 and the solvent was evaporated in vacuo. The residue was dissolved in 10 ml dichloromethane. 0.50 ml pyridine and 0.77 ml phenylchloroformate were added and the mixture stirred at room temperature for fifteen minutes. The mixture was diluted by the addition of 25 ml acetonitrile and 3.54 ml 1,8-diazabicyclo[5.4.0]undec-7-ene were added. The mixture was stirred at room temperature for thirty minutes. The mixture was evaporated in vacuo and the resulting crude material was purified by RP-HPLC to obtain 0.50 g 3-(2-chloro-4-{1-[4-methyl-2-(4-trifluoromethyl-phenyl)-thiazol-5-yl]-ethoxy}-phenyl)-4H-[1,2,4]oxadiazol-5-one.

The racemate was separated into its enantiomers by chromatography on chiral phase (Chiralpak AD-H/40) with the eluent n-heptane: propanol=5+1, Rt=5.4 min and 7.4 min.
C21H15ClF3N3O3S (481.88), MS (ESI): 482.1

EXAMPLE 2

3-(2-Chloro-4-{2-methyl-1-[4-methyl-2-(4-trifluoromethyl-phenyl)-thiazol-5-yl]-propoxa}-phenyl)-4H-[1,2,4]oxadiazol-5-one

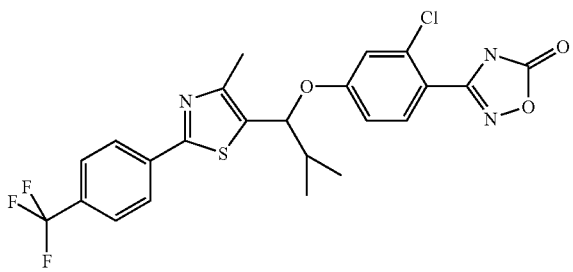

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-chloro-4-{2-methyl-1-[4-methyl-2-(4-trifluoromethyl-phenyl)-thiazol-5-yl]-propoxy}-phenyl)-4H-[1,2,4]oxadiazol-5-one was obtained from 2-Methyl-1-[4-methyl-2-(4-trifluoromethyl-phenyl)-thiazol-5-yl]-propan-1-ol and 2-chloro-4-hydroxybenzonitrile.

The racemate was separated into its enantiomers by chromatography on chiral phase (Chiralpak AD-H/40) with the eluent n-heptane: propanol=5+1, Rt=6.3 min and 11.3 min.
C23H19ClF3N3O3S (509.94), MS (ESI): 510.1 (M+H+).

EXAMPLE 3

3-(2-Chloro-4-{3-methyl-1-[4-methyl-2-(4-trifluoromethyl-phenyl)-thiazol-5-yl]-butoxy}-phenyl)-4H-[1,2,4]oxadiazol-5-one

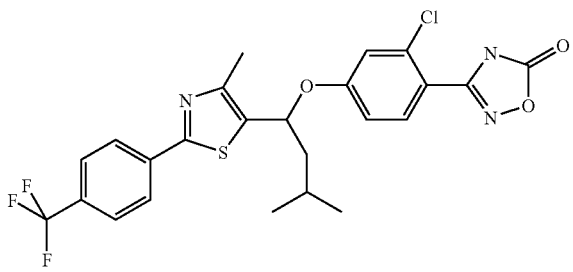

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-chloro-4-{3-methyl-1-[4-methyl-2-(4-trifluoromethyl-phenyl)-thiazol-5-yl]-butoxy}-phenyl)-4H-[1,2,4]oxadiazol-5-one was obtained from 3-Methyl-1-[4-methyl-2-(4-trifluoromethyl-phenyl)-thiazol-5-yl]-butan-1-ol and 2-chloro-4-hydroxybenzonitrile.

The racemate was separated into its enantiomers by chromatography on chiral phase (Chiralpak AD-H/40) with the eluent n-heptane: propanol=5+2, Rt=3.5 min and 5.4 min.
C24H21ClF3N3O3S (523.97), MS (ESI): 524.2 (M+H+).

EXAMPLE 4

3-(2-Chloro-4-{1-[4-methyl-2-(4-trifluoromethyl-phenyl)-thiazol-5-yl]-propoxy}-phenyl)-4H-[1,2,4]oxadiazol-5-one

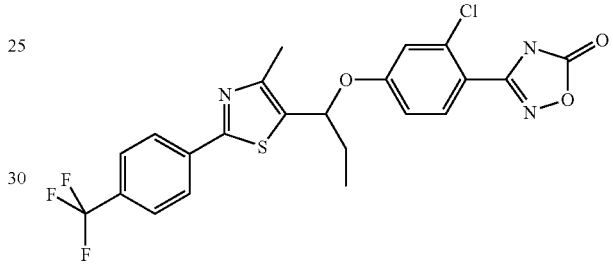

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-chloro-4-{1-[4-methyl-2-(4-trifluoromethyl-phenyl)-thiazol-5-yl]-propoxy}-phenyl)-4H-[1,2,4]oxadiazol-5-one was obtained from 1-[4-Methyl-2-(4-trifluoromethyl-phenyl)-thiazol-5-yl]-propan-1-ol and 2-chloro-4-hydroxybenzonitrile.

The racemate was separated into its enantiomers by chromatography on chiral phase (Chiralpak AD-H/40) with the eluent n-heptane: propanol=5+2, Rt=6.0 min and 9.7 min.
C22H17ClF3N3O3S (495.91), MS (ESI): 496.1 (M+H+).

EXAMPLE 5

3-(2-Chloro-4-{1-[4-methyl-2-(4-trifluoromethyl-phenyl)-thiazol-5-yl]-2-phenyl-ethoxy}-phenyl)-4H-[1,2,4]oxadiazol-5-one

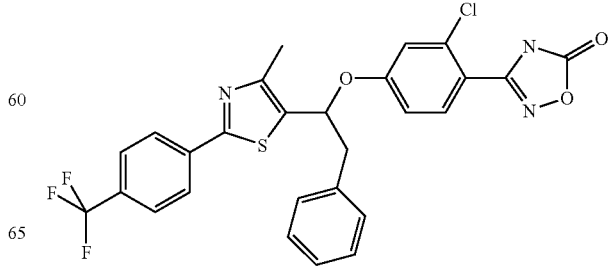

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-chloro-4-{1-[4-methyl-2-(4-trifluoromethyl-phenyl)-thiazol-5-yl]-2-phenyl-ethoxy}-phenyl)-4H-[1,2,4]oxadiazol-5-one was obtained from 1-[4-Methyl-2-(4-trifluoromethyl-phenyl)-thiazol-5-yl]-2-phenyl-ethanol and 2-chloro-4-hydroxybenzonitrile.

The racemate was separated into its enantiomers by chromatography on chiral phase (Chiralpak AD-H/40) with the eluent ethanol:methanol=1+1+0.1% trifluoroacetic acid, Rt=4.5 min and 7.3 min.

$C_{27}H_{19}ClF_3N_3O_3S$ (557.98), MS (ESI): 558.1 (M+H$^+$).

EXAMPLE 6

3-(2-Chloro-4-{[4-methyl-2-(4-trifluoromethyl-phenyl)-thiazol-5-yl]-phenyl-methoxy}-Phenyl)-4H-[1,2,4]oxadiazol-5-one

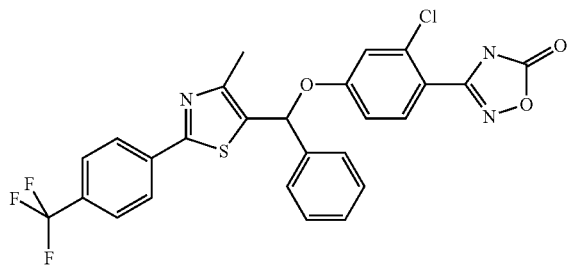

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-chloro-4-{[4-methyl-2-(4-trifluoromethyl-phenyl)-thiazol-5-yl]-phenyl-methoxy}-phenyl)-4H-[1,2,4]oxadiazol-5-one was obtained from [4-Methyl-2-(4-trifluoromethyl-phenyl)-thiazol-5-yl]-phenyl-methanol and 2-chloro-4-hydroxybenzonitrile. The racemate can be separated into its enantiomers by the method described herein before.

$C_{26}H_{17}ClF_3N_3O_3S$ (543.96), MS (ESI): 544.1 (M+H$^+$).

EXAMPLE 7

3-(2-Chloro-4-{1-[4-methyl-2-(4-trifluoromethyl-phenyl)-thiazol-5-yl]-3-phenyl-propoxy}-phenyl)-4H-[1,2,4]oxadiazol-5-one

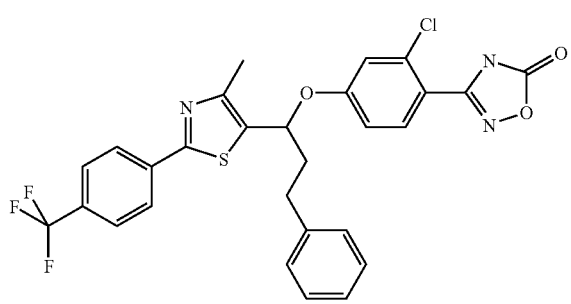

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Chloro-4-{1-[4-methyl-2-(4-trifluoromethyl-phenyl)-thiazol-5-yl]-3-phenyl-propoxy}-phenyl)-4H-[1,2,4]oxadiazol-5-one was obtained from 1-[4-Methyl-2-(4-trifluoromethyl-phenyl)-thiazol-5-yl]-3-phenyl-propan-1-ol and 2-chloro-4-hydroxybenzonitrile. The racemate can be separated into its enantiomers by the method described herein before.

$C_{28}H_{21}ClF_3N_3O_3S$ (572.01), MS (ESI): 572.4 (M+H$^+$).

EXAMPLE 8

3-(2-Chloro-4-{1-[4-methyl-2-(4-trifluoromethyl-phenyl)-oxazol-5-yl]-3-phenyl-propoxy}-phenyl)-4H-[1,2,4]oxadiazol-5-one

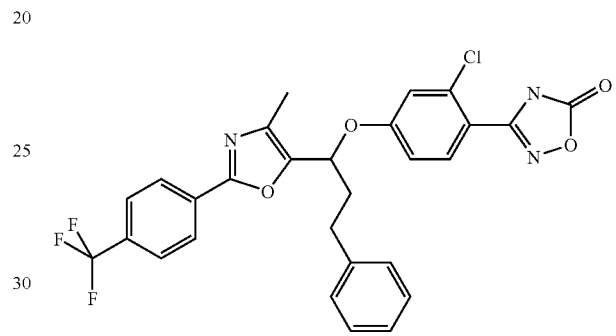

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Chloro-4-{1-[4-methyl-2-(4-trifluoromethyl-phenyl)-oxazol-5-yl]-3-phenyl-propoxy}-phenyl)-4H-[1,2,4]oxadiazol-5-one was obtained from 1-[4-Methyl-2-(4-trifluoromethyl-phenyl)-oxazol-5-yl]-3-phenyl-propan-1-ol and 2-chloro-4-hydroxybenzonitrile. The racemate can be separated into its enantiomers by the method described herein before.

$C_{28}H_{21}ClF_3N_3O_4$ (555.95), MS (ESI): 556.2 (M+H$^+$).

EXAMPLE 9

3-(2-Chloro-4-[2-(4-fluoro-phenyl)-1-[4-methyl-2-(4-trifluoromethyl-phenyl)-thiazol-5-yl]-ethoxy]-phenyl)-4H-[1,24]oxadiazol-5-one

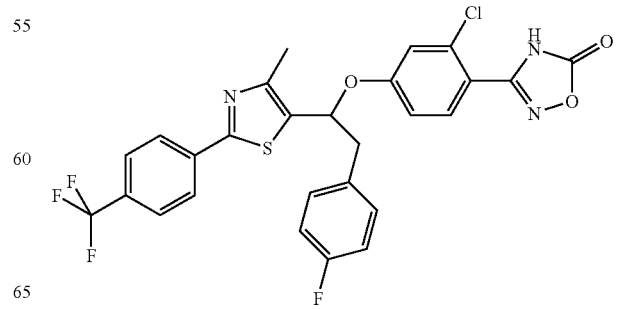

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Chloro-4-{2-(4-fluoro-phenyl)-1-[4-methyl-2-(4-trifluoromethyl-phenyl)-thiazol-5-yl]-ethoxy}-phenyl)-4H-[1,2,4]oxadiazol-5-one was obtained from 2-(4-Fluoro-phenyl)-1-[4-methyl-2-(4-trifluoromethyl-phenyl)-thiazol-5-yl]-ethanol and 2-chloro-4-hydroxybenzonitrile. The racemate was separated into its enantiomers by chromatography on chiral phase (Chiralpak AD-H/39) with the eluent n-heptane:iso-propanol=2:1, Rt=5.75 min and 14.84 min.

C27H18ClF4N3O3S (575.97), MS (ESI): 576.2 (M+H$^+$).

EXAMPLE 10

3-(2-Chloro-4-{1-[4-methyl-2-(4-trifluoromethyl-phenyl)-thiazol-5-yl]-2-pyridin-2-yl-ethoxy}-phenyl)-4H-[1,2,4]oxadiazol-5-one

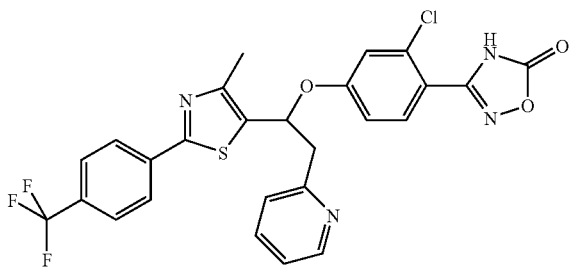

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Chloro-4-{1-[4-methyl-2-(4-trifluoromethyl-phenyl)-thiazol-5-yl]-2-pyridin-2-yl-ethoxy}-phenyl)-4H-[1,2,4]oxadiazol-5-one was obtained from 1-[4-Methyl-2-(4-trifluoromethyl-phenyl)-thiazol-5-yl]-2-pyridin-2-yl-ethanol and 2-chloro-4-hydroxybenzonitrile.

The racemate was separated into its enantiomers by chromatography on chiral phase (Chiralpak AD-H/40) with the eluent n-heptane:iso-propanol=2:1, Rt=6.87 min and 12.04 min.

C26H18ClF3N4O3S (558.97), MS (ESI): 559.2 (M+H$^+$), Rf (ethyl acetate)=0.18.

The following examples were prepared according to process B:

EXAMPLE 11

3-(2-Bromo-4-{1-[4-methyl-2-(4-trifluoromethyl-phenyl)-thiazol-5-yl]-propoxy}-phenyl)-4H-[1,2,4]oxadiazol-5-one

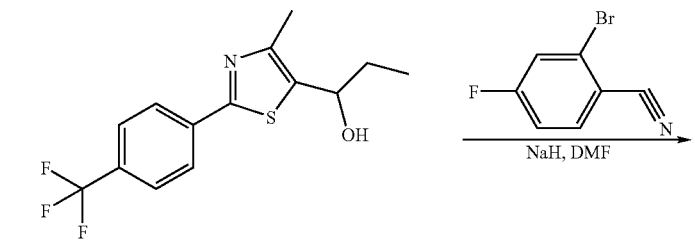

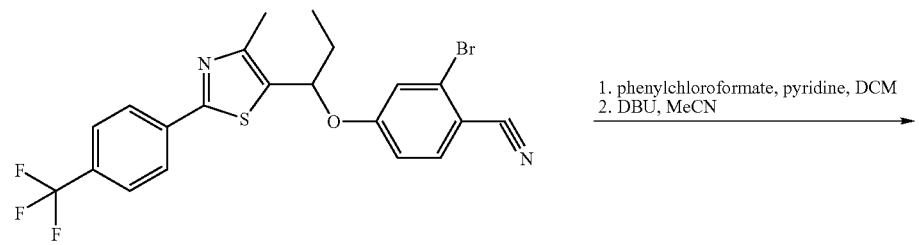

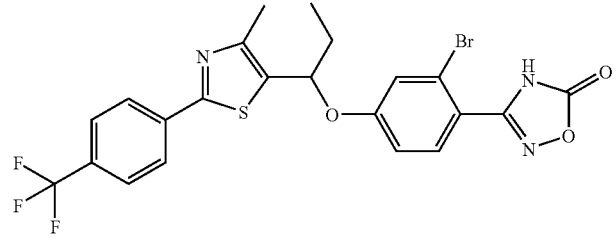

2-Bromo-4-{1-[4-methyl-2-(4-trifluoromethyl-phenyl)-thiazol-5-yl]-propoxy}-benzonitrile

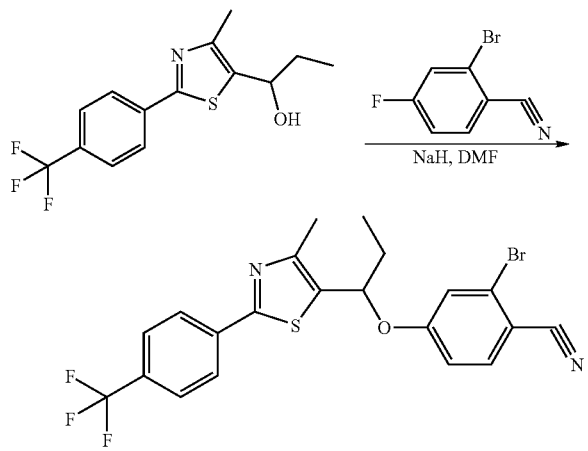

500 mg 1-[4-Methyl-2-(4-trifluoromethyl-phenyl)-thiazol-5-yl]-propan-1-ol were dissolved in 5 ml dimethylformamide. 108 mg sodium hydride were added and the mixture stirred at room temperature. After thirty minutes commercially available 2-bromo-4-fluorobenzonitrile were added and the reaction mixture stirred at room temperature for one hour. Then 5 ml water were added and the mixture extracted three times with portions of 30 ml ethyl acetate. The combined organic layers were dried over MgSO4 and the solvent removed in vacuo. The residue was purified by reversed phase HPLC to obtain 375 mg 2-Bromo-4-{1-[4-methyl-2-(4-trifluoromethyl-phenyl)-thiazol-5-yl]-propoxy}-benzonitrile as an oil.

C21H16BrF3N2OS (481.34), MS (ESI): 481.0 (M+H$^+$).

3-(2-Bromo-4-{1-[4-methyl-2-(4-trifluoromethyl-phenyl)-thiazol-5-yl]-propoxy}-phenyl)-4H-[1,2,4]oxadiazol-5-one

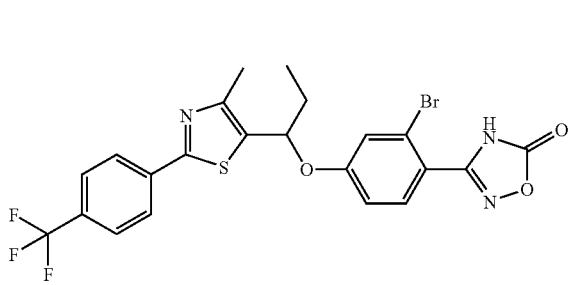

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Bromo-4-{1-[4-methyl-2-(4-trifluoromethyl-phenyl)-thiazol-5-yl]-propoxy}-phenyl)-4H-[1,2,4]oxadiazol-5-one was obtained from 2-Bromo-4-{1-[4-methyl-2-(4-trifluoromethyl-phenyl)-thiazol-5-yl]-propoxy}-benzonitrile.

The racemate can be separated into its enantiomers by the method described herein before.

C22H17BrF3N3O3S (540.36), MS (ESI): 540.0 (M+H$^+$).

EXAMPLE 12

3-[4-{1-[4-Methyl-2-(4-trifluoromethyl-phenyl)-thiazol-5-yl]-propoxy}-2-(2,2,2-trifluoro-ethoxymethyl)-phenyl]-4H-[1,2,4]oxadiazol-5-one

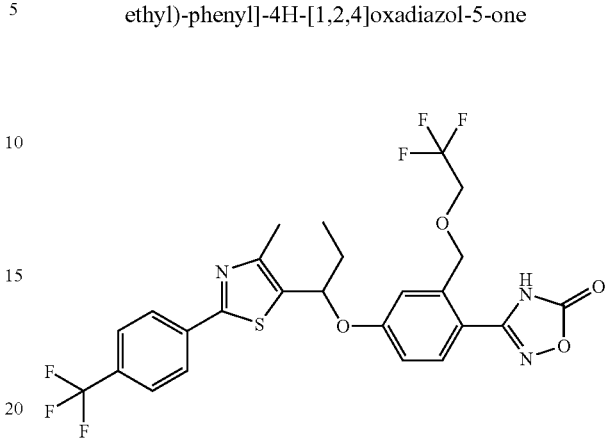

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-[4-{1-[4-Methyl-2-(4-trifluoromethyl-phenyl)-thiazol-5-yl]-propoxy}-2-(2,2,2-trifluoro-ethoxymethyl)-phenyl]-4H-[1,2,4]oxadiazol-5-one was obtained from 1-[4-Methyl-2-(4-trifluoromethyl-phenyl)-thiazol-5-yl]-propan-1-ol and 4-Fluoro-2-(2,2,2-trifluoro-ethoxymethyl)-benzonitrile.

The racemate can be separated into its enantiomers by the method described herein before.

C25H21F6N3O4S (573.52), MS (ESI): 574.1 (M+H$^+$).

EXAMPLE 13

3-(2-Methoxymethyl-4-{1-[4-methyl-2-(4-trifluoromethyl-phenyl)-thiazol-5-yl]-propoxy}-phenyl)-4H-[1,2,4]oxadiazol-5-one

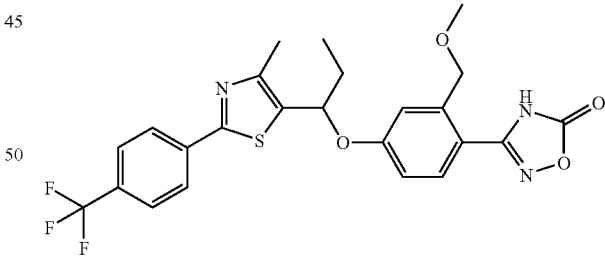

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Methoxymethyl-4-{1-[4-methyl-2-(4-trifluoromethyl-phenyl)-thiazol-5-yl]-propoxy}-phenyl)-4H-[1,2,4]oxadiazol-5-one was obtained from 1-[4-Methyl-2-(4-trifluoromethyl-phenyl)-thiazol-5-yl]-propan-1-ol and 4-Fluoro-2-methoxymethyl-benzonitrile.

The racemate can be separated into its enantiomers by the method described herein before.

C24H22F3N3O4S (505.52), MS (ESI): 506.1 (M+H$^+$).

EXAMPLE 14

3-(2-Ethoxymethyl-4-{1-[4-methyl-2-(4-trifluoromethyl-phenyl)-thiazol-5-yl]-propoxy}-Phenyl)-4H-[1,2,4]oxadiazol-5-one

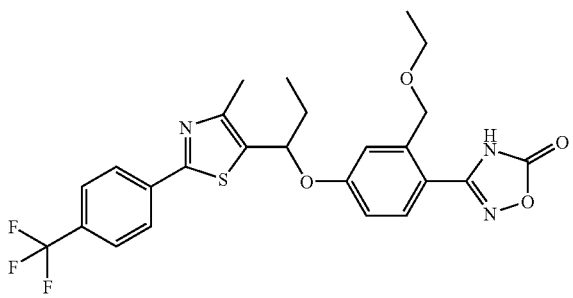

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Ethoxymethyl-4-{1-[4-methyl-2-(4-trifluoromethyl-phenyl)-thiazol-5-yl]-propoxy}-phenyl)-4H-[1,2,4]oxadiazol-5-one was obtained from 1-[4-Methyl-2-(4-trifluoromethyl-phenyl)-thiazol-5-yl]-propan-1-ol and 2-Ethoxymethyl-4-fluoro-benzonitrile.

The racemate can be separated into its enantiomers by the method described herein before.

$C_{25}H_{24}F_3N_3O_4S$ (519.55), MS (ESI): 520.1 (M+H$^+$).

EXAMPLE 15

3-(2-Ethyl-4-[1-[4-methyl-2-(4-trifluoromethyl-phenyl)-thiazol-5-yl]-propoxy]-phenyl)-4H-[1,2,4]oxadiazol-5-one

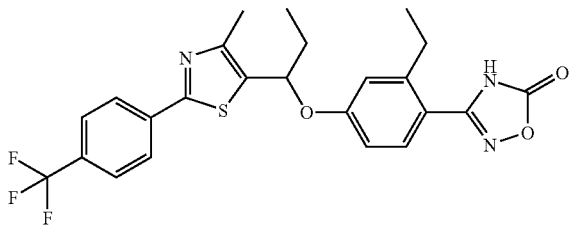

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Ethyl-4-{1-[4-methyl-2-(4-trifluoromethyl-phenyl)-thiazol-5-yl]-propoxy}-phenyl)-4H-[1,2,4]oxadiazol-5-one was obtained from 1-[4-Methyl-2-(4-trifluoromethyl-phenyl)-thiazol-5-yl]-propan-1-ol and 2-Ethyl-4-fluoro-benzonitrile.

The racemate can be separated into its enantiomers by the method described herein before.

$C_{24}H_{22}F_3N_3O_3S$ (489.52), MS (ESI): 490.1 (M+H$^+$).

EXAMPLE 16

3-(2-Cyclopropyl-4-{1-[4-methyl-2-(4-trifluoromethyl-Phenyl)-thiazol-5-yl]-propoxy}-phenyl)-4H-[1,2,4]oxadiazol-5-one

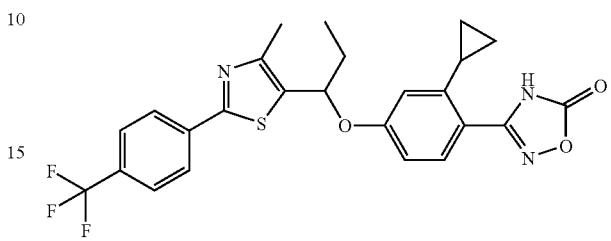

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Cyclopropyl-4-{1-[4-methyl-2-(4-trifluoromethyl-phenyl)-thiazol-5-yl]-propoxy}-phenyl)-4H-[1,2,4]oxadiazol-5-one was obtained from 1-[4-Methyl-2-(4-trifluoromethyl-phenyl)-thiazol-5-yl]-propan-1-ol and 2-Cyclopropyl-4-fluoro-benzonitrile.

The racemate can be separated into its enantiomers by the method described herein before.

$C_{25}H_{22}F_3N_3O_3S$ (501.53), MS (ESI): 502.1 (M+H$^+$).

EXAMPLE 17

3-(4-{1-[4-Methyl-2-(4-trifluoromethyl-phenyl)-thiazol-5-yl]-propoxy}-naphthalen-1-yl)-4H-[1,2,4]oxadiazol-5-one

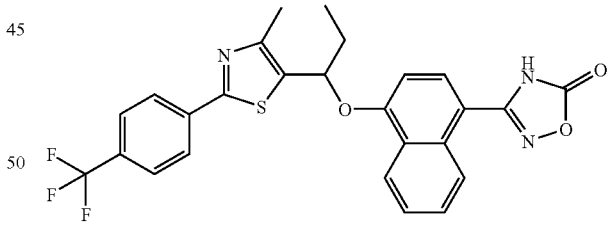

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(4-{1-[4-Methyl-2-(4-trifluoromethyl-phenyl)-thiazol-5-yl]-propoxy}-naphthalen-1-yl)-4H-[1,2,4]oxadiazol-5-one was obtained from 1-[4-Methyl-2-(4-trifluoromethyl-phenyl)-thiazol-5-yl]-propan-1-ol and commercially available 1-Cyano-4-fluoronaphthalene.

The racemate can be separated into its enantiomers by the method described herein before.

$C_{26}H_{20}F_3N_3O_3S$ (511.53), MS (ESI): 512.2 (M+H$^+$).

EXAMPLE 18

3-(4-{1-[4-Methyl-2-(4-trifluoromethyl-phenyl)-thiazol-5-yl]-propoxy}-2-trifluoromethyl-Phenyl)-4H-[1,2,4]oxadiazol-5-one

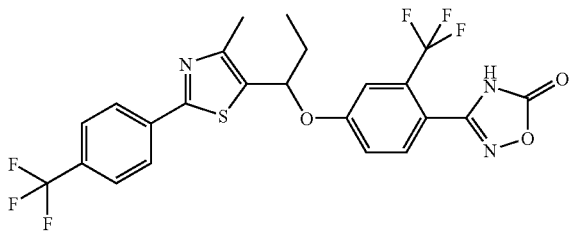

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(4-{1-[4-Methyl-2-(4-trifluoromethyl-phenyl)-thiazol-5-yl]-propoxy}-2-trifluoromethyl-phenyl)-4H-[1,2,4]oxadiazol-5-one was obtained from 1-[4-Methyl-2-(4-trifluoromethyl-phenyl)-thiazol-5-yl]-propan-1-ol and commercially available 4-fluoro-2-(trifluoromethyl)benzonitrile.

The racemate can be separated into its enantiomers by the method described herein before.

C23H17F6N3O3S (529.46), MS (ESI): 530.1 (M+H$^+$).

EXAMPLE 19

3-(4'-Fluoro-5-{1-[4-methyl-2-(4-trifluoromethyl-phenyl)-thiazol-5-yl]-propoxy}-biphenyl-2-yl)-4H-[1,2,4]oxadiazol-5-one

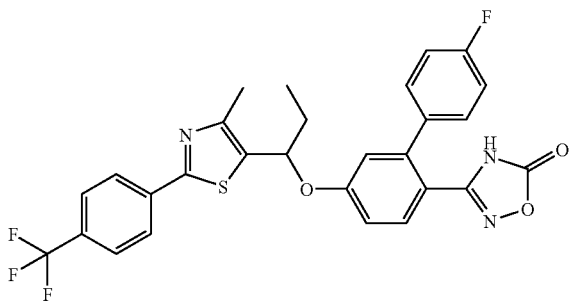

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(4'-Fluoro-5-{1-[4-methyl-2-(4-trifluoromethyl-phenyl)-thiazol-5-yl]-propoxy}-biphenyl-2-yl)-4H-[1,2,4]oxadiazol-5-one was obtained from 1-[4-Methyl-2-(4-trifluoromethyl-phenyl)-thiazol-5-yl]-propan-1-ol and 5,4'-Difluoro-biphenyl-2-carbonitrile.

The racemate can be separated into its enantiomers by the method described herein before.

C28H21F4N3O3S (555.56), MS (ESI): 556.1 (M+H$^+$).

EXAMPLE 20

3-(2-Chloro-4-{2,2,2-trifluoro-1-[4-methyl-2-(4-trifluoromethyl-phenyl)-thiazol-5-yl]-ethoxy}-phenyl)-4H-[1,2,4]oxadiazol-5-one

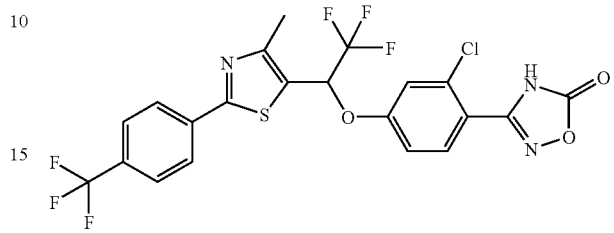

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Chloro-4-{2,2,2-trifluoro-1-[4-methyl-2-(4-trifluoromethyl-phenyl)-thiazol-5-yl]-ethoxy}-phenyl)-4H-[1,2,4]oxadiazol-5-one was obtained from 2,2,2-Trifluoro-1-[4-methyl-2-(4-trifluoromethyl-phenyl)-thiazol-5-yl]-ethanol and 2-Chloro-4-fluoro-benzonitrile.

The racemate can be separated into its enantiomers by the method described herein before.

C21H12ClF6N3O3S (535.86), MS (ESI): 536.1 (M+H$^+$).

EXAMPLE 21

3-(2-Chloro-4-{2,2-difluoro-1-[4-methyl-2-(4-trifluoromethyl-phenyl)-thiazol-5-yl]-butoxy}-phenyl)-4H-[1,2,4]oxadiazol-5-one

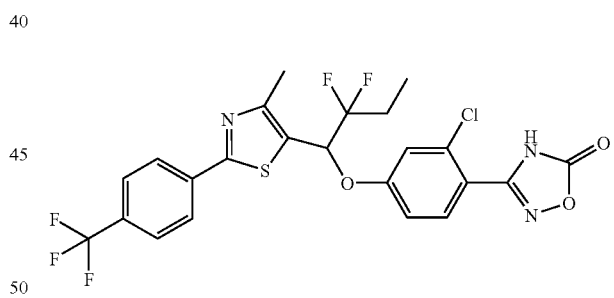

According to the method described for 3-(2-Bromo-4-{1-[4-methyl-2-(4-trifluoromethyl-phenyl)-thiazol-5-yl]-propoxy}-phenyl)-4H-[1,2,4]oxadiazol-5-one, 3-(2-Chloro-4-{2,2-difluoro-1-[4-methyl-2-(4-trifluoromethyl-phenyl)-thiazol-5-yl]-butoxy}-phenyl)-4H-[1,2,4]oxadiazol-5-one was obtained from 2,2-Difluoro-1-[4-methyl-2-(4-trifluoromethyl-phenyl)-thiazol-5-yl]-butan-1-ol and 2-Chloro-4-fluoro-benzonitrile.

The racemate can be separated into its enantiomers by the method described herein before.

C23H17ClF5N3O3S (545.92), MS (ESI): 546.1 (M+H$^+$).

The following examples were prepared according to process C:

EXAMPLE 22

3-(2-Fluoro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one

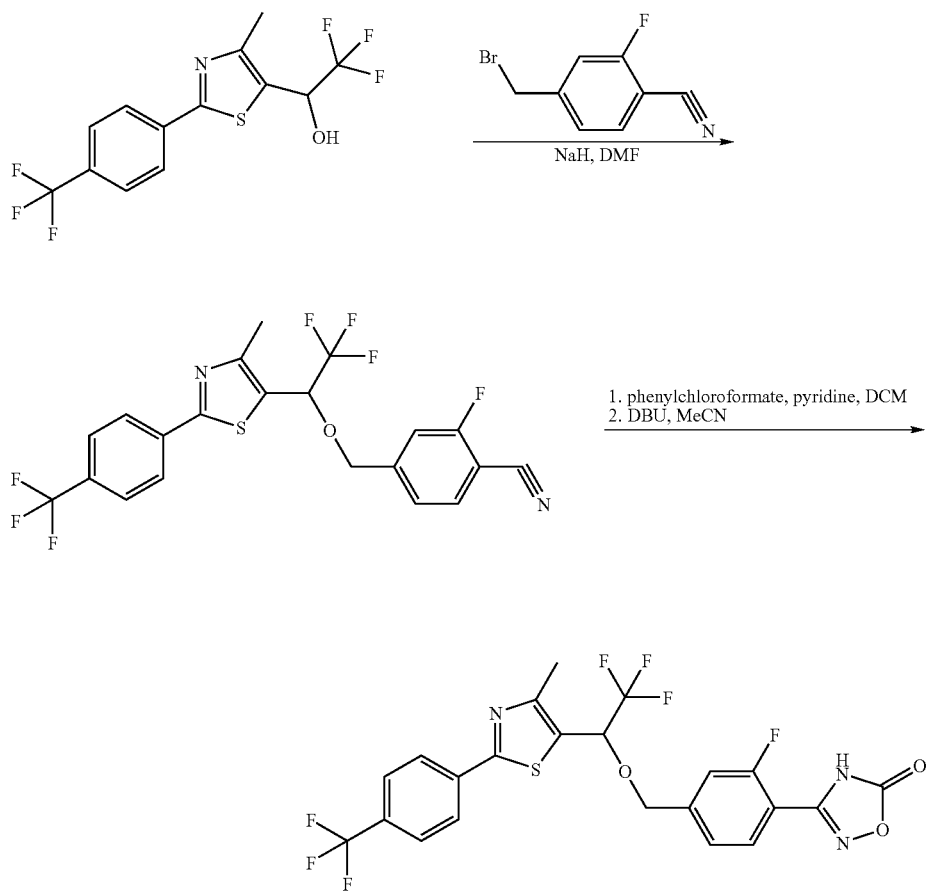

2-Fluoro-4-[2,2,2-trifluoro-1-[4-methyl-2-(4-trifluoromethyl-phenyl)-thiazol-5-yl]-ethoxymethyl]-benzonitrile

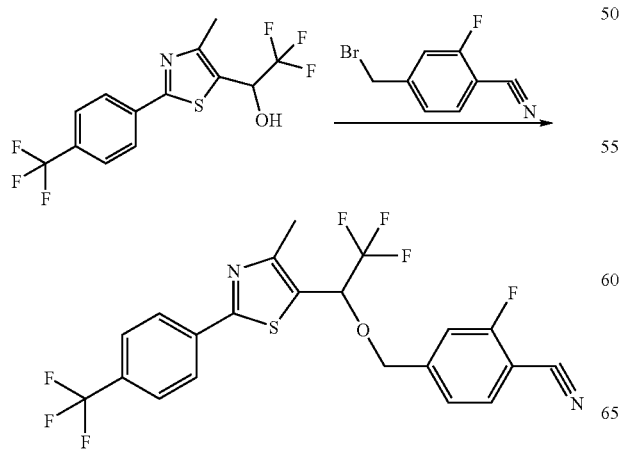

1.30 g 2,2,2-Trifluoro-1-[4-methyl-2-(4-trifluoromethyl-phenyl)-thiazol-5-yl]-ethanol and 815 mg 4-Bromomethyl-2-fluoro-benzonitrile were dissolved in 40 ml dimethylformamide. 192 mg sodium hydride were added and the mixture stirred at room temperature for one hour. Then 15 ml water were added and the mixture extracted three times with portions of 50 ml ethyl acetate. The combined organic layers were dried over MgSO4 and the solvent removed in vacuo. The residue was purified by reversed phase HPLC to obtain 840 mg 2-Fluoro-4-{2,2,2-trifluoro-1-[4-methyl-2-(4-trifluoromethyl-phenyl)-thiazol-5-yl]-ethoxymethyl}-benzonitrile as an oil.

C21H13F7N2OS (474.40), MS (ESI): 475.1 (M+H$^+$), Rf(n-heptane:ethyl acetate=1:1)=0.57.

3-(2-Fluoro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one

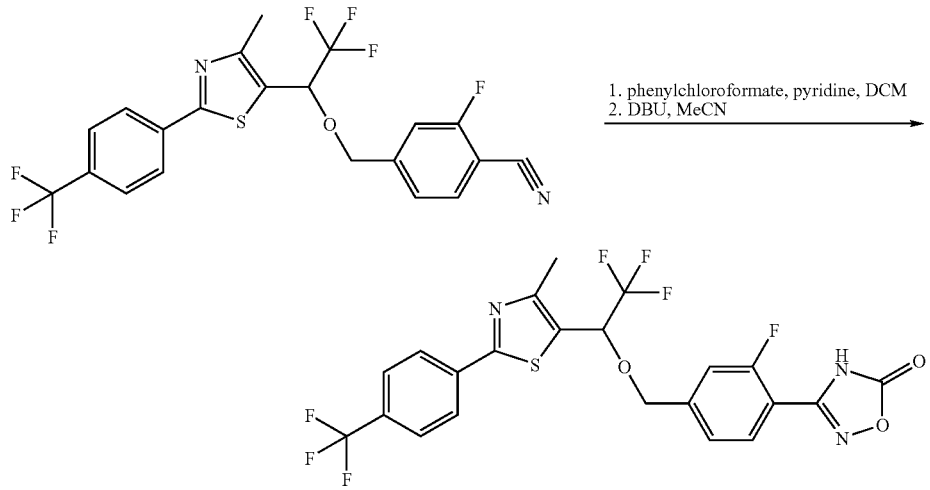

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-Fluoro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one was obtained from 2-Fluoro-4-{2,2,2-trifluoro-1-[4-methyl-2-(4-trifluoromethyl-phenyl)-thiazol-5-yl]-ethoxymethyl}-benzonitrile. The racemate was separated into its enantiomers by chromatography on chiral phase (Chiralpak AD-H/39) with the eluent n-heptane: iso-propanol:ethanol=8:1:1, Rt=8.13 min and 11.09 min.

C22H14F7N3O3S (533.43), MS (ESI): 534.1 (M+H$^+$), Rf(n-heptane:ethyl acetate=1:1)=0.14.

EXAMPLE 23

3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one

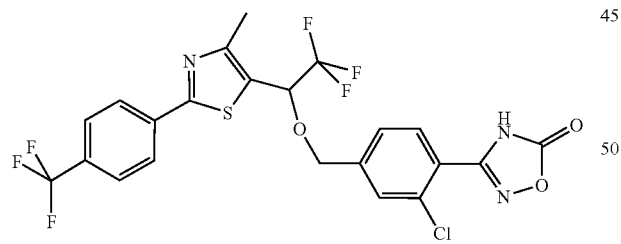

According to the method described for 3-(2-Fluoro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one was obtained from 2,2,2-Trifluoro-1-[4-methyl-2-(4-trifluoromethyl-phenyl)-thiazol-5-yl]-ethanol and 4-Bromomethyl-2-chloro-benzonitrile.

The racemate can be separated into its enantiomers by the method described herein before.

C22H14ClF6N3O3S (549.88), MS (ESI): 550.0 (M+H$^+$).

EXAMPLE 24

3-(2-Cyclopropyl-4-{2,2,2-trifluoro-1-[4-methyl-2-(4-trifluoromethyl-Phenyl)-thiazol-5-yl]-ethoxymethyl}-phenyl)-4H-[1,2,4]oxadiazol-5-one

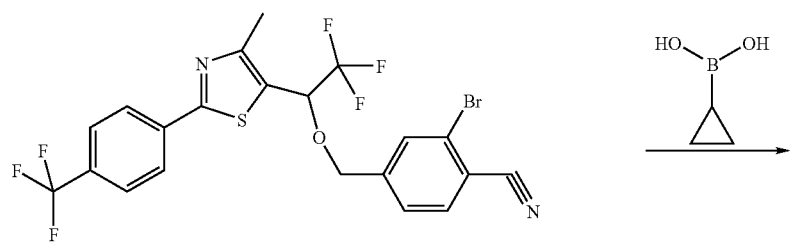

-continued

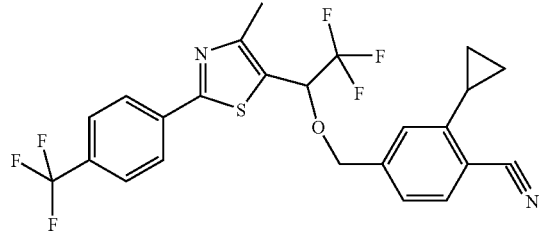

1. phenylchloroformate, pyridine, DCM
2. DBU, MeCN

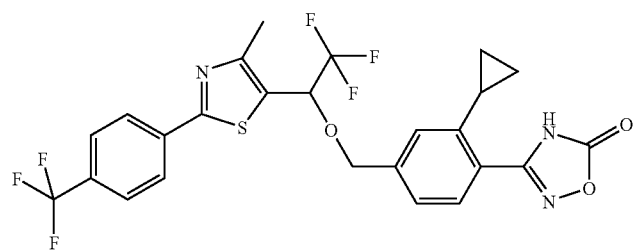

2-Bromo-4-{2,2,2-trifluoro-1-[4-methyl-2-(4-trifluoromethyl-phenyl)-thiazol-5-yl]-ethoxymethyl}-benzonitrile

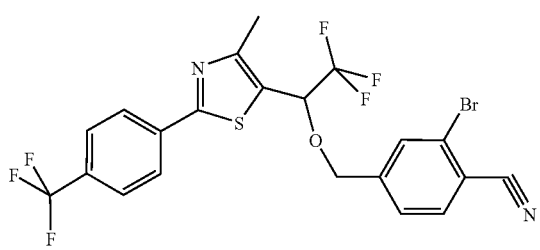

According to the method described for 2-Fluoro-4-{2,2,2-trifluoro-1-[4-methyl-2-(4-trifluoromethyl-phenyl)-thiazol-5-yl]-ethoxymethyl}-benzonitrile, 2-Bromo-4-{2,2,2-trifluoro-1-[4-methyl-2-(4-trifluoromethyl-phenyl)-thiazol-5-yl]-ethoxymethyl}-benzonitrile was obtained from 2,2,2-Trifluoro-1-[4-methyl-2-(4-trifluoromethyl-phenyl)-thiazol-5-yl]-ethanol and 2-Bromo-4-bromomethyl-benzonitrile.

C21H13BrF6N2OS (535.3), MS (ESI): 335.0 (M+H+), Rf(n-heptane:ethyl acetate=4:1)=0.10.

2-Cyclopropyl-4-{2,2,2-trifluoro-1-[4-methyl-2-(4-trifluoromethyl-phenyl)-thiazol-5-yl]-ethoxymethyl}-benzonitrile

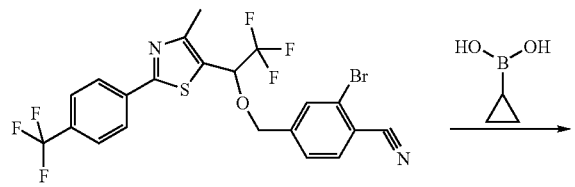 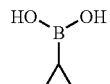

-continued

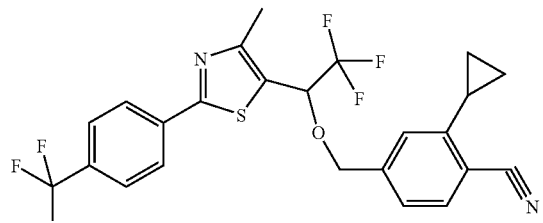

147 mg 2-Bromo-4-{2,2,2-trifluoro-1-[4-methyl-2-(4-trifluoromethyl-phenyl)-thiazol-5-yl]-ethoxymethyl}-benzonitrile, 15 mg Tricyclohexylphosphine, 71 mg Cyclopropylboronic acid and 224 mg Tripotassiumphosphate monohydrate were dissolved in a mixture of 2 ml toluene and 0.2 ml water. The reaction mixture was degassed and 62 mg palladium(II) acetate were added and the reaction mixture heated under microwave irradiation at 10° C. for 2.5 hours. The cooled reaction mixture was diluted by addition of 50 ml ethyl acetate and filtered. The filtrate was evaporated and the residue purified by reverse phase HPLC to obtain 97 mg 2-Cyclopropyl-4-{2,2,2-trifluoro-1-[4-methyl-2-(4-trifluoromethyl-phenyl)-thiazol-5-yl]-ethoxymethyl}-benzonitrile as an oil.

C24H18F6N2OS (496.48), MS (ESI): 497.2 (M+H+), Rf(n-heptane:ethyl acetate=4:1)=0.16.

3-(2-Cyclopropyl-4-{2,2,2-trifluoro-1-[4-methyl-2-(4-trifluoromethyl-Phenyl)-thiazol-5-yl]-ethoxymethyl}-phenyl)-4H-[1,2,4]oxadiazol-5-one

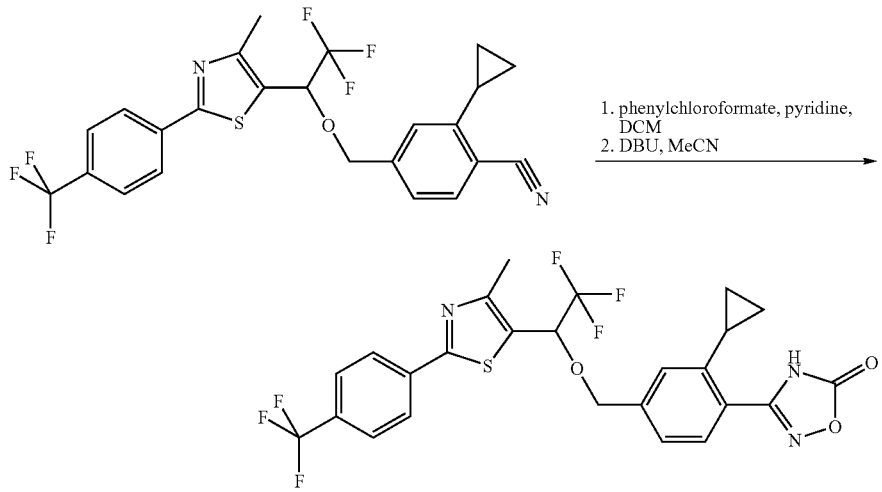

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(2-Cyclopropyl-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one was obtained from 2-Cyclopropyl-4-{2,2,2-trifluoro-1-[4-methyl-2-(4-trifluoromethyl-phenyl)-thiazol-5-yl]-ethoxymethyl}-benzonitrile.

The racemate can be separated into its enantiomers by the method described herein before.

C25H19F6N3O3S (555.50), MS (ESI): 556.1 (M+H+).

EXAMPLE 25

3-(8-{2,2,2-Trifluoro-1-[4-methyl-2-(4-trifluoromethyl-phenyl)-thiazol-5-yl]-ethoxymethyl}-quinolin-5-yl)-4H-[1,2,4]oxadiazol-5-one

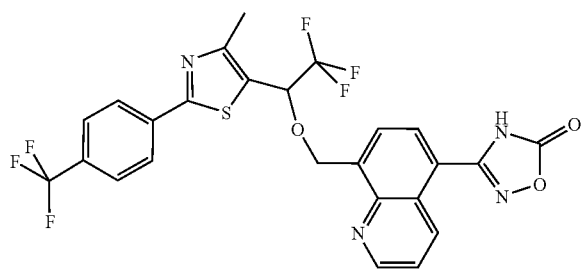

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(8-{2,2,2-Trifluoro-1-[4-methyl-2-(4-trifluoromethyl-phenyl)-thiazol-5-yl]-ethoxymethyl}-quinolin-5-yl)-4H-[1,2,4]oxadiazol-5-one was obtained from 2,2,2-Trifluoro-1-[4-methyl-2-(4-trifluoromethyl-phenyl)-thiazol-5-yl]-ethanol and 8-Bromomethyl-quinoline-5-carbonitrile.

The racemate can be separated into its enantiomers by the method described herein before.

C25H16F6N4O3S (566.49), MS (ESI): 567.1 (M+H+).

EXAMPLE 26

3-(4-{2,2,2-Trifluoro-1-[4-methyl-2-(4-trifluoromethyl-phenyl)-thiazol-5-yl]-ethoxymethyl}-naphthalen-1-yl)-4H-[1,2,4]oxadiazol-5-one

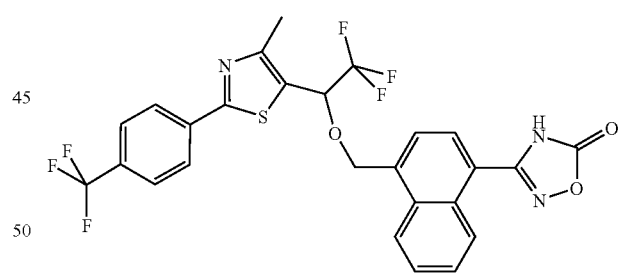

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{2,2,2-Trifluoro-1-[4-methyl-2-(4-trifluoromethyl-phenyl)-thiazol-5-yl]-ethoxymethyl}-naphthalen-1-yl)-4H-[1,2,4]oxadiazol-5-one was obtained from 2,2,2-Trifluoro-1-[4-methyl-2-(4-trifluoromethyl-phenyl)-thiazol-5-yl]-ethanol and 5-Bromomethyl-naphthalene-1-carbonitrile.

The racemate can be separated into its enantiomers by the method described herein before.

C26H17F6N3O3S (565.50), MS (ESI): 566.0 (M+H+).

EXAMPLE 27

3-(2-Chloro-6-{2,2,2-trifluoro-1-[4-methyl-2-(4-trifluoromethyl-phenyl)-thiazol-5-yl]-ethoxymethyl}-pyridin-3-yl)-4H-[1,2,4]oxadiazol-5-one

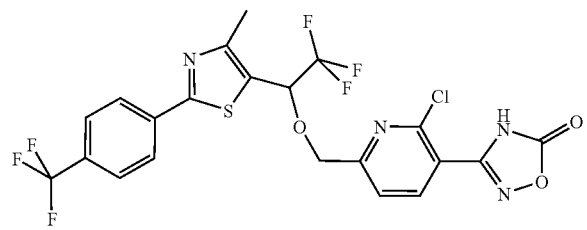

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(2-Chloro-6-{2,2,2-trifluoro-1-[4-methyl-2-(4-trifluoromethyl-phenyl)-thiazol-5-yl]-ethoxymethyl}-pyridin-3-yl)-4H-[1,2,4]oxadiazol-5-one was obtained from 2,2,2-Trifluoro-1-[4-methyl-2-(4-trifluoromethyl-phenyl)-thiazol-5-yl]-ethanol and 6-Bromomethyl-2-chloro-nicotinonitrile.

The racemate can be separated into its enantiomers by the method described herein before.

C21H13ClF6N4O3S (550.87), MS (ESI): 551.3 (M+H$^+$).

EXAMPLE 28

3-(2-Fluoro-4-{1-[4-methyl-2-(4-trifluoromethyl)-phenyl)-thiazol-5-vil-propoxymethyl]-phenyl)-4H-[1,2,4]oxadiazol-5-one

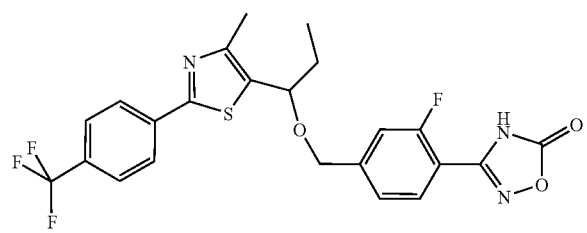

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(2-Fluoro-4-{1-[4-methyl-2-(4-trifluoromethyl-phenyl)-thiazol-5-yl]-propoxymethyl}-phenyl)-4H-[1,2,4]oxadiazol-5-one was obtained from 1-[4-Methyl-2-(4-trifluoromethyl-phenyl)-thiazol-5-yl]-propan-1-ol and 4-Bromomethyl-2-fluoro-benzonitrile.

The racemate can be separated into its enantiomers by the method described herein before.

C23H19F4N3O3S (493.48), MS (ESI): 494.2 (M+H$^+$).

EXAMPLE 29

3-(4-{1-[4-Methyl-2-(4-trifluoromethyl-phenyl)-thiazol-5-yl]-propoxymethyl}-naphthalen-1-yl)-4H-[1,2,4]oxadiazol-5-one

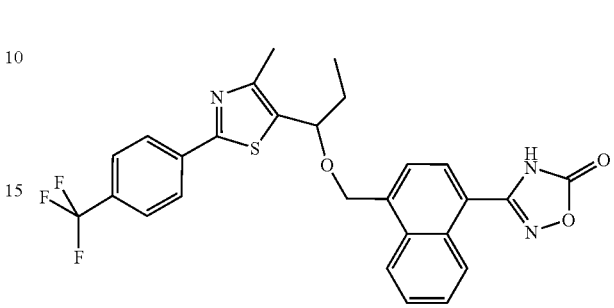

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{1-[4-Methyl-2-(4-trifluoromethyl-phenyl)-thiazol-5-yl]-propoxymethyl}-naphthalen-1-yl)-4H-[1,2,4] oxadiazol-5-one was obtained from 1-[4-Methyl-2-(4-trifluoromethyl-phenyl)-thiazol-5-yl]-propan-1-ol and 5-Bromomethyl-naphthalene-1-carbonitrile.

The racemate can be separated into its enantiomers by the method described herein before.

C27H22F3N3O3S (525.55), MS (ESI): 526.1 (M+H$^+$).

EXAMPLE 30

3-(4-{1-[4-Methyl-2-(4-trifluoromethyl-phenyl)-thiazol-5-yl]-propoxymethyl}-phenyl)-4H-[1,2,4]oxadiazol-5-one

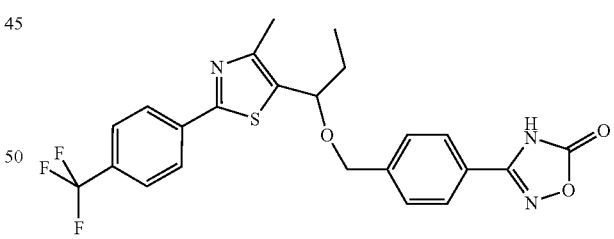

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{1-[4-Methyl-2-(4-trifluoromethyl-phenyl)-thiazol-5-yl]-propoxymethyl}-phenyl)-4H-[1,2,4]oxadiazol-5-one was obtained from 1-[4-Methyl-2-(4-trifluoromethyl-phenyl)-thiazol-5-yl]-propan-1-ol and commercially available 4-Bromomethyl-benzonitrile. The racemate can be separated into its enantiomers by the method described herein before.

C23H20F3N3O3S (475.49), MS (ESI): 476.1.1 (M+H$^+$).

EXAMPLE 31

3-(4-{2,2-Difluoro-1-[4-methyl-2-(4-trifluoromethyl-phenyl)-thiazol-5-yl]-butoxymethyl}-Phenyl)-4H-[1,2,4]oxadiazol-5-one

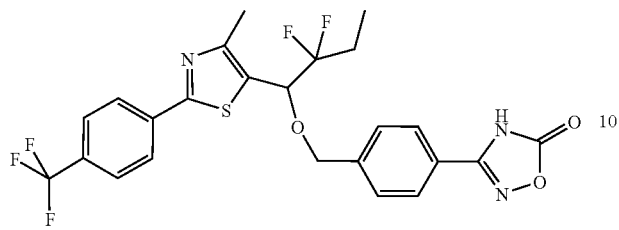

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{2,2-Difluoro-1-[4-methyl-2-(4-trifluoromethyl-phenyl)-thiazol-5-yl]-butoxymethyl}-phenyl)-4H-[1,2,4]oxadiazol-5-one was obtained from 2,2-Difluoro-1-[4-methyl-2-(4-trifluoromethyl-phenyl)-thiazol-5-yl]-butan-1-ol and commercially available 4-Bromomethyl-benzonitrile.

The racemate can be separated into its enantiomers by the method described herein before.

C24H20F5N3O3S (525.50), MS (ESI): 526.0 (M+H$^+$).

EXAMPLE 32

3-(4-{2-Cyclopropyl-2,2-difluoro-1-[4-methyl-2-(4-trifluoromethyl-phenyl)-thiazol-5-yl]-ethoxymethyl}-phenyl)-4H-[1,2,4]oxadiazol-5-one

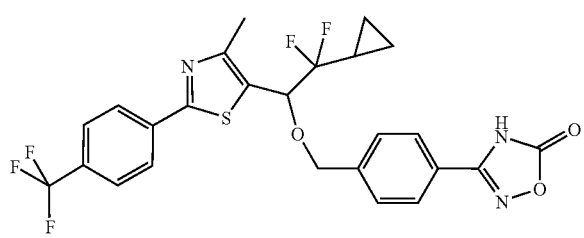

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{2-Cyclopropyl-2,2-difluoro-1-[4-methyl-2-(4-trifluoromethyl-phenyl)-thiazol-5-yl]-ethoxymethyl}-phenyl)-4H-[1,2,4]oxadiazol-5-one was obtained from 2-Cyclopropyl-2,2-difluoro-1-[4-methyl-2-(4-trifluoromethyl-phenyl)-thiazol-5-yl]-ethanol and commercially available 4-Bromomethyl-benzonitrile.

The racemate can be separated into its enantiomers by the method described herein before.

C25H20F5N3O3S (537.51), MS (ESI): 538.0 (M+H$^+$).

EXAMPLE 33

3-(4-{2-(4-Difluoromethyl-phenyl)-2,2-difluoro-1-[4-methyl-2-(4-trifluoromethyl-phenyl)-thiazol-5-yl]-ethoxymethyl}-phenyl)-4H-[1,2,4]oxadiazol-5-one

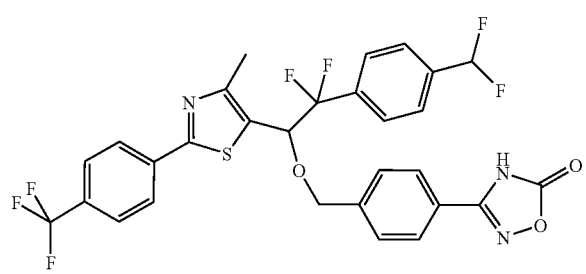

According to the method described for 3-(2-Chloro-4-{2,2,2-trifluoro-1-[4-methyl-2-(4-trifluoromethyl-phenyl)-thiazol-5-yl]-ethoxymethyl}-phenyl)-4H-[1,2,4]oxadiazol-5-one, 3-(4-{2-(4-Difluoromethyl-phenyl)-2,2-difluoro-1-[4-methyl-2-(4-trifluoromethyl-phenyl)-thiazol-5-yl]-ethoxymethyl}-phenyl)-4H-[1,2,4]oxadiazol-5-one was obtained from 2-(4-Difluoromethyl-phenyl)-2,2-difluoro-1-[4-methyl-2-(4-trifluoromethyl-phenyl)-thiazol-5-yl]-ethanol and commercially available 4-Bromomethyl-benzonitrile.

The racemate can be separated into its enantiomers by the method described herein before.

C29H20F7N3O3S (623.55), MS (ESI): 624.4 (M+H$^+$).

The following examples were prepared according to process K:

EXAMPLE 34

3-(2-Fluoro-4-{2-[4-methyl-2-(4-trifluoromethyl-phenyl)-thiazol-5-yl]-hexyl}-phenyl)-4H-[1,2,4]oxadiazol-5-one

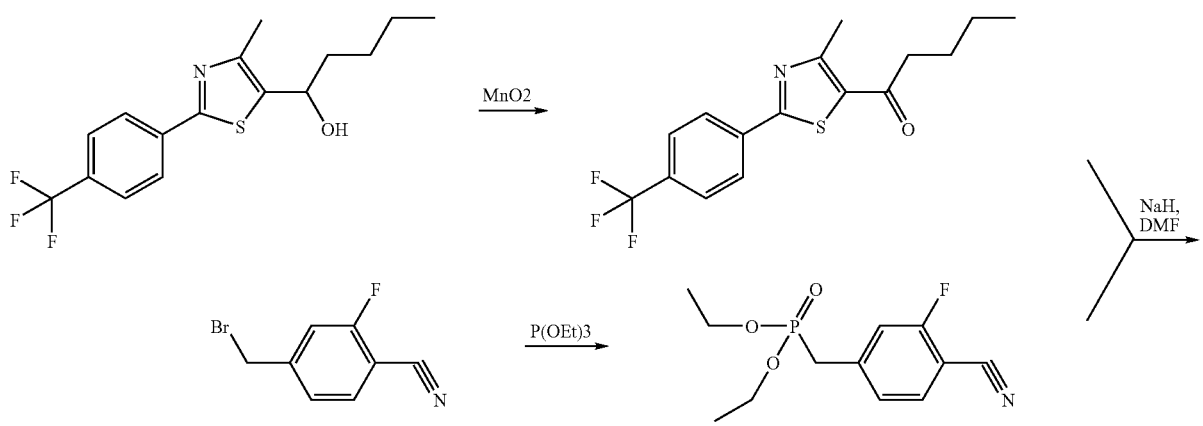

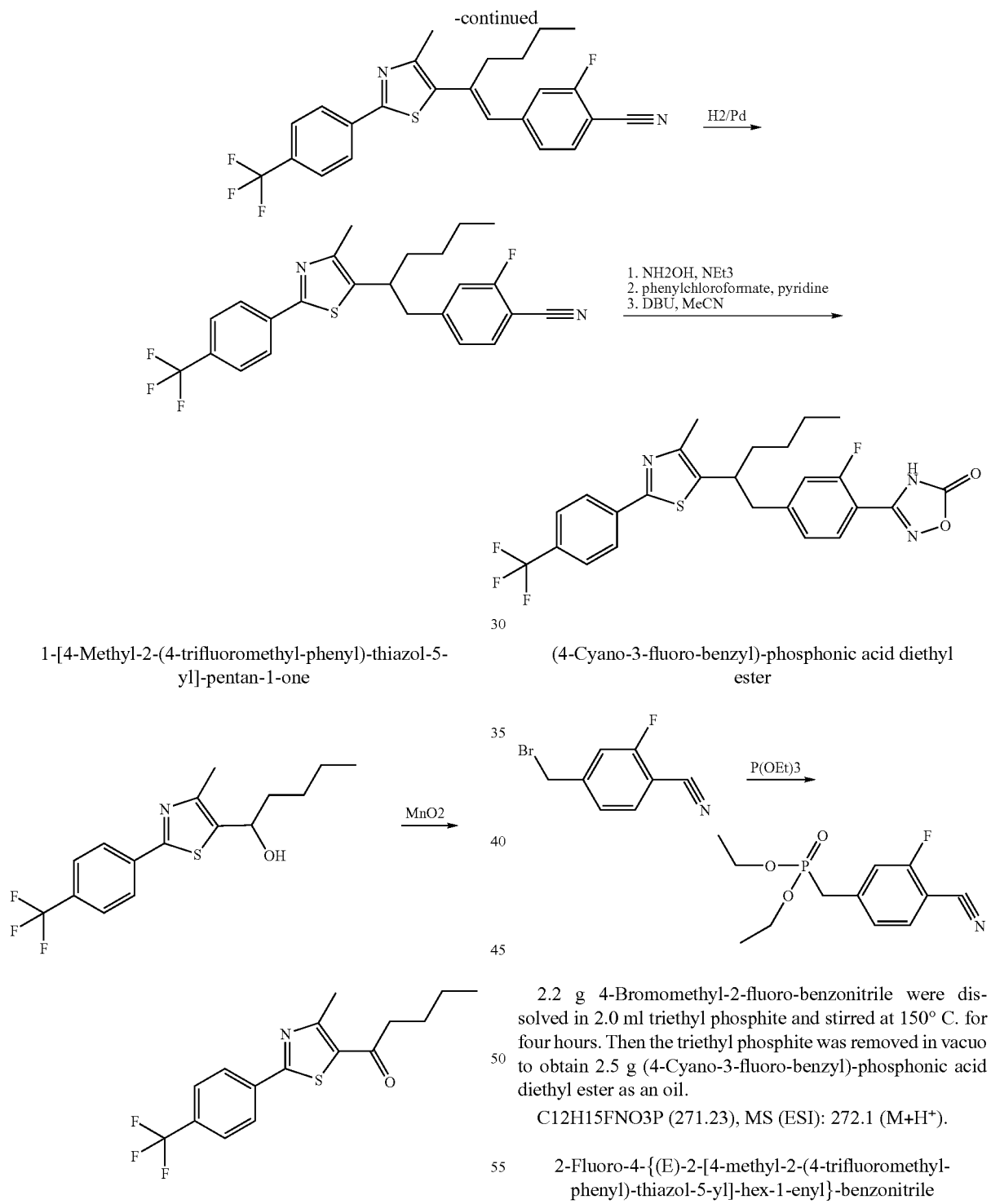

1-[4-Methyl-2-(4-trifluoromethyl-phenyl)-thiazol-5-yl]-pentan-1-one 1.50 g 1-[4-Methyl-2-(4-trifluoromethyl-phenyl)-thiazol-5-yl]-pentan-1-ol were dissolved in 30 ml dichloromethane. 5.46 g manganese(IV)oxide (activated on charcoal) were added and the resulting mixture was heated under reflux for 2.5 hours. The cooled reaction mixture was filtered through a pad of celite. The filtrate was evaporated in vacuo to obtain 1.2 g 1-[4-Methyl-2-(4-trifluoromethyl-phenyl)-thiazol-5-yl]-pentan-1-one as an oil.

C16H16F3NOS (327.37), MS (ESI): 328.1 (M+H$^+$).

(4-Cyano-3-fluoro-benzyl)-phosphonic acid diethyl ester 2.2 g 4-Bromomethyl-2-fluoro-benzonitrile were dissolved in 2.0 ml triethyl phosphite and stirred at 150° C. for four hours. Then the triethyl phosphite was removed in vacuo to obtain 2.5 g (4-Cyano-3-fluoro-benzyl)-phosphonic acid diethyl ester as an oil.

C12H15FNO3P (271.23), MS (ESI): 272.1 (M+H$^+$).

2-Fluoro-4-{(E)-2-[4-methyl-2-(4-trifluoromethyl-phenyl)-thiazol-5-yl]-hex-1-enyl}-benzonitrile

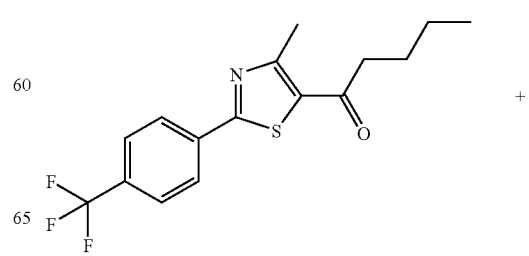

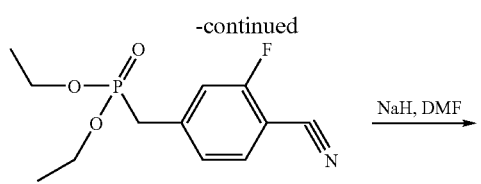

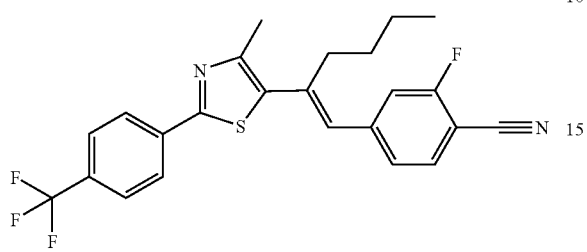

1.0 g (4-Cyano-3-fluoro-benzyl)-phosphonic acid diethyl ester was dissolved in 50 ml tetrahydrofuran and cooled in an ice bath. At 0° C. 103 mg sodium hydride were added and the mixture stirred for fifteen minutes. Then 1.2 g 1-[4-Methyl-2-(4-trifluoromethyl-phenyl)-thiazol-5-yl]-pentan-1-one, dissolved in 20 ml tetrahydrofuran, were added dropwise. The cooling bath was removed and the reaction mixture stirred at room temperature for two hours. Then 1.0 g (4-Cyano-3-fluoro-benzyl)-phosphonic acid diethyl ester and 103 mg sodium hydride were added and the reaction mixture stirred for an additional hour. Then 20 ml water were added and the mixture extracted five times with portions of 25 ml ethyl acetate. The combined organic layers were dried over MgSO4, then the solvent was removed in vacuo to obtain 1.6 g 2-Fluoro-4-{(E)-2-[4-methyl-2-(4-trifluoromethyl-phenyl)-thiazol-5-yl]-hex-1-enyl}-benzonitrile as a yellow oil.

C24H20F4N2S (444.50), MS (ESI): 445.1 (M+H$^+$), Rf(n-heptane:ethyl acetate=1:1)=0.65.

2-Fluoro-4-{2-[4-methyl-2-(4-trifluoromethyl-phenyl)-thiazol-5-yl]-hexyl}-benzonitrile

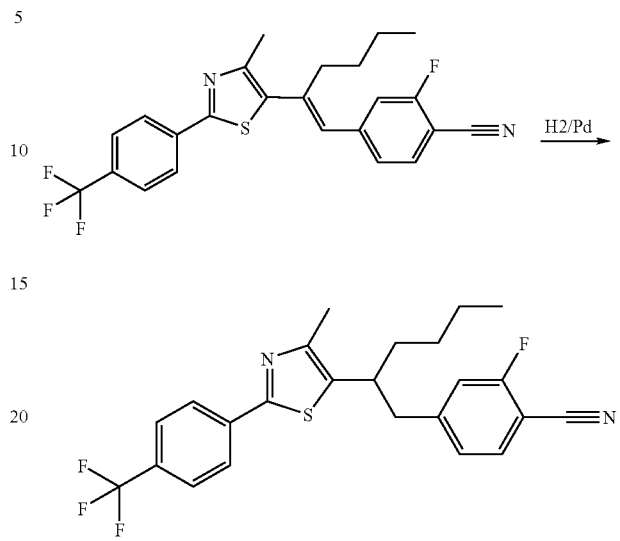

1.6 g 2-Fluoro-4-{(E)-2-[4-methyl-2-(4-trifluoromethyl-phenyl)-thiazol-5-yl]-hex-1-enyl}-benzonitrile were dissolved in a mixture of 10 ml methanol and 10 ml ethyl acetate. 300 mg palladium (5% on charcoal) were added and the mixture stirred at room temperature under a hydrogen atmosphere. After three hours the catalyst was filtered off through a pad of celite and the filtrate evaporated in vacuo. The residue was purified by reversed phase HPLC to obtain 1.2 g 2-Fluoro-4-{2-[4-methyl-2-(4-trifluoromethyl-phenyl)-thiazol-5-yl]-hexyl}-benzonitrile as a lyophilisate. C24H22F4N2S (446.51), MS (ESI): 447.2 (M+H$^+$).

3-(2-Fluoro-4-{2-[4-methyl-2-(4-trifluoromethyl-phenyl)-thiazol-5-yl]-hexyl}-phenyl)-4H-[1,2,4]oxadiazol-5-one

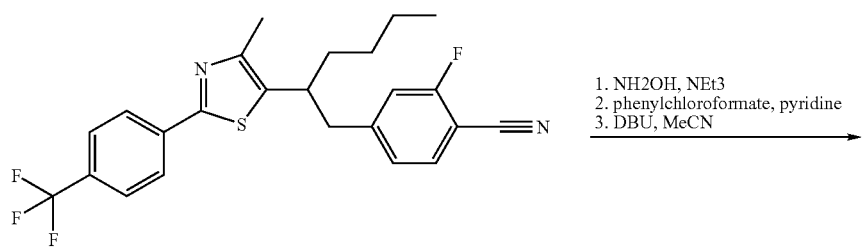

1. NH2OH, NEt3
2. phenylchloroformate, pyridine
3. DBU, MeCN

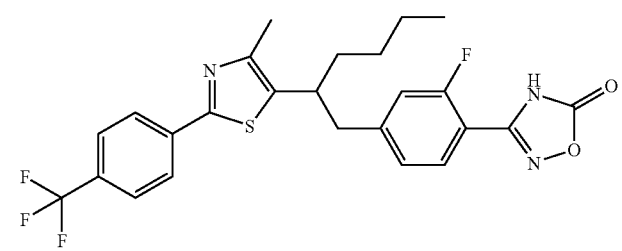

According to the method described for 3-(2-Chloro-4-{1-[4-methyl-2-(4-trifluoromethyl-phenyl)-thiazol-5-yl]-ethoxy}-phenyl)-4H-[1,2,4]oxadiazol-5-one, 3-(2-Fluoro-4-{2-[4-methyl-2-(4-trifluoromethyl-phenyl)-thiazol-5-yl]-hexyl}-phenyl)-4H-[1,2,4]oxadiazol-5-one was obtained from 2-Fluoro-4-{2-[4-methyl-2-(4-trifluoromethyl-phenyl)-thiazol-5-yl]-hexyl}-benzonitrile.

The racemate can be separated into its enantiomers by the method described herein before.

C25H23F4N3O2S (505.54), MS (ESI): 506.1 (M+H$^+$).

The following examples were prepared according to process A:

EXAMPLE 35

3-(2-Fluoro-4-{1-[4-methyl-2-(4-trifluoromethyl-phenyl)-thiazol-5-yl]-propoxy}-phenyl)-4H-1,2,4-oxadiazol-5-one

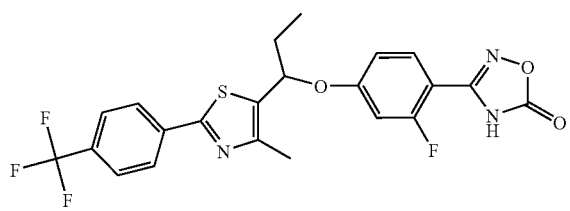

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, 3-(2-fluoro-4-{1-[4-methyl-2-(4-trifluoromethyl-phenyl)-thiazol-5-yl]-propoxy}-phenyl)-4H-1,2,4-oxadiazol-5-one was obtained from 1-[4-methyl-2-(4-trifluoromethyl-phenyl)-thiazol-5-yl]-propan-1-ol and 2-fluoro-4-hydroxybenzonitrile.

C22H17F4N3O3S (479.46), MS (ESI): 480.0 (M+H$^+$).

The racemate was separated into its enantiomers by supercritical fluid chromatography on chiral phase (Chiralpak AD, column 350×50 mm, 20 µm) with 25% methanol/75% carbon dioxide as eluent (120 bars, flow rate: 230 mL/min, UV 230 nm). The enantiomeric excess of each enantiomer was determined by analytical supercritical fluid chromatography on chiral phase (Chiralpak AD, column 250×4.6 mm, 20 µm) with 10% methanol/90% carbon dioxide as eluent (100 bars, flow rate: 3 mL/min, UV 230 nm): levorotatory enantiomer: >99% ee, Rt=5.22 min; dextrorotatory enantiomer: >99% ee, Rt=6.81 min.

EXAMPLE 36

(+)-3-(2-Fluoro-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

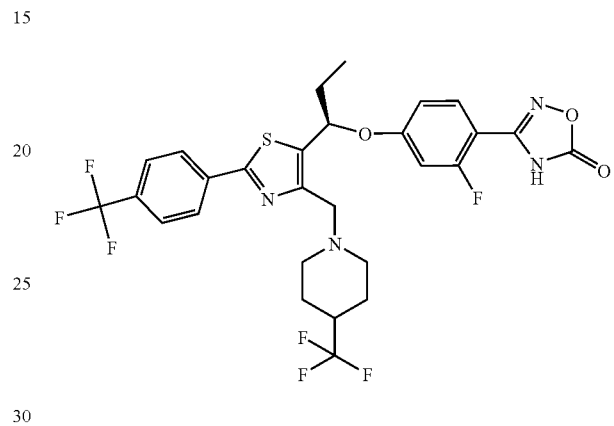

According to the method described for 3-(2-chloro-4-{1-[4-methyl-2-(4-trifluoromethyl-phenyl)-thiazol-5-yl]-ethoxy}-phenyl)-4H-[1,2,4]oxadiazol-5-one, (+)-3-(2-fluoro-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from (S)-1-[2-(4-trifluoromethyl-phenyl)-4-(4-trifluoromethyl-piperidin-1-ylmethyl)-thiazol-5-yl]-propan-1-ol and 2-fluoro-4-hydroxybenzonitrile.

C28H25F7N4O3S (630.59), MS (ESI): 631.2 (M+H$^+$).

The following examples were prepared according to process B:

EXAMPLE 37

3-(2-Difluoromethoxy-4-{1-[4-methyl-2-(4-trifluoromethyl-phenyl)-thiazol-5-yl]-propoxy}-phenyl)-4H-1,2,4-oxadiazol-5-one

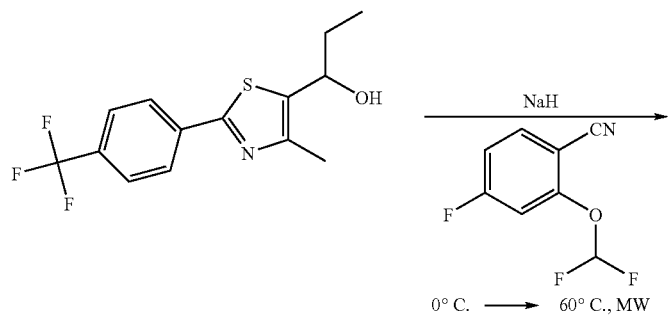

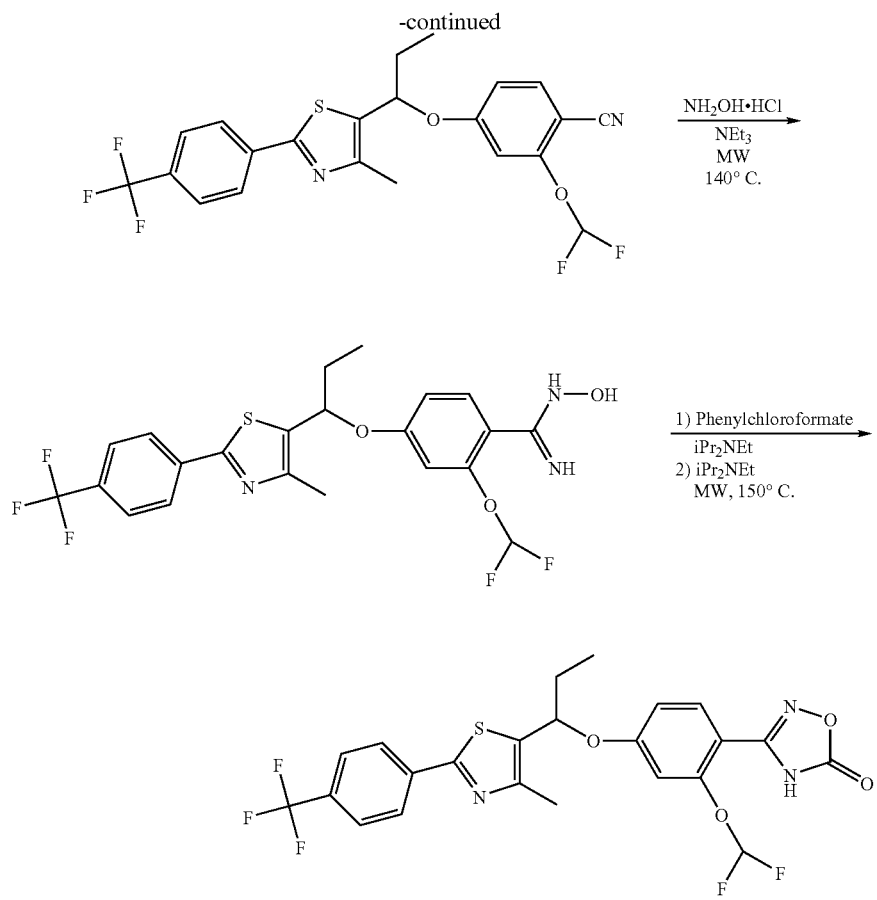

2-Difluoromethoxy-4-{1-[4-methyl-2-(4-trifluoromethyl-phenyl)-thiazol-5-yl]-propoxy}-benzonitrile

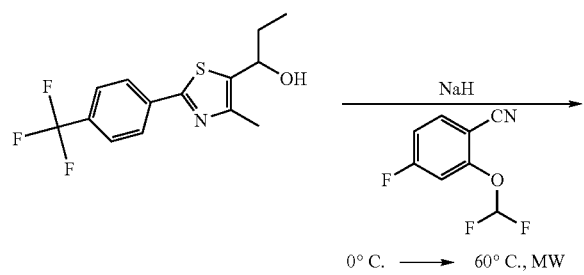

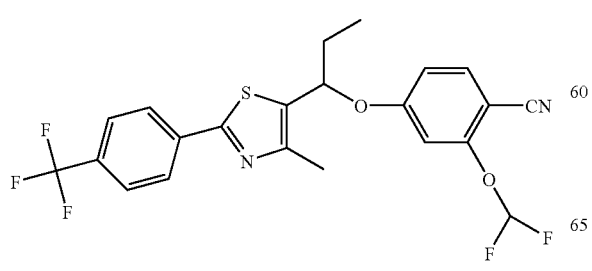

To a solution of 1.7 g of 1-[4-methyl-2-(4-trifluoromethyl-phenyl)-thiazol-5-yl]-propan-1-ol in 4.7 mL of dimethylformamide at 5° C. was added 250 mg of a 55% suspension of sodium hydride in mineral oil. The reaction volume was completed with dimethylformamide to about 8.5 mL. The reaction mixture was stirred for 30 minutes at 5° C. 4.3 mL of the resulting mixture was slowly added to a solution of 450 mg of 2-difluoromethoxy-4-fluoro-benzonitrile in 2 mL of dimethylformamide at 5° C. The resulting mixture was stirred at 5° C. allowing the temperature to warm up to room temperature. It was then heated in a sealed tube to 60° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 100 to heptane 50/ethyl acetate 50) to give 490 mg of 2-difluoromethoxy-4-{1-[4-methyl-2-(4-trifluoromethyl-phenyl)-thiazol-5-yl]-propoxy}-benzonitrile.

C22H17F5N2O2S (468.45), MS (ESI): (M+H$^+$) 469.0 (M+H$^+$).

2-Difluoromethoxy-N-hydroxy-4-{1-[4-methyl-2-(4-trifluoromethyl-phenyl)-thiazol-5-yl]-propoxy}-benzamidine

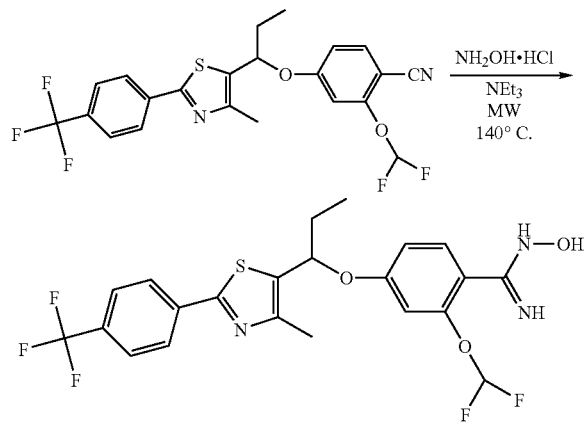

To a solution of 485 mg of 2-difluoromethoxy-4-{1-[4-methyl-2-(4-trifluoromethyl-phenyl)-thiazol-5-yl]-propoxy}-benzonitrile in 10 mL of methanol was added 4.166 mL of triethylamine followed by 316 mg of hydroxylamine hydrochloride. The resulting mixture was heated in a sealed tube to 140° C. under microwave irradiation for 30 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (gradient from heptane 100 to heptane 60/ethyl acetate 40) to give 320 mg of 2-difluoromethoxy-N-hydroxy-4-{1-[4-methyl-2-(4-trifluoromethyl-phenyl)-thiazol-5-yl]-propoxy}-benzamidine.

C22H20F5N3O3S (501.48), MS (ESI): 502.0 (M+H$^+$).

3-(2-Difluoromethoxy-4-{1-[4-methyl-2-(4-trifluoromethyl-phenyl)-thiazol-5-yl]-propoxy}-phenyl)-4H-1,2,4-oxadiazol-5-one To a solution of 315 mg of 2-difluoromethoxy-N-hydroxy-4-{1-[4-methyl-2-(4-trifluoromethyl-phenyl)-thiazol-5-yl]-propoxy}-benzamidine in 6.5 mL of tetrahydrofuran at 0° C. was added 1.5 mL of N,N-diisopropylethylamine followed by 0.08 mL of phenyl chloroformate. The resulting mixture was stirred for 5 minutes at 0° C. then poured into water and extracted with dichloromethane. The organic extracts were dried over magnesium sulfate, filtered and concentrated under reduced pressure. The residue was dissolved 6.5 mL of tetrahydrofuran and 0.3 mL of N,N-diisopropylethylamine. The resulting solution was heated in a sealed tube to 150° C. under microwave irradiation for 15 minutes. After allowing it to cool down to room temperature, the mixture was poured into water and extracted with dichloromethane. The organic extracts were dried over magnesium sulfate, filtered and concentrated under reduced pressure. The crude product was purified by column chromatography on silica gel (diisopropyl ether 100 followed by a gradient from dichloromethane 100 to dichloromethane 90/methanol 10) to give 31 mg of 3-(2-difluoromethoxy-4-{1-[4-methyl-2-(4-trifluoromethyl-phenyl)-thiazol-5-yl]-propoxy}-phenyl)-4H-1,2,4-oxadiazol-5-one.

C23H18F5N3O4S (527.47), MS (ESI): 528.0 (M+H$^+$).

The racemate was separated into its enantiomers by supercritical fluid chromatography on chiral phase (Chiralpak AD, column 350×50 mm, 20 μm) with 25% methanol/75% carbon dioxide as eluent (108 bars, flow rate: 200 mL/min, UV 254 nm). The enantiomeric excess of each enantiomer was determined by analytical supercritical fluid chromatography on chiral phase (Chiralpak AD, column 250×4.6 mm, 5 μm) with 20% methanol/80% carbon dioxide as eluent (100 bars, flow rate: 3 mL/min, UV 220 nm): levorotatory enantiomer: >99% ee, Rt=3.20 min; dextrorotatory enantiomer: >99% ee, Rt=6.30 min.

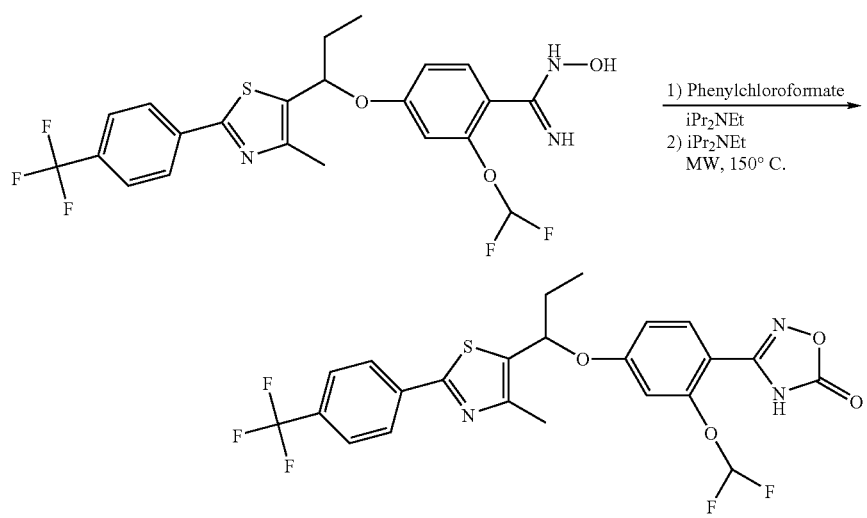

EXAMPLE 38

3-(2-Methoxy-4-{1-[4-methyl-2-(4-trifluoromethyl-phenyl)-thiazol-5-yl]-propoxy}-phenyl)-4H-1,2,4-oxadiazol-5-one

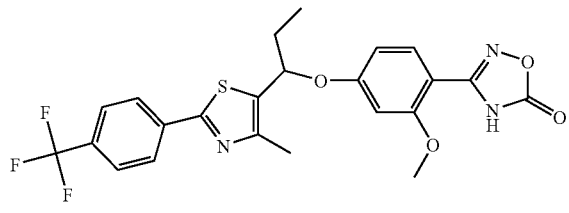

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(2-methoxy-4-{1-[4-methyl-2-(4-trifluoromethyl-phenyl)-thiazol-5-yl]-propoxy}-phenyl)-4H-1,2,4-oxadiazol-5-one was obtained from 1-[4-methyl-2-(4-trifluoromethyl-phenyl)-thiazol-5-yl]-propan-1-ol and 4-fluoro-2-methoxybenzonitrile.

C23H20F3N3O4S (491.49), MS (ESI): 492 (M+H+).

The racemate was separated into its enantiomers by HPLC on chiral phase (Chiralcel OJ-H, column 210×20 mm, 5 μm) with 30% ethanol/70% heptane as eluent (flow rate: 25 mL/min, UV 254 nm). The enantiomeric excess of each enantiomer was determined by analytical HPLC on chiral phase (Chiralcel OJ-H, column 250×4.6 mm, 5 μm) with 30% ethanol/70% heptane as eluent (flow rate: 1 mL/min, UV 254 nm): levorotatory enantiomer: >99% ee, Rt=8.06 min; dextrorotatory enantiomer: >99% ee, Rt=11.66 min.

(+)-3-(2-Methoxy-4-{(R)-1-[4-methyl-2-(4-trifluoromethyl-phenyl)-thiazol-5-yl]-propoxy}-phenyl)-4H-1,2,4-oxadiazol-5-one

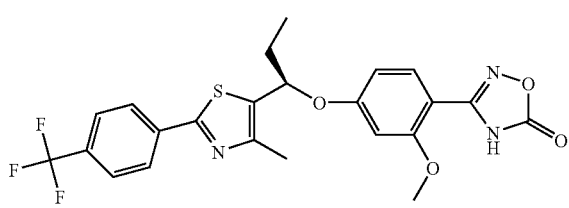

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, (+)-3-(2-methoxy-4-{(R)-1-[4-methyl-2-(4-trifluoromethyl-phenyl)-thiazol-5-yl]-propoxy}-phenyl)-4H-1,2,4-oxadiazol-5-one was obtained from (+)-(R)-1-[4-methyl-2-(4-trifluoromethyl-phenyl)-thiazol-5-yl]-propan-1-ol and 4-fluoro-2-methoxybenzonitrile.

C23H20F3N3O4S (491.49), MS (ESI): 492.1 (M+H+).

The enantiomeric excess of this dextrorotatory enantiomer was determined by analytical HPLC on chiral phase (Chiralcel OJ-H, column 250×4.6 mm, 5 μm) with 30% ethanol/70% heptane as eluent (flow rate: 1 mL/min, UV 254 nm) by comparison with the racemic mixture: ee 96%, Rt=10.43 min.

EXAMPLE 39

3-(2-Hydroxy-4-{1-[4-methyl-2-(4-trifluoromethyl-phenyl)-thiazol-5-yl]-propoxy}-phenyl)-4H-1,2,4-oxadiazol-5-one

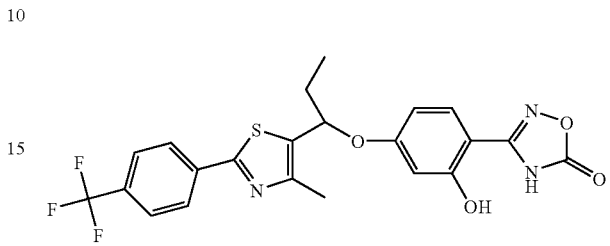

To a stirred solution of 136 mg of 3-(2-methoxy-4-{1-[4-methyl-2-(4-trifluoromethyl-phenyl)-thiazol-5-yl]-propoxy}-phenyl)-4H-1,2,4-oxadiazol-5-one in 5 mL of dichloromethane at −70° C. was added 0.6 mL of a 1 M solution of boron tribromide in dichloromethane. After 1 h at −60° C., the reaction mixture was poured into methanol and a saturated aqueous solution of NaHCO3 then extracted with dichloromethane. The combined organic layers were dried over magnesium sulfate, filtered and concentrated under reduced pressure. The residue was purified by column chromatography on silica gel (gradient of dichloromethane/methanol from 100/0 to 90/10) to give 22 mg of 3-(2-hydroxy-4-{1-[4-methyl-2-(4-trifluoromethyl-phenyl)-thiazol-5-yl]-propoxy}-phenyl)-4H-1,2,4-oxadiazol-5-one.

C22H18F3N3O4S (477.47), MS (ESI): 478 (M+H+).

EXAMPLE 40

3-(5-Fluoro-2-methoxy-4-{1-[4-methyl-2-(4-trifluoromethyl-phenyl)-thiazol-5-yl]-propoxy}-phenyl)-4H-1,2,4-oxadiazol-5-one

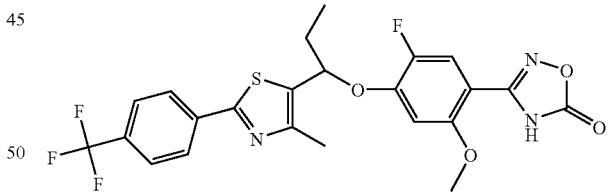

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(5-fluoro-2-methoxy-4-{1-[4-methyl-2-(4-trifluoromethyl-phenyl)-thiazol-5-yl]-propoxy}-phenyl)-4H-1,2,4-oxadiazol-5-one was obtained from 1-[4-methyl-2-(4-trifluoromethyl-phenyl)-thiazol-5-yl]-propan-1-ol and commercially available 4,5-difluoro-2-methoxybenzonitrile.

C23H19F4N3O4S (509.48), MS (ESI): 509.9 (M+H+).

The racemate was separated into its enantiomers by supercritical fluid chromatography on chiral phase (Chiralpak OJ, column 250×21 mm, 5 μm) with 15% methanol/85% carbon dioxide as eluent (flow rate: 90 mL/min, UV 210 nm). The enantiomeric excess of each enantiomer was determined by analytical supercritical fluid chromatography on chiral phase (Chiralpak OJ, column 250×4.6 mm, 10 μm) with 10% methanol/90% carbon dioxide as eluent (100 bars, flow rate: 3 mL/min, UV 210 nm): levorotatory enantiomer: >99% ee, Rt=8.67 min; dextrorotatory enantiomer: >99% ee, Rt=11.42 min.

(+)-3-(5-Fluoro-2-methoxy-4-{(R)-1-[4-methyl-2-(4-trifluoromethyl-phenyl)-thiazol-5-yl]-propoxy}-phenyl)-4H-1,2,4-oxadiazol-5-one

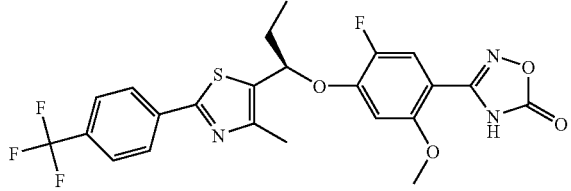

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, (+)-3-(5-fluoro-2-methoxy-4-{(R)-1-[4-methyl-2-(4-trifluoromethyl-phenyl)-thiazol-5-yl]-propoxy}-phenyl)-4H-1,2,4-oxadiazol-5-one was obtained from (+)-(R)-1-[4-methyl-2-(4-trifluoromethyl-phenyl)-thiazol-5-yl]-propan-1-ol and 4,5-difluoro-2-methoxybenzonitrile.

C23H19F4N3O4S (509.48), MS (ESI): 510.0 (M+H+).

The enantiomeric excess of this dextrorotatory enantiomer was determined by analytical HPLC on chiral phase (Chiralcel OJ-H, column 250×4.6 mm, 5 μm) with 30% ethanol/70% heptane as eluent (flow rate: 1 mL/min, UV 254 nm) by comparison with the racemic mixture: ee 96%, Rt=8.63 min.

EXAMPLE 41

(+)-3-(2-Difluoromethoxy-5-fluoro-4-{(R)-1-[4-methyl-2-(4-trifluoromethyl-phenyl)-thiazol-5-yl]-propoxy}-phenyl)-4H-1,2,4-oxadiazol-5-one

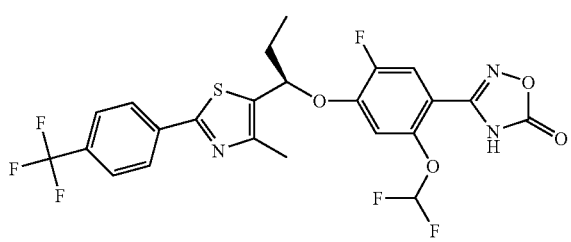

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, (+)-3-(2-difluoromethoxy-5-fluoro-4-{(R)-1-[4-methyl-2-(4-trifluoromethyl-phenyl)-thiazol-5-yl]-propoxy}-phenyl)-4H-1,2,4-oxadiazol-5-one was obtained from (+)-(R)-1-[4-methyl-2-(4-trifluoromethyl-phenyl)-thiazol-5-yl]-propan-1-ol and 2-difluoromethoxy-4,5-difluoro-benzonitrile.

C23H17F6N3O4S (545.46), MS (ESI): 546.0 (M+H+).

EXAMPLE 42

3-(2-Methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

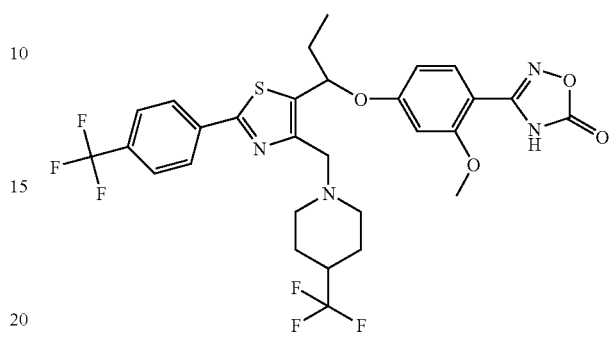

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(2-methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and 4-fluoro-2-methoxy-benzonitrile.

C29H28F6N4O4S (642.63), MS (ESI): 643.2 (M+H+).

The racemate was separated into its enantiomers by supercritical fluid chromatography on chiral phase (Chiralpak AD, column 250×50 mm, 20 μm) with 35% methanol/65% carbon dioxide as eluent (70 bars, 30° C., flow rate: 250 mL/min, UV 254 nm). The enantiomeric excess of each enantiomer was determined by analytical supercritical fluid chromatography on chiral phase (Chiralpak AD, column 250×4.6 mm, 10 μm) with 35% methanol/65% carbon dioxide as eluent (100 bars, flow rate: 3 mL/min, UV 254 nm): levorotatory enantiomer: >99% ee, Rt=2.7 min; dextrorotatory enantiomer: >99% ee, Rt=5.7 min.

EXAMPLE 43

3-(5-Fluoro-2-methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

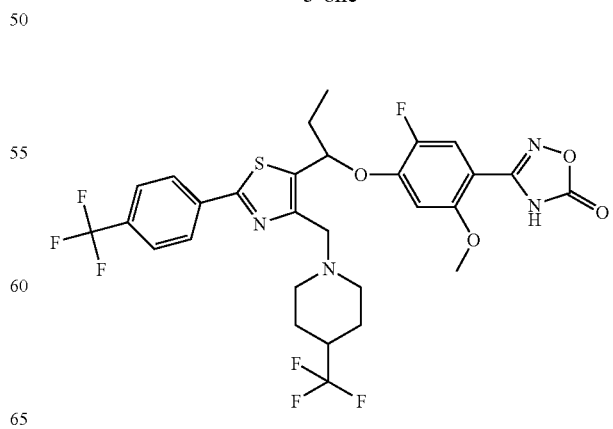

According to the method described for 3-(2-difluoromethoxy-4-{1-[4-methyl-2-(4-trifluoromethyl-phenyl)- thiazol-5-yl]-propoxy}-phenyl)-4H-1,2,4-oxadiazol-5-one, 3-(5-fluoro-2-methoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and commercially available 4,5-difluoro-2-methoxy-benzonitrile.

C29H27F7N4O4S (660.62), MS (ESI): 661.0 (M+H$^+$).

The racemate was separated into its enantiomers by supercritical fluid chromatography on chiral phase (Chiralpak AD, column 250×50 mm, 20 μm) with 10% methanol/90% carbon dioxide as eluent (140 bars, flow rate: 250 mL/min, UV 254 nm). The enantiomeric excess of each enantiomer was determined by analytical supercritical fluid chromatography on chiral phase (Chiralpak AD, column 250×4.6 mm, 20 μm) with 10% methanol/90% carbon dioxide as eluent (100 bars, flow rate: 3 mL/min, UV 254 nm): levorotatory enantiomer: >99% ee, Rt=11.89 min; dextrorotatory enantiomer: >99% ee, Rt=16.92 min.

EXAMPLE 44

3-(2-(2,2,2-Trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

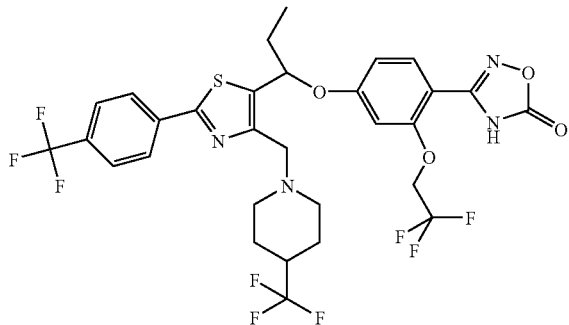

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(2-(2,2,2-trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and 4-fluoro-2-(2,2,2-trifluoro-ethoxy)-benzonitrile.

C30H27F9N4O4S (710.62), MS (ESI): 712.1 (M+H$^+$).

The racemate was separated into its enantiomers by supercritical fluid chromatography on chiral phase (Chiralpak AD-H, column 20 mm diameter, 5 μm) with 15% methanol/85% carbon dioxide as eluent (70 bars, 30° C., flow rate: 100 mL/min, UV 254 nm). The enantiomeric excess of each enantiomer was determined by analytical supercritical fluid chromatography on chiral phase (Chiralpak AD-H, column 250×4.6 mm, 5 μm) with 15% methanol/85% carbon dioxide as eluent (100 bars, flow rate: 3 mL/min, UV 254 nm): first enantiomer: >99% ee, Rt=2.85 min; second enantiomer: >99% ee, Rt=5.74 min.

EXAMPLE 45

3-(2-Difluoromethoxy-4-{1-[2-(4-trifluoromethyl-phenyl)-4-(4-trifluoromethyl-Piperidin-1-ylmethyl)-thiazol-5-yl]-propoxy}-phenyl)-4H-1,2,4-oxadiazol-5-one

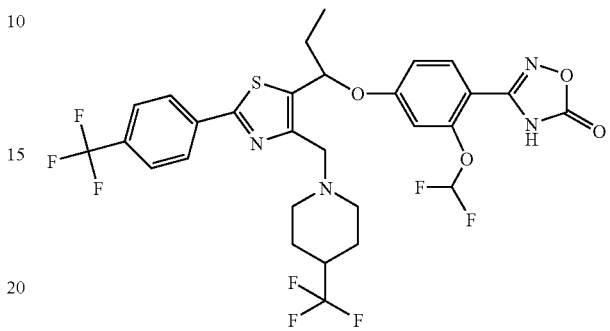

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(2-difluoromethoxy-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and 2-difluoromethoxy-4-fluoro-benzonitrile.

C29H26F8N4O4S (678.61), MS (ESI): 680.4 (M+H$^+$).

The racemate was separated into its enantiomers by supercritical fluid chromatography on chiral phase (Chiralpak AD, column 250×50 mm, 20 μm) with 20% acetonitrile/80% carbon dioxide as eluent (105 bars, flow rate: 200 mL/min, UV 254 nm). The enantiomeric excess of each enantiomer was determined by analytical supercritical fluid chromatography on chiral phase (Chiralpak AD-H, column 250×4.6 mm, 5 μm) with 15% methanol/85% carbon dioxide as eluent (100 bars, flow rate: 3 mL/min, UV 254 nm): levorotatory enantiomer: >99% ee, Rt=3.14 min; dextrorotatory enantiomer: >99% ee, Rt=5.34 min.

(+)-3-(2-Difluoromethoxy-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

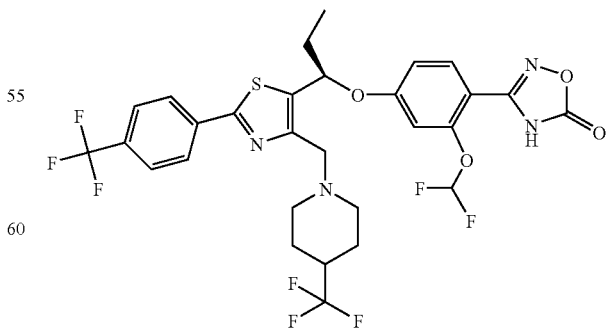

According to the method described for 3-(2-difluoromethoxy-4-{1-[4-methyl-2-(4-trifluoromethyl-phenyl)- thiazol-5-yl]-propoxy}-phenyl)-4H-1,2,4-oxadiazol-5-one (except for the hydroxylamine addition step which was performed under microwave irradiation at 100° C. for 2 h), (+)-3-(2-difluoromethoxy-4-{(R)-1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from (R)-1-[2-(4-trifluoromethyl-phenyl)-4-(4-trifluoromethyl-piperidin-1-ylmethyl)-thiazol-5-yl]-propan-1-ol and 2-difluoromethoxy-4-fluoro-benzonitrile.

C29H26F8N4O4S (678.61), MS (ESI): 679.3 (M+H$^+$).

EXAMPLE 46

3-(2-Difluoromethoxy-5-fluoro-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

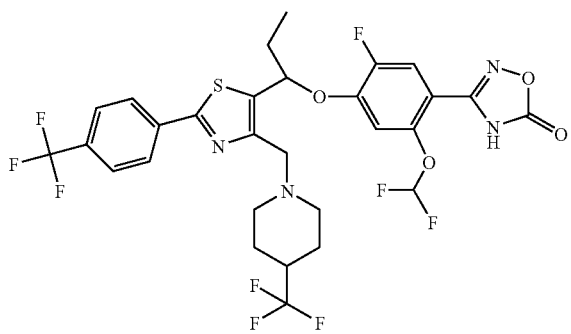

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-(2-difluoromethoxy-5-fluoro-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and 2-difluoromethoxy-4,5-difluoro-benzonitrile.

C29H25F9N4O4S (696.60), MS (ESI): 698.5 (M+H$^+$).

The racemate was separated into its enantiomers by supercritical fluid chromatography on chiral phase (Chiralpak AD-H, column 250×50 mm, 5 μm) with 5% methanol/95% carbon dioxide as eluent (129 bars, flow rate: 100 mL/min, UV 254 nm). The enantiomeric excess of each enantiomer was determined by analytical supercritical fluid chromatography on chiral phase (Chiralpak AD-H, column 250×4.6 mm, 5 μm) with 5% methanol/95% carbon dioxide as eluent (100 bars, flow rate: 3 mL/min, UV 254 nm): levorotatory enantiomer: >99% ee, Rt=10.1 min; dextrorotatory enantiomer: >99% ee, Rt=15.5 min.

The following examples were prepared according to process J:

EXAMPLE 47

3-[5-Fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one

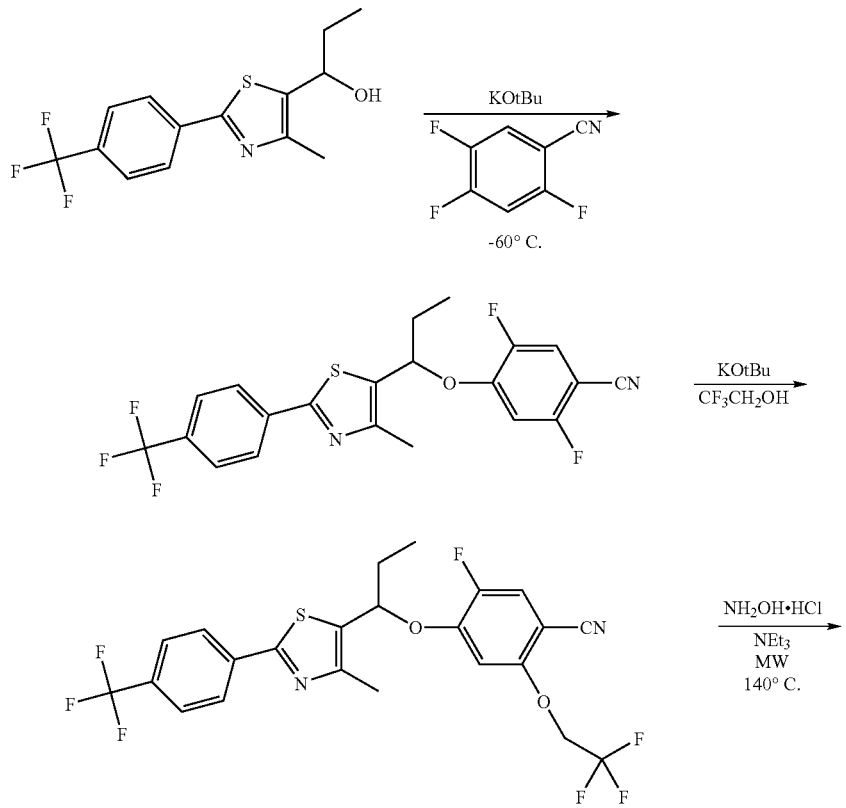

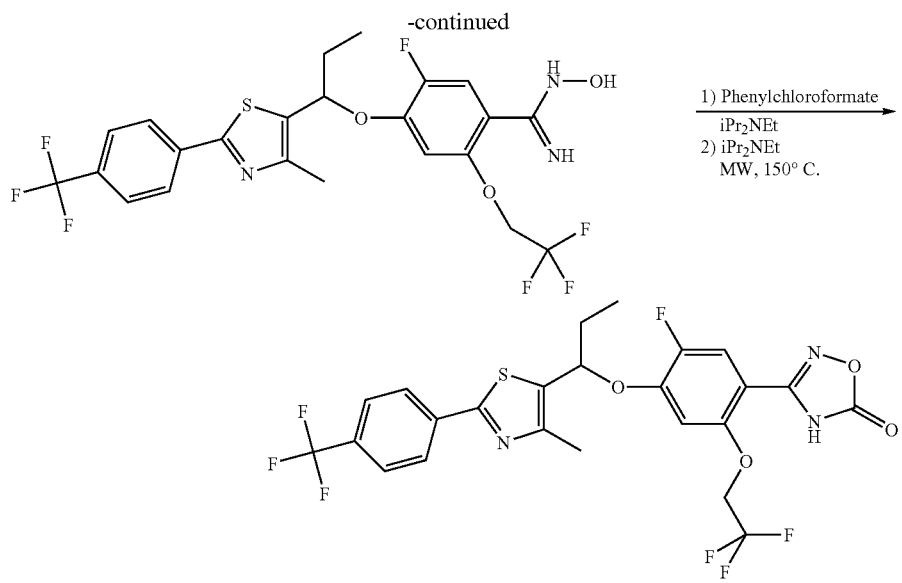

2,5-Difluoro-4-{1-[4-methyl-2-(4-trifluoromethyl-phenyl)-thiazol-5-yl]-propoxy}-benzonitrile 5-Fluoro-4-{1-[4-methyl-2-(4-trifluoromethyl-phenyl)-thiazol-5-yl]-propoxy}-2-(2,2,2-trifluoro-ethoxy)-benzonitrile

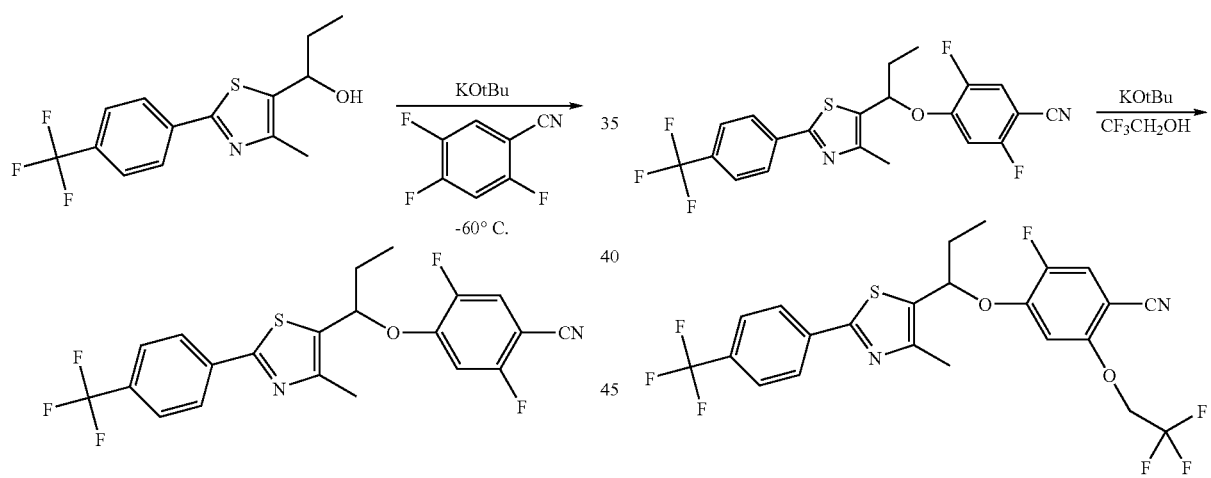

To a solution of 900 mg of 1-[4-methyl-2-(4-trifluoromethyl-phenyl)-thiazol-5-yl]-propan-1-ol in 2 mL of tetrahydrofuran at 5° C. was slowly added 3.3 mL of a molar solution of potassium tert-butoxide in tert-butanol. After stirring at 5° C. for 30 minutes, the resulting solution was slowly added to a solution of 469 mg of 2,4,5-trifluoro-benzonitrile in 2 mL of tetrahydrofuran at −60° C. The resulting mixture was stirred for 1 h at −60° C. then stirred overnight allowing the temperature to warm up to room temperature. It was then poured into water and extracted with dichloromethane. The organic extracts were dried over magnesium sulfate, filtered and concentrated under reduced pressure. The crude product was purified by column chromatography on silica gel (gradient from heptane 100 to heptane 80/ethyl acetate 20) to give 1.25 g of 2,5-difluoro-4-{1-[4-methyl-2-(4-trifluoromethyl-phenyl)-thiazol-5-yl]-propoxy}-benzonitrile.

C21H15F5N2OS (438.42), MS (ESI): 439.0 (M+H$^+$).

To a solution of 342 mg of trifluoroethanol in 2.1 mL of tetrahydrofuran at 5° C. was slowly added 4 mL of a molar solution of potassium tert-butoxide in tert-butanol. After stirring at 5° C. for 30 minutes, the resulting solution was slowly added to a solution of 1.25 g of 2,5-difluoro-4-{1-[4-methyl-2-(4-trifluoromethyl-phenyl)-thiazol-5-yl]-propoxy}-benzonitrile in 5.6 mL of tetrahydrofuran at −60° C. The resulting mixture was stirred overnight allowing the temperature to warm up to room temperature. It was then poured into water and extracted with dichloromethane. The organic extracts were dried over magnesium sulfate, filtered and concentrated under reduced pressure. The crude product was purified by column chromatography on silica gel (gradient from heptane 100 to heptane 70/ethyl acetate 30) to give 1.09 g of 5-fluoro-4-{1-[4-methyl-2-(4-trifluoromethyl-phenyl)-thiazol-5-yl]-propoxy}-2-(2,2,2-trifluoro-ethoxy)-benzonitrile.

C23H17F7N2O2S (518.45), MS (ESI): 519.0 (M+H$^+$).

3-[5-Fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one

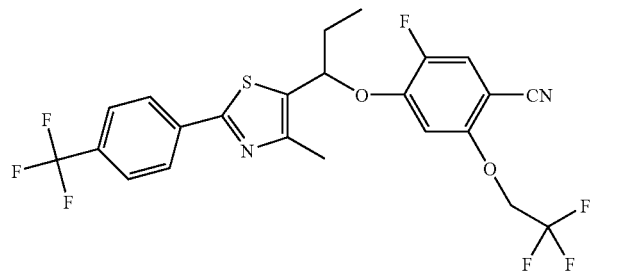

NH₂OH·HCl
NEt₃
MW
140° C.

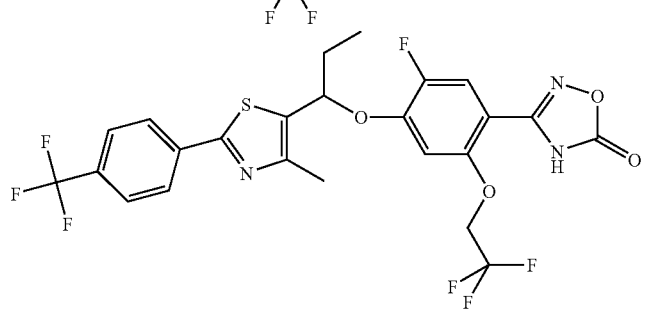

1) Phenylchloroformate
iPr₂NEt
2) iPr₂NEt
MW, 150° C.

According to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, 3-[5-fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one was obtained from 5-fluoro-4-{1-[4-methyl-2-(4-trifluoromethyl-phenyl)-thiazol-5-yl]-propoxy}-2-(2,2,2-trifluoro-ethoxy)-benzonitrile.

C24H18F7N3O4S (577.48), MS (ESI): 578.0 (M+H⁺).

The racemate was separated into its enantiomers by supercritical fluid chromatography on chiral phase (Chiralpak AD, column 350×50 mm, 20 μm) with 15% methanol/85% carbon dioxide as eluent (123 bars, flow rate: 250 mL/min, UV 230 nm). The enantiomeric excess of each enantiomer was determined by analytical supercritical fluid chromatography on chiral phase (Chiralpak AD, column 250×4.6 mm, 205 μm) with 10% methanol/90% carbon dioxide as eluent (100 bars, flow rate: 3 mL/min, UV 230 nm): levorotatory enantiomer: >99% ee, Rt=5.22 min; dextrorotatory enantiomer: >99% ee, Rt=6.81 min.

3-[5-fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one can also be prepared according to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one by starting from 1-[4-methyl-2-(4-trifluoromethyl-phenyl)-thiazol-5-yl]-propan-1-ol and 4,5-difluoro-2-(2,2,2-trifluoro-ethoxy)-benzonitrile.⁶

⁶ WO2005/111003

EXAMPLE 48

3-[4-{1-[4-Methyl-2-(4-trifluoromethyl-phenyl)-thiazol-5-yl]-propoxy}-2-(2,2,2-trifluoro-ethoxy)-phenyl]-4H-1,2,4-oxadiazol-5-one

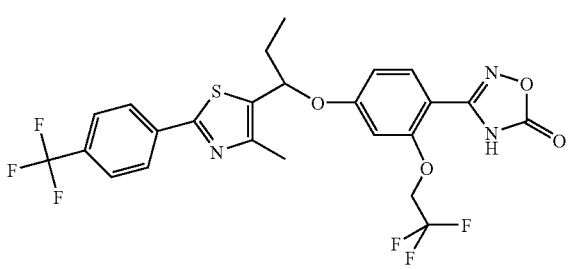

According to the method described for 3-[5-fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one, 3-[4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one was obtained from 1-[4-methyl-2-(4-trifluoromethyl-phenyl)-thiazol-5-yl]-propan-1-ol and 2-fluoro-4-{1-[4-methyl-2-(4-trifluoromethyl-phenyl)-thiazol-5-yl]-propoxy}-benzonitrile that was prepared according to process A.

C24H19F6N3O4S (559.49), MS (ESI): 560 (M+H⁺).

The racemate was separated into its enantiomers by supercritical fluid chromatography on chiral phase (Chiralpak AD, column 250×50 mm, 5 µm) with 25% MeOH and 0.1% triethylamine in carbon dioxide as eluent (130 bars, flow rate: 90 mL/min, UV 205 nm). The enantiomeric excess of each enantiomer was determined by analytical supercritical fluid chromatography on chiral phase (Chiralpak AD, column 250×4.6 mm, 5 µm) with 20% MeOH and 0.1% triethylamine in carbon dioxide as eluent (100 bars, flow rate: 3 mL/min, UV 205 nm): levorotatory enantiomer: >99% ee, Rt=2.94 min; dextrorotatory enantiomer: >99% ee, Rt=5.11 min.

(+)-3-[4-{(R)-1-[4-Methyl-2-(4-trifluoromethyl-phenyl)-thiazol-5-yl]-propoxy}-2-(2,2,2-trifluoro-ethoxy)-phenyl]-4H-1,24-oxadiazol-5-one

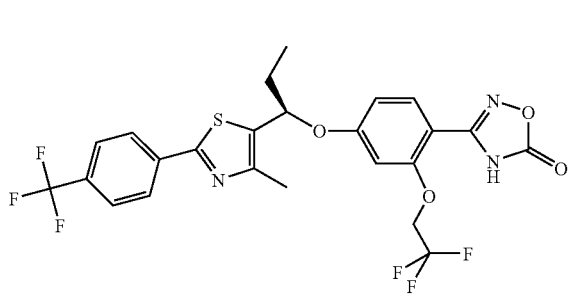

Following process B, according to the method described for 3-(2-difluoromethoxy-4-{1-[4-methyl-2-(4-trifluoromethyl-phenyl)-thiazol-5-yl]-propoxy}-phenyl)-4H-1,2,4-oxadiazol-5-one, (+)-3-[4-{(R)-1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one was obtained from (+)-(R)-1-[4-methyl-2-(4-trifluoromethyl-phenyl)-thiazol-5-yl]-propan-1-ol and 4-fluoro-2-(2,2,2-trifluoro-ethoxy)-benzonitrile.

C24H19F6N3O4S (559.49), MS (ESI): 560.1 (M+H$^+$).

The enantiomeric excess of this dextrorotatory enantiomer was determined by analytical supercritical fluid chromatography on chiral phase (Chiralpak AD, column 250×4.6 mm, 5 µm) with 20% methanol/80% carbon dioxide as eluent (100 bars, flow rate: 3 mL/min, UV 254 nm) by comparison with the racemic mixture: >99% ee, Rt=5.49 min.

EXAMPLE 49

3-(5-Fluoro-2-(2,2,2-trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one

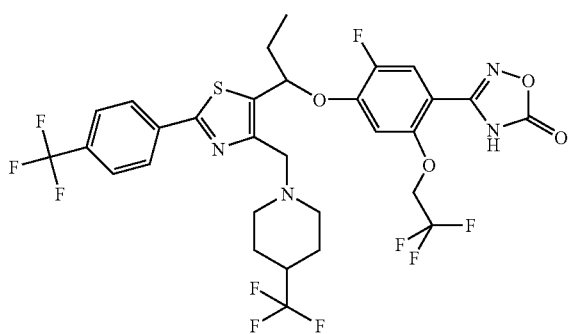

According to the method described for 3-[5-fluoro-4-{1-[4-methyl-2-(4-trifluoromethyl-phenyl)-thiazol-5-yl]-propoxy}-2-(2,2,2-trifluoro-ethoxy)-phenyl]-4H-1,2,4-oxadiazol-5-one, 3-(5-fluoro-2-(2,2,2-trifluoro-ethoxy)-4-{1-[2-(4-trifluoromethyl-phenyl)-4-(4-trifluoromethyl-piperidin-1-ylmethyl)-thiazol-5-yl]-propoxy}-phenyl)-4H-1,2,4-oxadiazol-5-one was obtained from 1-[2-(4-trifluoromethyl-phenyl)-4-(4-trifluoromethyl-piperidin-1-ylmethyl)-thiazol-5-yl]-propan-1-ol and 2,4,5-trifluoro-benzonitrile.

C30H26F10N4O4S (728.61), MS (ESI): 730.6 (M+H$^+$).

What is claimed is:
1. A compound of formula I:

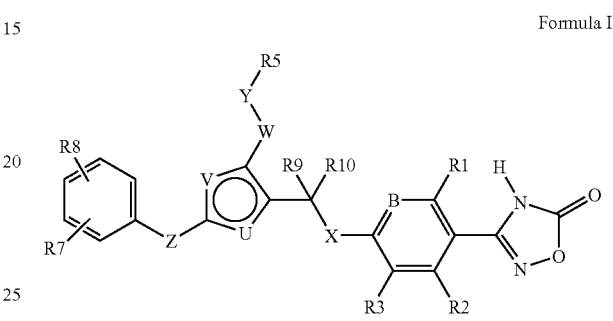

Formula I wherein
R1 is selected from the group consisting of H, halogen, (C1-C8) alkyl, (C0-C4) alkylene-O—(C0-C4) alkylene-H, (C3-C7) cycloalkyl, SCH3, CN and (C6-C10) aryl, wherein alkyl, alkylene and aryl are unsubstituted or 1- to 5-fold substituted by F;

B is C(R4) or N;

R2 and R3 are independently selected from the group consisting of H, halogen, (C1-C8) alkyl, (C0-C4) alkylene-O—(C0-C4) alkylene-H, (C3-C7) cycloalkyl, SCH3, CN and (C6-C10) aryl, wherein alkyl, alkylene and aryl are unsubstituted or 1- to 5-fold substituted by F;

R2 and R3 together with the carbon atoms to which they are bonded form a (C6-C10) aryl or a (C5-C10) heteroaryl ring.

R4 is selected from the group consisting of H, halogen, (C1-C8) alkyl, (C0-C4) alkylene-O—(C0-C4) alkylene-H, (C3-C7) cycloalkyl, SCH3, CN and (C6-C10) aryl, wherein alkyl, alkylene and aryl are unsubstituted or 1- to 5-fold substituted by F;

X is selected from the group consisting of O, S, S(O), S(O)2, O—CH2, S—CH2, CH2—O, CH2—S and —CH2—;

Z is a bond, (C1-C8) alkylene, (C2-C8) alkenylene, (C2-C8) alkylidene, or (C1-C6) alkylene-O—(C1-C6) alkyl;

U or V is N and the other is S or O;

W is selected from the group consisting of a bond, (C1-C8) alkylene and (C2-C8) alkenylene wherein alkylene and alkenylene are unsubstituted or mono-, di- or tri-substituted by OH and F;

Y is a bond, O, S, S(O), S(O)2 or N(R6) and

R5 is selected from the group consisting of H, (C1-C8) alkyl, (C0-C4) alkylene-(C3-C13) cycloalkyl, (C0-C4) alkylene-(C6-C14) aryl, (C2-C8) alkenyl, (C0-C4) alkylene-(C3-C15) heterocycloalkyl, (C0-C4) alkylene-(C3-C15) heterocycloalkenyl, and (C0-C4) alkylene-(C5-C15) heteroaryl, wherein alkyl and alkylene is optionally mono-, di- or tri-substituted by F, (C1-C4) alkyl and O—(C0-C4) alkylene-H and wherein cycloalkyl, aryl, heterocycloalkyl, heterocycloalkenyl and heteroaryl are optionally mono-, di- or tri-substituted by F, Cl, Br, CF3, (C1-C4) alkyl and O—(C0-C4) alkylene-H;

R6 is selected from the group consisting of H, (C1-C8) alkyl, (C2-C8) alkenyl, and (C0-C4) alkylene-(C3-C6) cycloalkyl, wherein alkyl and alkenyl are unsubstituted or mono-, di- or tri-substituted by F and O—(C0-C4)-alkylene-H; or R5 and R6 together with the nitrogen atom to which they are bonded (Y=N(R6)) form a (C3-C9)-heterocycloalkyl, a (C3-C9)-heterocycloalkenyl or a (C5-C9)-heteroaryl which can contain additionally 1 to 3 heteroatoms N, O, S and which is unsubstituted or mono- or di-substituted by F, CF3, (C1-C4) alkyl, O—(C1-C4) alkyl, CH2—OH, SO2—(C1-C4) alkyl, CO—(C1-C4) alkyl, C0—NH2, NH—CO—(C1-C4) alkyl, (C6-C14) aryl and (C5-C15) heteroaryl;

R7 and R8 are independently selected from the group consisting of H, halogen, (C1-C8) alkyl, (C0-C4) alkylene-O—(C0-C4) alkylene-H, SCF3, SF5, S(O)2CF3, (C0-C4) alkylene-O—(C6-C12) aryl, (C0-C4) alkylene-(C6-C12) aryl, and NO2, wherein alkyl and alkylene are unsubstituted or mono-, di- or tri-substituted by F and aryl is unsubstituted or mono-, di- or tri-substituted by halogen, (C1-C4) alkyl or O—(C1-C4) alkyl;

R9 is selected from the group consisting of(C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, and (C0-C6) alkylene-(C3-C8) cycloalkenyl, wherein alkyl and alkylene are unsubstituted or mono-, di- or tri-substituted by F and aryl, heteroaryl, cycloalkyl and cycloalkenyl are unsubstituted or mono-, di- or tri-substituted by halogen, (C1-C4) alkyl, —CF3, —CHF2, or O—(C1-C4)alkyl;

R10 is selected from the group consisting of H, F, (C1-C6) alkyl, (C2-C6) alkenyl, (C0-C6) alkylene-(C6-C14) aryl, (C0-C6) alkylene-(C5-C15) heteroaryl, (C0-C6) alkylene-(C3-C8) cycloalkyl, and (C0-C6) alkylene-(C3-C8) cycloalkenyl, wherein alkyl and alkylene are unsubstituted or mono-, di- or tri-substituted by F and aryl, heteroaryl, cycloalkyl and cycloalkenyl are unsubstituted or mono-, di- or tri-substituted by halogen, (C1-C4) alkyl, —CF3, —CHF2, or O—(C1-C4) alkyl;

or a stereoisomer or an enantiomer, or a mixture thereof, a tautomer, or a physiologically acceptable salt thereof.

2. The compound of formula I as recited in claim 1, wherein,
B is C(R4) and
R4 is H.

3. The compound of formula I as recited in claim 2, wherein,
X is O or O—CH2.

4. The compound of formula I as recited in claim 3 wherein,
R1 is selected from the group consisting of H, halogen, (C1-C4) alkyl, (C0-C4) alkylene-O—(C0-C2) alkylene-H, (C3-C6) cycloalkyl and phenyl, wherein alkyl, alkylene and phenyl are unsubstituted or mono, di- or tri-substituted by F.

5. The compound of formula I as recited in claim 4, wherein
R2 is H and
R3 is H or F
or
R2 and R3 together with the carbon atoms to which they are bonded form a (C6)-aryl or a (C5-C6) heteroaryl ring.

6. The compound of formula I as recited in claim 5 wherein,
W is CH2,
Y is a bond, and
R5 is H.

7. The compound of formula I as recited in claim 6 wherein,
Z is a bond.

8. The compound of formula I as recited in claim 7, wherein
U is S and
V is N.

9. The compounds of formula I as recited in claim 8 wherein,
R7 is selected from the group consisting of F, Cl, (C1-C4) alkyl, (C0-C2) alkylene-O—(C1-C2) alkylene-H, and (C0-C4) alkylene-phenyl, wherein alkyl, alkylene and phenyl are unsubstituted or mono-, di- or tri-substituted by F, and
R8 is H.

10. The compound of formula I as recited in claim 9 wherein,
R9 is (C1-C4) alkyl, (C0-C3) alkylene-(C6-C10) aryl, (C0-C3) alkylene-(C5-C6) heteroaryl, and (C0-C3) alkylene-(C3-C6) cycloalkyl, wherein alkyl and alkylene, are unsubstituted or mono-, di- or tri-substituted by F and aryl, heteroaryl and cycloalkyl are unsubstituted or mono-, di- or tri-substituted by halogen, (C1-C4) alkyl, —CF3, —CHF2, or O—(C1-C4)alkyl; and
R10 is H.

11. The compound of formula I as claimed in claims 1, wherein
W is a bond or (C1-C3) alkylene;
Y is a bond or N(R6);
R5 is H or (C1-C3) alkyl, wherein alkyl is optionally mono-, di- or tri-substituted by F;
R6 is H or (C1-C3) alkyl, wherein alkyl is optionally mono-, di- or tri-substituted by F; or
R5 and R6, together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl.

12. The compound of formula I as recited in claim 11 wherein,
R1 is selected from the group consisting of H, halogen, OH, O—(C1-C2) alkyl, and (C3-C6) cycloalkyl, wherein alkyl is unsubstituted or mono, di- or tri-substituted by F;
R2 is H;
R3 is H, F;
B is C(R4);
R4 is H;
X is O or O—CH2;
V is N and
U is O or S;
W is a bond or CH2;
Y is a bond or N(R6);
R5 is H or (C1-C3) alkyl, wherein alkyl is optionally mono-, di- or tri-substituted by F;
R6 is H or (C1-C3) alkyl, wherein alkyl is optionally mono-, di- or tri-substituted by F; or,
R5 and R6 together with the nitrogen atom to which they are bonded (Y=N(R6)) form a (C4-C6)-heterocycloalkyl, which can contain additionally 1 to 2 heteroatoms N, O, S and which is unsubstituted or mono- or di-substituted by F, CF3, (C1-C3) alkyl, O—(C1-C3) alkyl; preferably piperidine which is unsubstituted or mono- or di-substituted by F, CF3, (C1-C3) alkyl, O—(C1-C3) alkyl; most preferably piperidine monosubstituted by CF3;

Z is a bond;

R7 is selected from the group consisting of H, halogen, (C1-C3) alkyl, O—(C1-C3) alkyl and phenyl, wherein alkyl and phenyl are unsubstituted or mono-, di- or trisubstituted by F;

R8 is H;

R9 is (C1-C4) alkyl, (C0-C3) alkylene-phenyl, (C0-C3) alkylene-(C5-C6) heteroaryl, and (C0-C3) alkylene-(C3-C6) cycloalkyl, wherein alkyl, alkylene, phenyl and heteroaryl are unsubstituted or mono-, di- or tri-substituted by F;

R10 is H.

13. The compound of formula I as recited in claim 12 wherein,
R1 is H, halogen, (C1-C2) alkylene-O—(C1-C2) alkyl or (C3-C6) cycloalkyl, wherein alkylene and alkyl are unsubstituted or mono, di- or trisubstituted by F;
R2 is H;
R3 is H or F;
B is C(R4) and
R4 is H;
X is O or O—CH2;
V is N and
U is O or S;
W is CH2;
Y is a bond;
R5 is H;
Z is a bond;
R7 is selected from the group consisting of H, halogen, (C1-C3) alkyl, O—(C1-C3) alkyl, and phenyl, wherein alkyl and phenyl are unsubstituted or mono-, di- or trisubstituted by F;
R8 is H;
R9 is selected from the group consisting of (C1-C4) alkyl, (C0-C3) alkylene-phenyl, (C0-C3) alkylene-(C5-C6) heteroaryl and (C0-C3) alkylene-(C3-C6) cycloalkyl, wherein alkyl, alkylene, phenyl, cycloalkyl and heteroaryl are unsubstituted or mono-, di- or tri-substituted by F; and
R10 is H.

14. The compound of formula I as recited in claim 13, wherein,
B is C(R4) or N;
R1 is selected from the group consisting of H, F, Cl, Br, OH, O—CH3, O—CHF2, O—CH2—CF3, CF3, CH2—CH3, CH2—O—CH2—CF3, CH2—O—CH3, CH2—O—CH2—CH3 and cyclopropyl;
R2 is H;
R3 is H or F;
R4 is H; or
R2 and R3 together with the C-atoms to which they are bonded and the ring carrying them form a naphthalene or a quinoline-ring.
X is O, CH2 or O—CH2;
V is N,
U is S;
w is CH2;
Y is a bond or N(R6);
R5 is H; or
R5 and R6 together with the nitrogen atom to which they are bonded (Y=N(R6)) form a piperidine which is monosubstituted by CF3;

Z is a bond;
R7 is CF3;
R8 is H;
R9 is selected from the group consisting of CH3, CH2CH3, C3H7, C4H9, CF3, CF2—CH2-CH3, phenyl, CH2-phenyl, CH2—CH2-phenyl, CH2-4-F-phenyl, CH2-pyridyl, CF2-cyclopropyl, and CF2-4-CHF2-phenyl; and
R10 is H.

15. A pharmaceutical composition comprising one or more compounds of formula I as recited in claim 1.

16. A pharmaceutical composition comprising one or more compounds of formula I as recited in claim 1 in combination with one or more additional active pharmaceutical compounds which are therapeutically effective in the treatment of metabolic disorders and the physiological manifestations thereof.

17. A pharmaceutical composition comprising one or more compounds of formula I as recited in claim 1 in combination with one or more anti-diabetics.

18. A pharmaceutical composition comprising one or more compounds of formula I as recited in claim 1 in combination with one or more additional active pharmaceutical compounds which are therapeutically effective in the modulation of lipids and the physiological manifestations thereof.

19. A pharmaceutical composition comprising one or more compounds of formula I as recited in claim 1 in combination with one or more additional active pharmaceutical compounds which are therapeutically effective in the treatment of fatty acid metabolism and glucose utilization disorders and the physiological manifestations thereof.

20. A pharmaceutical composition comprising one or more compounds of formula I as recited in claim 1 in combination with one or more additional active pharmaceutical compounds which are therapeutically effective in the treatment of disorders caused by insulin resistance and the physiological manifestations thereof.

21. A pharmaceutical composition comprising one or more compounds of formula I as recited in claim 1 in combination with one or more additional active pharmaceutical compounds which are therapeutically effective in the treatment of diabetic disorders and the physiological manifestations thereof.

22. A pharmaceutical composition comprising one or more compounds of formula I as recited in claim 1 in combination with one or more additional active pharmaceutical compounds which are therapeutically effective in the treatment of dyslipidemias and the physiological manifestations thereof.

23. A pharmaceutical composition comprising one or more compounds of formula I as recited in claim 1 in combination with one or more additional active pharmaceutical compounds which are therapeutically effective in the treatment of disorders caused by the metabolic syndrome and the physiological manifestations thereof.

24. A pharmaceutical composition comprising one or more compounds of formula I as recited in claim 1 in combination with one or more additional active pharmaceutical compounds which are therapeutically effective in the treatment of demyelinating and other neurodegenerative disorders of the central and peripheral nervous system and the physiological manifestations thereof.

25. A method for the treatment of diabetic disorders and the physiological manifestations thereof comprising the administration of one or more compounds of formula I as recited in claim 1.

26. A method for the treatment of lipid disorders and the physiological manifestations thereof comprising the administration of one or more compounds of formula I as recited in claim 1.

27. A method for the treatment of dyslipidemias and the physiological manifestations thereof comprising the administration of one or more compounds of formula I as recited in claim 1.

28. A method for the treatment of fatty acid metabolism and glucose utilization disorders and the physiological manifestations thereof comprising the administration of one or more compounds of formula I as recited in claim 1.

29. A method for the treatment of disorders caused by the metabolic syndrome and the physiological manifestations thereof comprising the administration of one or more compounds of formula I as recited in claim 1.

30. A method for the treatment of demyelinating and other neurodegenerative disorders of the central and peripheral nervous system and the physiological manifestations thereof comprising the administration of one or more compounds of formula I as recited in claim 1.

31. A method for the treatment of disorders caused by insulin resistance and the physiological manifestations thereof comprising the administration of one or more compounds of formula I as recited in claim 1.

32. A process for preparing a pharmaceutical comprising one or more of the compounds as recited in claim 1 which comprises mixing the active compound with a pharmaceutically suitable carrier and bringing this mixture into a form suitable for administration.

* * * * *